US011623965B2

(12) United States Patent
Krystek, Jr. et al.

(10) Patent No.: US 11,623,965 B2
(45) Date of Patent: Apr. 11, 2023

(54) PRODRUGGABLE ANTIBODIES, PRODRUGS THEREOF, AND METHODS OF USE AND MAKING

(71) Applicant: BRISTOL-MYERS SQUIBB COMPANY, Princeton, NJ (US)

(72) Inventors: Stanley R. Krystek, Jr., Ringoes, NJ (US); Yong Zhang, West Windsor, NJ (US); Gregory D. Vite, Titusville, NJ (US); Arvind Rajpal, San Francisco, CA (US); Chetana Rao-Naik, Walnut Creek, CA (US); Paul E. Morin, Pennington, NJ (US); Mohan Srinivasan, Cupertino, CA (US); Zheng Lin, North Wales, PA (US); Virginie Lafont, Lawrence Township, NJ (US); Alla Pritsker, Morganville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1007 days.

(21) Appl. No.: 16/103,654

(22) Filed: Aug. 14, 2018

(65) Prior Publication Data
US 2019/0055321 A1 Feb. 21, 2019

Related U.S. Application Data

(60) Provisional application No. 62/546,252, filed on Aug. 16, 2017.

(51) Int. Cl.
*C07K 16/46* (2006.01)
*A61K 39/395* (2006.01)
*A61K 47/60* (2017.01)
*A61K 47/65* (2017.01)
*C07K 16/28* (2006.01)
*A61P 29/00* (2006.01)
*A61P 35/00* (2006.01)

(52) U.S. Cl.
CPC ...... *C07K 16/464* (2013.01); *A61K 39/39533* (2013.01); *A61K 47/60* (2017.08); *A61K 47/65* (2017.08); *C07K 16/2818* (2013.01); *C07K 16/2878* (2013.01); *A61P 29/00* (2018.01); *A61P 35/00* (2018.01); *C07K 2317/24* (2013.01); *C07K 2317/515* (2013.01); *C07K 2317/565* (2013.01); *C07K 2317/76* (2013.01); *C07K 2319/50* (2013.01); *C12Y 304/21109* (2013.01)

(58) Field of Classification Search
CPC ........ A61K 47/60; A61K 47/65; A61K 47/68; A61K 47/56
See application file for complete search history.

(56) References Cited

U.S. PATENT DOCUMENTS

| | | | |
|---|---|---|---|
| 4,732,863 A | 3/1988 | Tomasi et al. | |
| 8,399,219 B2 | 3/2013 | Stagliano et al. | |
| 8,623,357 B2 | 1/2014 | Waldmann et al. | |
| 8,809,504 B2 | 8/2014 | Lauermann | |
| 9,120,853 B2 | 9/2015 | Lowman et al. | |
| 9,127,053 B2 | 9/2015 | West et al. | |
| 9,169,321 B2 | 10/2015 | Daugherty et al. | |
| 9,193,791 B2 | 11/2015 | Williams et al. | |
| 9,453,078 B2 | 9/2016 | Stagliano et al. | |
| 9,487,590 B2 | 11/2016 | West et al. | |
| 9,540,440 B2 | 1/2017 | Lowman et al. | |
| 9,562,073 B2 | 2/2017 | Moore et al. | |
| 2004/0014652 A1 | 1/2004 | Trouet et al. | |
| 2007/0092940 A1 | 4/2007 | Eigenbrot et al. | |
| 2010/0189727 A1 | 7/2010 | Rodeck et al. | |
| 2012/0149061 A1* | 6/2012 | Stagliano .............. | C07K 16/30 435/69.6 |
| 2013/0028893 A1 | 1/2013 | Waldmann et al. | |
| 2014/0023664 A1 | 1/2014 | Lowman et al. | |
| 2015/0079088 A1 | 3/2015 | Lowman et al. | |
| 2015/0087810 A1 | 3/2015 | Moore et al. | |
| 2016/0009817 A1 | 1/2016 | Wang et al. | |
| 2016/0130358 A1 | 5/2016 | Bhakta et al. | |
| 2016/0215060 A1 | 7/2016 | Chung et al. | |
| 2016/0311903 A1 | 10/2016 | West et al. | |
| 2016/0355587 A1 | 12/2016 | West et al. | |
| 2016/0355592 A1 | 12/2016 | Sagert et al. | |
| 2016/0355599 A1 | 12/2016 | Sagert et al. | |
| 2017/0044259 A1 | 2/2017 | Tipton et al. | |
| 2018/0057593 A1 | 3/2018 | Dennis | |

FOREIGN PATENT DOCUMENTS

| | | | |
|---|---|---|---|
| WO | 2001014424 A2 | 3/2001 | |
| WO | WO-2006034488 A2 * | 3/2006 | ............. A61K 45/06 |

(Continued)

OTHER PUBLICATIONS

Al-Lazikani, et al., Standard Conformations for the Canonical Structures of Immunoglobulins, 1997, 927-948, 273, JMB.
Alan Korman, Next Generation ANTI-CTLA4 Antibodies, 2017, Cancer Research.
Chothia, et al., Canonical Structures for the Hypervariable Regions of Immunoglobulins, 1987, 901-917, 196, J. Mol. Biol.
Chothia, et al., Conformation of I8mmunogloulin Hypervariable Regions, 1989, 877-883, 342:21/28, Nature.
Desnoyers, et al., Tumor-Specific Activation of an EGFR-Targeting Probody Enhances Therapeutic Index, 2013, 1-10, 5:207, Science Translation Medicine.
Foot, et al., Antibody Framework Residues Affecting the Conformation of the Hypervariable Loops, 1992, 487-499, 224, J. Mol. Biol.

(Continued)

*Primary Examiner* — Karen A. Canella
(74) *Attorney, Agent, or Firm* — Bing Hai

(57) ABSTRACT

A prodrugged antibody has a blocking moiety attached to a Cys on its heavy or light chain via a linker having a cleavable moiety. The blocking moiety inhibits binding of the antibody to its antigen. Cleavage of the cleavable moiety releases the blocking moiety and restores ability of the antibody to bind to its antigen.

11 Claims, 23 Drawing Sheets

Figure 1:
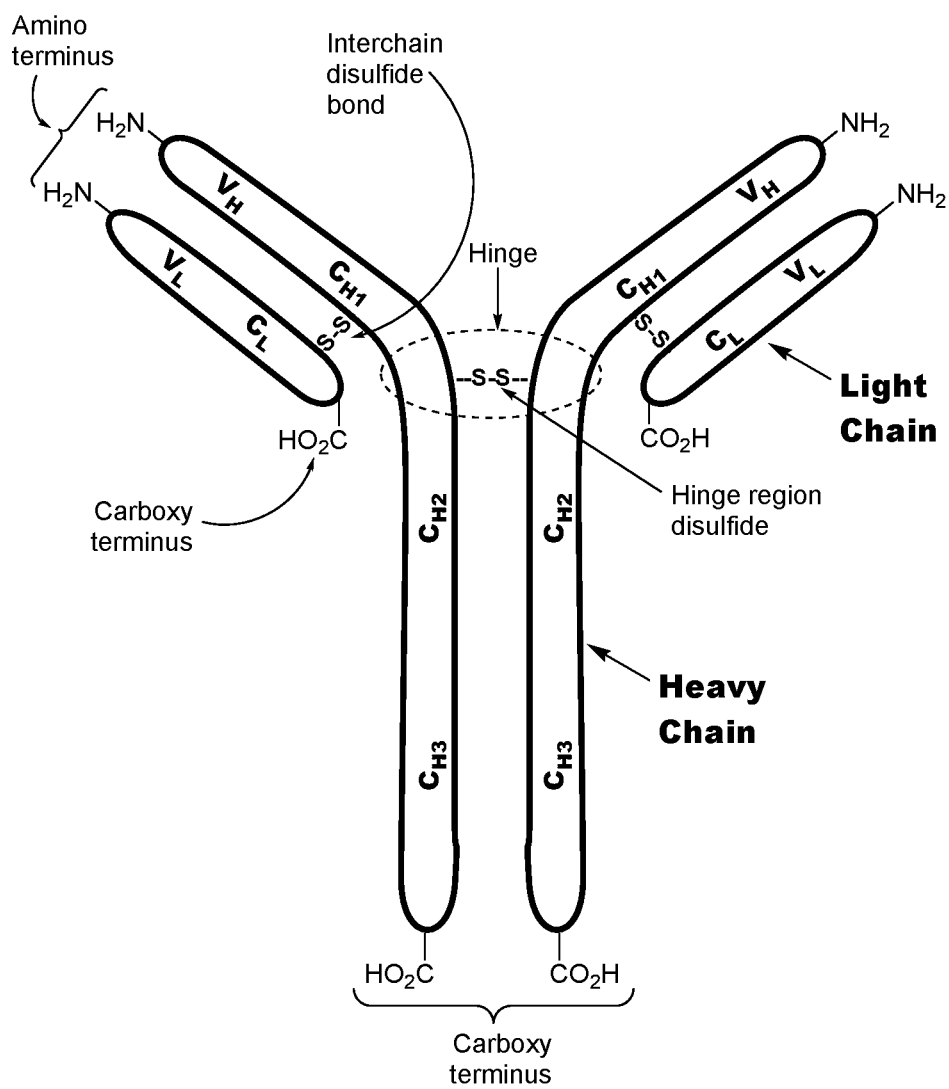

Specification includes a Sequence Listing.

(56) References Cited

FOREIGN PATENT DOCUMENTS

| WO | 2012100343 A1 | 8/2012 |
|---|---|---|
| WO | 2015116933 A2 | 8/2015 |

OTHER PUBLICATIONS

ISR, PCT Inernational Search Report dated Feb. 21, 2019, 2019, EPO_ISA.
Kabat, et al., Tabulation and Analysis of Amino Acid and Nucleic Acid Sequences of Recursors, 1991, 1-8, 91-3242, NIH.
Lee, et al., The Interpretation of Protein Structures: Estimation of Static Accessibility, 1971, 379-400, 5, J. Mol. Biol.
Makabe, et al., Thermodynamic Consequences of Mutations in Vernier Zone Residues of a Humanized Anti-human Epidermal Growth Factor Receptor Murine Antibody, 528, 2008,1156-1166, 283:2, Journal of Biological Chemmistry.
Miller, et al., Interior and Surface of Monomeric Proteins, 1987, 641-656, 196, J. Mol. Biol.
Polu ET A;/Q, Probody therapeutics for targeting antibodies diseased tissue to, 2014, 1049-1053, 14:8, ExpOpBiolTher.
Liu Meng et al.: "Matriptase is Highly up-Regulated in Chronic Lymphocytic Leukemia and Promotes Cancer Cell Invasion", Blood, American Society of Hematology, US, vol. 120, No. 21, Nov. 16, 2012 (Nov. 16, 2012), p. 4612.
W. Michael Kavanaugh (2020): "Antibody prodrugs for cancer", Expert Opinion on Biological Therapy, 20:2, 163-171, DOI: 10.1080/14712598.2020.1699053.

* cited by examiner

FIG. 2

Anti-CTLA4 Antibody Heavy Chain Variable Region

```
 ♦     ♦    ♦
Gln Val Gln Leu Val Glu Ser Gly Gly Gly Val Val Gln Pro Gly Arg            SEQ ID NO:1
1           5               10              15                             Kabat No.
1           5               10              15

♦                ♦   ♦
Ser Leu Arg Leu Ser Cys Ala Ala Ser Gly Phe Thr Phe Ser Ser Tyr            SEQ ID NO:1
            20              25              30                             Kabat No.
            20              25              30

♦           ♦
Thr Met His Trp Val Arg Gln Ala Pro Gly Lys Gly Leu Glu Trp Val            SEQ ID NO:1
        35                  40              45                             Kabat No.
        36                  40              45

Thr Phe Ile Ser Tyr Asp Gly Asn Asn Lys Tyr Tyr Ala Asp Ser Val            SEQ ID NO:1
    50              55              60                                     Kabat No.
49

♦           ♦       ♦   ♦   ♦
Lys Gly Arg Phe Thr Ile Ser Arg Asp Asn Ser Lys Asn Thr Leu Tyr            SEQ ID NO:1
65              70              75              80                         Kabat No.
        66                  72          76

♦   ♦       ♦   ♦   ♦
Leu Gln Met Asn Ser Leu Arg Ala Glu Asp Thr Ala Ile Tyr Tyr Cys            SEQ ID NO:1
            85              90              95                             Kabat No.
    81  82a 82c         84      86              90

♦
Ala Arg Thr Gly Trp Leu Gly Pro Phe Asp Tyr Trp Gly Gln Gly Thr            SEQ ID NO:1
        100             105                 110                            Kabat No.
94                                      103         106

Leu Val Thr Val Ser Ser
        115         118    SEQ ID NO:1
        110         113    Kabat No.
```

KEY: <u>Bold Underline</u> = CDR amino acid (per Kabat)    ♦ = Cys substitution site

FIG. 3

Anti-CTLA4 Antibody Light (Kappa) Chain Variable Region

```
  ♦       ♦     ♦     ♦   ♦
Glu Ile Val Leu Thr Gln Ser Pro Gly Thr Leu Ser Leu Ser Pro Gly
1           5                   10                  15           SEQ ID NO:2
1           5                   10                  15           Kabat No.

♦       ♦
Glu Arg Ala Thr Leu Ser Cys Arg Ala Ser Gln Ser Val Gly Ser Ser
            20              23  25                  30           SEQ ID NO:2
            20              23                                   Kabat No.

♦
Tyr Leu Ala Trp Tyr Gln Gln Lys Pro Gly Gln Ala Pro Arg Leu Leu
        35              40              45                       SEQ ID NO:2
            35              40              44                   Kabat No.

♦           ♦               ♦
Ile Tyr Gly Ala Phe Ser Arg Ala Thr Gly Ile Pro Asp Arg Phe Ser
    50              55              57      60          62       SEQ ID NO:2
    49              55              57      60          62       Kabat No.

♦   ♦   ♦       ♦                               ♦
Gly Ser Gly Ser Gly Thr Asp Phe Thr Leu Thr Ile Ser Arg Leu Glu
65              70                  75                  80       SEQ ID NO:2
64          67      70              75                  79       Kabat No.

Pro Glu Asp Phe Ala Val Tyr Tyr Cys Gln Gln Tyr Gly Ser Ser Pro
                85              88  90                  95       SEQ ID NO:2
81              85      86      88                               Kabat No.

♦
Trp Thr Phe Gly Gln Gly Thr Lys Val Glu Ile Lys
            100                 105         108    SEQ ID NO:2
        98      101             105     107        Kabat No.
```

KEY:  <u>Bold Underline</u> = CDR amino acid (per Kabat)    ♦ = Cys substitution site

FIG. 4

Anti-CD137 Antibody Heavy Chain Variable Region

| | | |
|---|---|---|
| Gln Val Gln Leu Lys Glu Ala Gly Pro Gly Leu Val Gln Pro Thr Gln<br>1                   5                            10                           15<br>1                   5                            10                           15 | SEQ ID NO:3<br>Kabat No. |

```
                              ♦
Thr Leu Ser Leu Thr Cys Thr Val Ser Gly Phe Ser Leu Thr Ser Asp     SEQ ID NO:3
            20              25              30                      Kabat No.
            20              25              30

Gly Val His Trp Ile Arg Gln Pro Pro Gly Lys Gly Leu Glu Trp Met     SEQ ID NO:3
        35              40              45                          Kabat No.
        36              40              45

Gly Ile Ile Tyr Tyr Asp Gly Gly Thr Asp Tyr Asn Ser Ala Ile Lys     SEQ ID NO:3
    50              55              60                              Kabat No.
49

Ser Arg Leu Ser Ile Ser Arg Asp Thr Ser Lys Ser Gln Val Phe Leu     SEQ ID NO:3
65              70              75                      80          Kabat No.
    66              72              76                  80

Lys Ile Asn Ser Leu Gln Thr Asp Asp Thr Ala Met Tyr Tyr Cys Ala     SEQ ID NO:3
            85              90              95                      Kabat No.
81          82c             86              90

Arg Ile His Phe Asp Tyr Trp Gly Gln Gly Val Met Val Thr Val Ser     SEQ ID NO:3
        100             105             110                         Kabat No.
94          103             106             110

Ser
113     SEQ ID NO:3
113     Kabat No.
```

KEY: <u>Bold Underline</u> = CDR amino acid (per Kabat)    ♦ = Cys substitution site

FIG. 5

Anti-CD137 Antibody Light (Kappa) Chain Variable Region

| Glu | Ile | Val | Leu | Thr | Gln | Ser | Pro | Thr | Thr | Ile | Ala | Ala | Ser | Pro | Gly | |
|---|---|---|---|---|---|---|---|---|---|---|---|---|---|---|---|---|
| 1 | | | | 5 | | | | | 10 | | | | | 15 | | SEQ ID NO:4 |
| 1 | | | | 5 | | | | | 10 | | | | | 15 | | Kabat No. |

| Glu | Lys | Val | Thr | Ile | Thr | Cys | <u>Arg</u> | <u>Ala</u> | <u>Ser</u> | <u>Ser</u> | <u>Ser</u> | <u>Val</u> | <u>Ser</u> | <u>Tyr</u> | <u>Met</u> | |
|---|---|---|---|---|---|---|---|---|---|---|---|---|---|---|---|---|
| | | 20 | | | | | | 25 | | | | | 30 | | | SEQ ID NO:4 |
| | 19 | | | 23 | | | | | | | | | | | | Kabat No. |

| <u>Tyr</u> | Trp | Tyr | Gln | Gln | Lys | Ser | Gly | Ala | Ser | Pro | Lys | Leu | Trp | Ile | Tyr | |
|---|---|---|---|---|---|---|---|---|---|---|---|---|---|---|---|---|
| | | 35 | | | | | 40 | | | | | 45 | | | | SEQ ID NO:4 |
| 35 | | | | 39 | | | | | 44 | | | | | | 49 | Kabat No. |

| <u>Asp</u> | <u>Thr</u> | <u>Ser</u> | <u>Lys</u> | <u>Leu</u> | <u>Ala</u> | <u>Ser</u> | Gly | Val | Pro | Asn | Arg | Phe | Ser | Gly | Ser | |
|---|---|---|---|---|---|---|---|---|---|---|---|---|---|---|---|---|
| 50 | | | | | | 55 | | | | | 60 | | | | | SEQ ID NO:4 |
| | | | | | | | 57 | | | | | 62 | | 64 | | Kabat No. |

♦

| Gly | Ser | Gly | Thr | Ser | Tyr | Ser | Leu | Ala | Ile | Asn | Thr | Met | Glu | Thr | Glu | |
|---|---|---|---|---|---|---|---|---|---|---|---|---|---|---|---|---|
| 65 | | | | 70 | | | | | 75 | | | | | 80 | | SEQ ID NO:4 |
| | 67 | | | | 70 | | 73 | 75 | | | | | | | 81 | Kabat No. |

| Asp | Ala | Ala | Thr | Tyr | Tyr | Cys | <u>Gln</u> | <u>Gln</u> | <u>Trp</u> | <u>Ser</u> | <u>Ser</u> | <u>Thr</u> | <u>Pro</u> | <u>Leu</u> | <u>Thr</u> | |
|---|---|---|---|---|---|---|---|---|---|---|---|---|---|---|---|---|
| | | | | 85 | | | | | 90 | | | | | 95 | | SEQ ID NO:4 |
| | | | | 86 | | 88 | | | | | | | | | | Kabat No. |

| Phe | Gly | Ser | Gly | Thr | Lys | Leu | Glu | Ile | Lys | | |
|---|---|---|---|---|---|---|---|---|---|---|---|
| | | | 100 | | | | | | 106 | SEQ ID NO:4 | |
| 98 | | | 101 | | | 105 | | | 107 | Kabat No. | |

KEY: <u>Bold Underline</u> = CDR amino acid (per Kabat)      ♦ = Cys substitution site

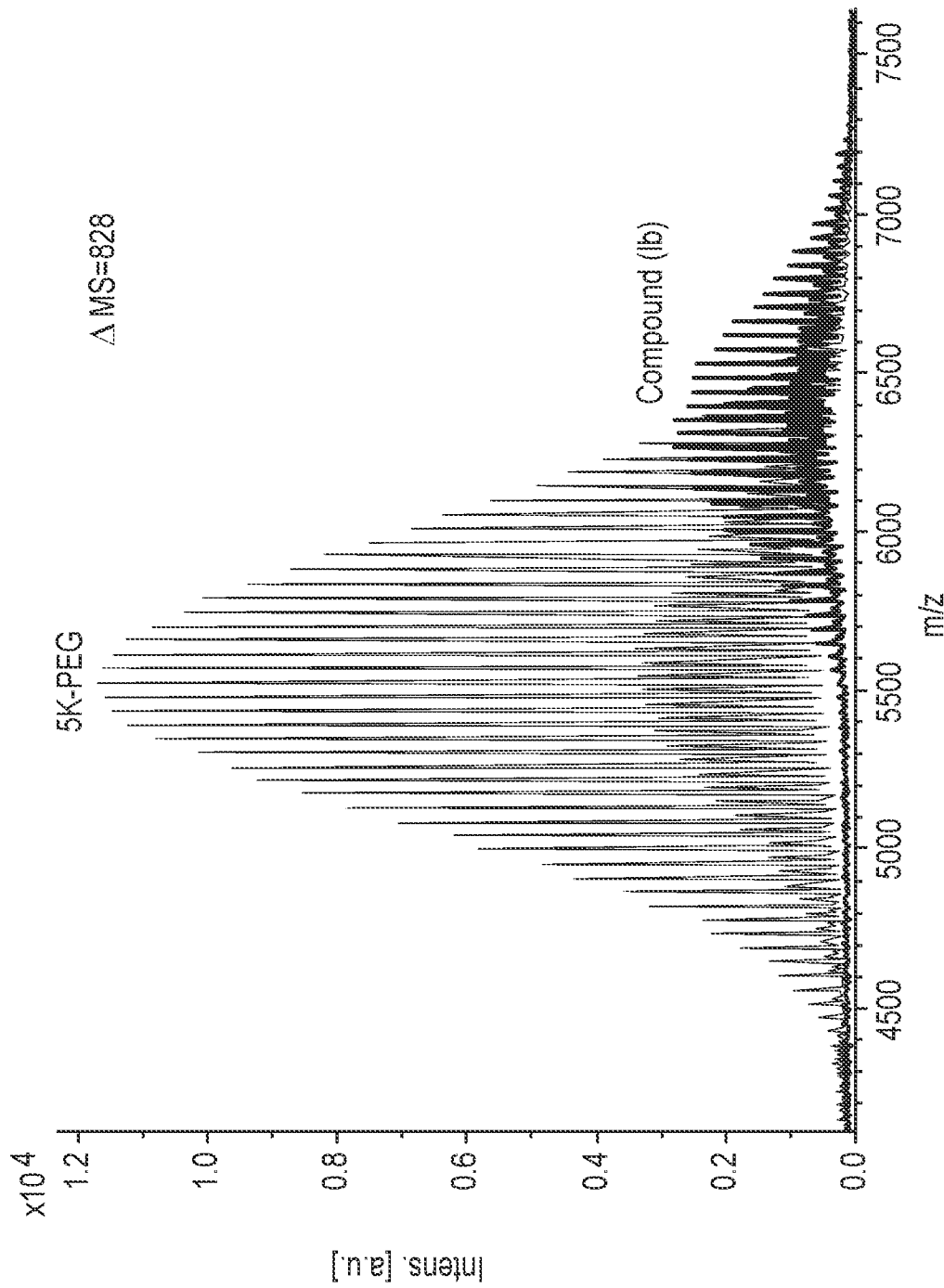

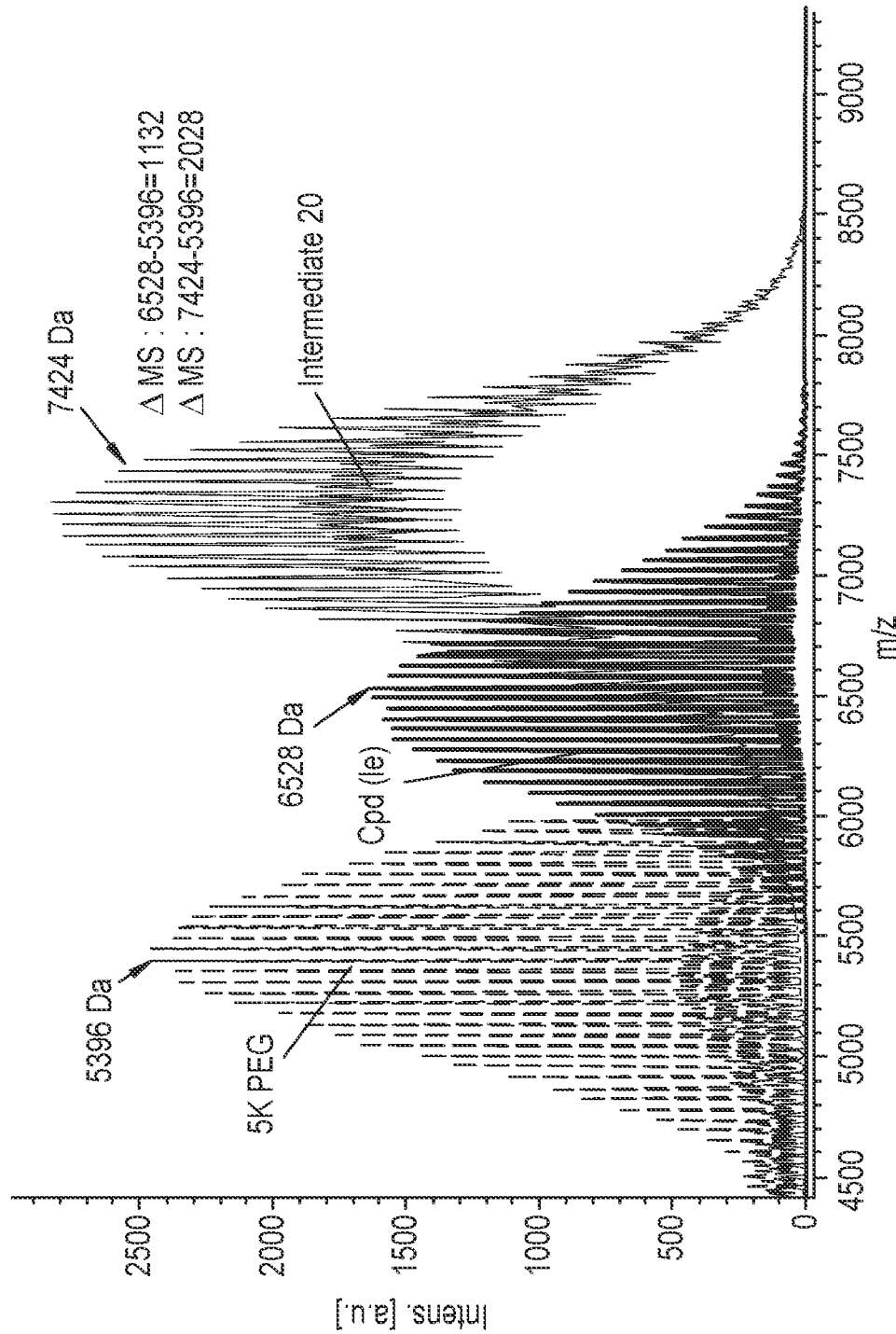

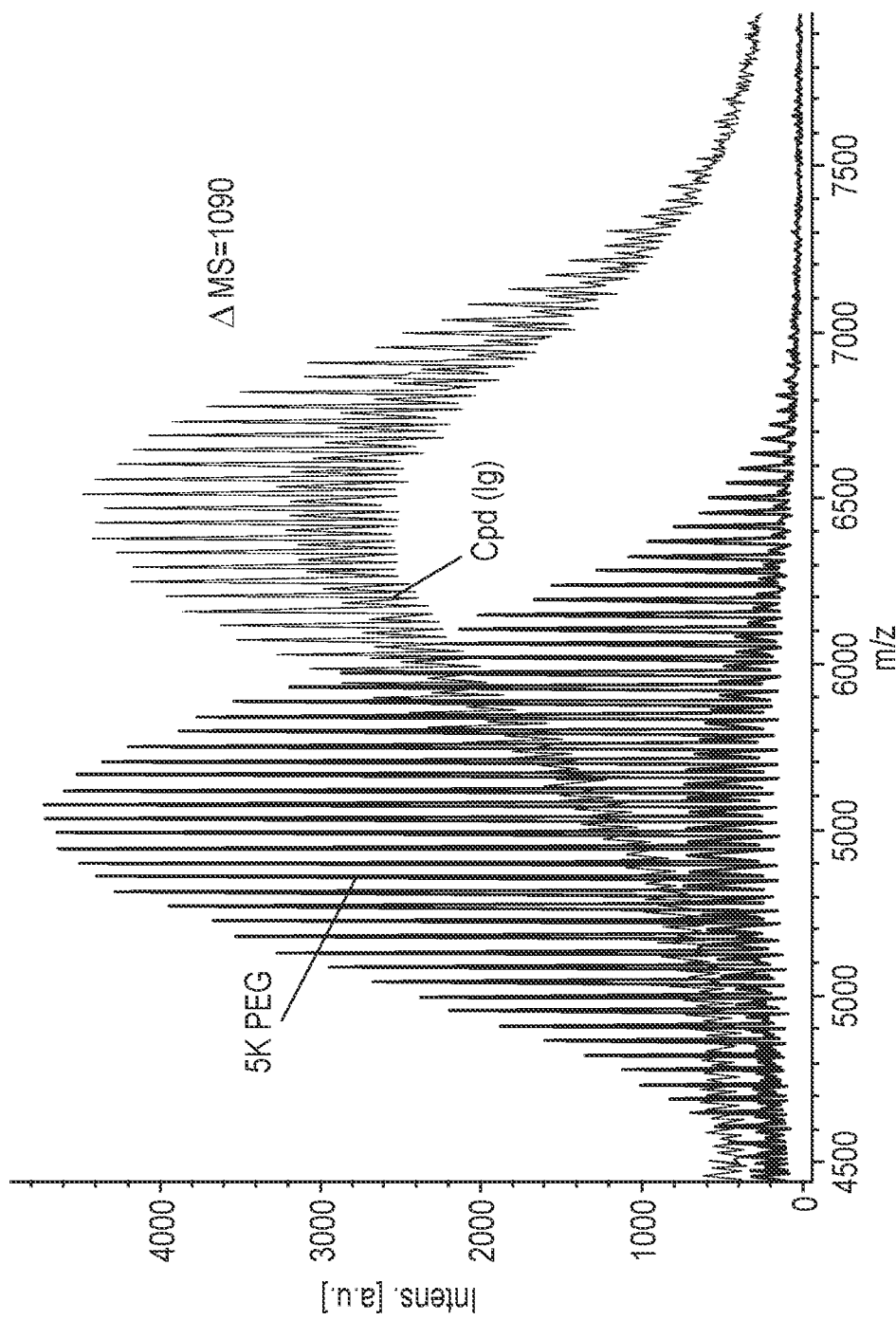

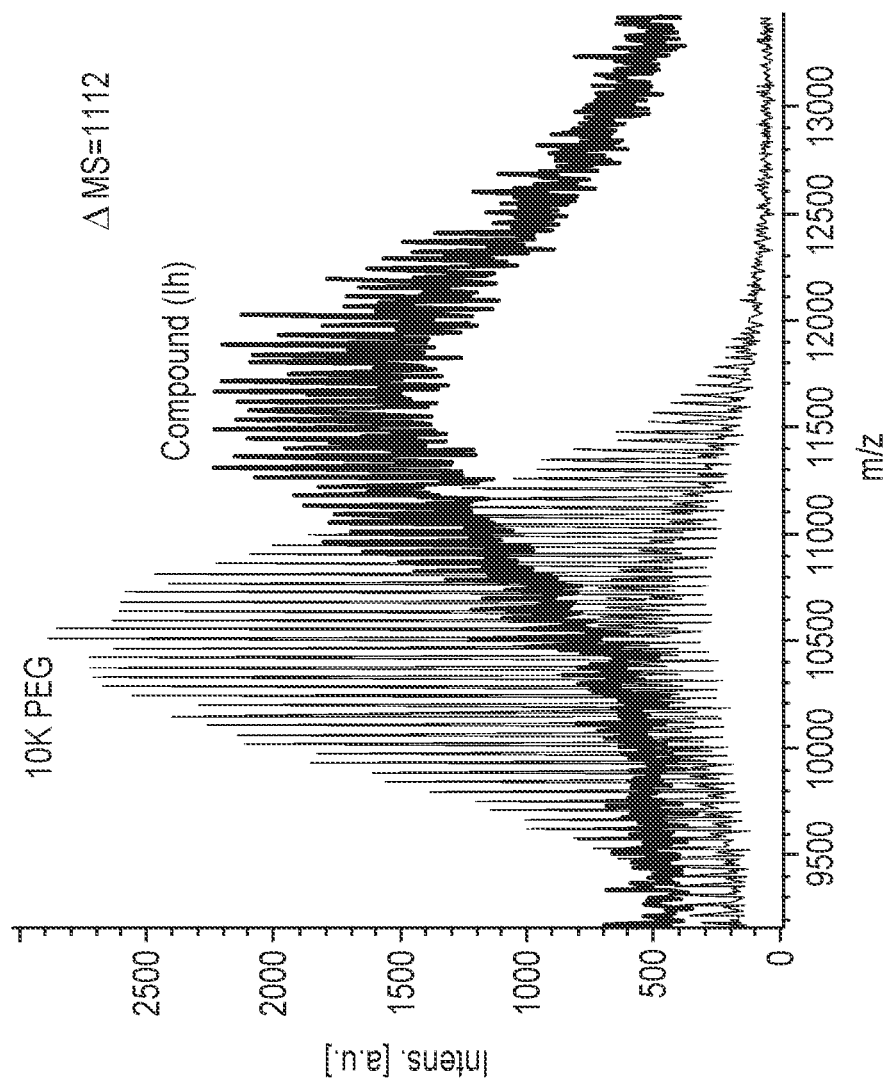

FIG. 10A

| > 30% Exposure and within 5Å of a CDR |||||||
|---|---|---|---|---|---|---|
| Heavy Chain |||||||
| Residue | Kabat No. | Type | ASA (Å²) | Exposure (%) | Near 5 Å | HCDR/LCDR 10 Å |
| GLN | 1 | polar | 186.39 | 93.27 | H | L |
| GLN | 3 | polar | 90.47 | 45.27 | H | |
| SER | 25 | polar | 68.28 | 46.83 | H | |
| GLU | 46 | acidic | 62.28 | 30.03 | H | L |
| THR | 68 | polar | 60.08 | 34.45 | H | |
| ASP | 72 | acidic | 53.03 | 30.02 | H | |
| ASN | 76 | polar | 53.88 | 31.21 | H | |
| ASN | 82a | polar | 65.37 | 37.86 | H | |
| ARG | 83 | basic | 114.72 | 42.48 | H | |
| Light Chain |||||||
| GLU | 1 | acidic | 139.66 | 67.33 | L | H |
| VAL | 3 | hyd | 84.74 | 43.37 | L | |
| THR | 5 | polar | 83.78 | 48.03 | L | |
| SER | 7 | polar | 67.31 | 46.16 | L | |
| PRO | 8 | hyd | 62.79 | 36.57 | L | |
| ARG | 45 | basic | 122.75 | 45.45 | HL | |
| GLY | 57 | polar | 71.84 | 71.62 | L | H |
| ASP | 60 | acidic | 118.96 | 67.34 | L | |
| SER | 63 | polar | 44.36 | 30.42 | L | |
| SER | 65 | polar | 59.64 | 40.9 | L | |
| GLY | 66 | polar | 39.56 | 39.43 | L | |
| SER | 67 | polar | 88.12 | 60.43 | L | |
| THR | 69 | polar | 55.45 | 31.79 | L | |

FIG. 10B

| > 30% Exposure and within 10Å of a CDR ||||||
|---|---|---|---|---|---|
| Heavy Chain ||||||
| | | | ASA | Exposure | Near | HCDR/LCDR |
| Residue | Number | Type | (Å²) | (%) | 5 Å | 10 Å |
| VAL | 5 | hyd | 85.61 | 43.81 | | H |
| ARG | 19 | basic | 122.3 | 45.29 | | H |
| ALA | 23 | hyd | 50.92 | 37.1 | | H |
| LYS | 43 | basic | 144.86 | 61.52 | | H |
| SER | 74 | polar | 120.21 | 82.44 | | H |
| LYS | 75 | basic | 131.68 | 55.92 | | H |
| SER | 82b | polar | 55.59 | 38.12 | | H |
| ALA | 84 | hyd | 62.57 | 45.58 | | H |
| GLU | 85 | acidic | 115.51 | 55.69 | | H |
| GLN | 105 | polar | 105.67 | 52.88 | | H |
| Light Chain ||||||
| ARG | 18 | basic | 144.19 | 53.39 | | L |
| THR | 20 | polar | 63.48 | 36.4 | | L |
| ARG | 77 | basic | 127.23 | 47.11 | | L |
| GLN | 100 | polar | 109.71 | 54.9 | | L |

PRODRUGGABLE ANTIBODIES, PRODRUGS THEREOF, AND METHODS OF USE AND MAKING

CROSS-REFERENCE TO RELATED APPLICATIONS

This application claims the benefit under 35 U.S.C. § 119(e) of U.S. Provisional Application Ser. No. 62/546,252, filed Aug. 16, 2017; the disclosure of which is incorporated herein by reference.

SEQUENCE LISTING

Incorporated herein by reference in its entirety is a Sequence Listing named "170731_SEQT_13002USNP_YC.txt" comprising SEQ ID NO:1 through SEQ ID NO:16, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Jul. 31, 2017, and is approximately 17 KB in size.

BACKGROUND OF THE INVENTION

This application relates to prodruggable antibodies, prodrugs thereof, and methods of making and using such antibodies and their prodrugs.

Therapeutic antibodies can be used to treat a variety of diseases, especially cancer and inflammatory conditions. Examples of therapeutic antibodies that have received marketing approval from regulatory authorities include ipilimumab (YERVOY®), nivolumab (OPDIVO®), trastuzumab (HERCEPTIN®), cetuximab (ERBITUX®), rituximab (RITUXAN®), infliximab (REMICADE®), and adalimumab (HUMIRA®). Generally, a therapeutic antibody—like other antibodies—acts by binding with high specificity for and affinity to its molecular target (the antigen), to initiate the cellular processes related to its therapeutic action.

A prodrug can be used to reduce a therapeutic agent's off-target side effects. A prodrug is a version of a therapeutic agent that is less active, but which can be converted at or near the target tissue or organ into the active therapeutic agent. Commonly, prodrugging is achieved by covalently attaching to the therapeutic agent a moiety that reduces its activity. Removal of the blocking moiety at the target site by a factor or agent found there—low pH, an enzyme, anoxia, etc.—restores the activity of the therapeutic agent. See, for example: Trouet et al. 2004, Stagliano et al. 2013, Rodeck et al. 2010, and Lauermann 2014.

As with the case of other therapeutic agents such as small molecule drugs, it is desirable that the side effects of a therapeutic antibody be reduced or eliminated by interfering with its action on a tissue or organ other than the one targeted for disease treatment. Classically, an antibody is a Y-shaped dimeric protein, each dimer half consisting of two chains, a heavy and a light chain, as shown in FIG. 1. Commonly, the two dimer halves are identical and are covalently linked to each other by disulfide bonds. The binding interactions of an antibody with its antigen occur through the antibody's complementarity determining regions (CDRs), of which there are three (CDR1, CDR2, and CDR3) on each heavy and light chain, in the variable regions thereof. The heavy and light chain variable regions (labeled $V_H$ and $V_L$, respectively in FIG. 1) are located near the amino terminus of each protein chain.

For prodrugging an antibody, the $V_H$ and $V_L$ regions are potential sites for attachment of the blocking moiety due to the presence there of the CDRs responsible for antigen interactions. For example, Polu and Lowman 2014 disclose prodrugging an antibody by attaching a masking peptide to the N-terminus of the light chain of an antibody. Other disclosures relating to the prodrugging of antibodies include: Stagliano et al. 2016, Williams et al. 2015, Lowman et al. 2014, Lowman et al. 2015b, and Daugherty et al. 2015. Specific antibodies that have been prodrugged include those against these antigens: EGFR (Desnoyers et al. 2013, Lowman et al. 2015a, Lowman et al. 2017), JAGGED 1/2 (West et al. 2015), interleukin-6 receptor (West et al. 2016a), tissue factor pathway inhibitor (Wang et al. 2016), CD3 (Dennis et al. 2016), PDL1 (West et al. 2016b), CD166 (West et al. 2016c), CD71 (Sagert et al. 2016b), PD1 (Tipton et al. 2017), and ITGA3 (Sagert et al. 2016a).

Some of the documents discussed herein are cited by first author or inventor and year of publication. Their full bibliographic citations are listed in the REFERENCES section towards the end of this specification.

BRIEF SUMMARY OF THE INVENTION

This disclosure provides novel prodrugged antibodies and methods of making and using them. Briefly, an antibody is modified by the site-specific substitution of an amino acid in either the heavy or light chain variable region with a cysteine (Cys). The sulfhydryl (SH) group in the side chain of the substituted-in Cys serves as a chemical handle for attaching a prodrugging moiety comprising a blocking moiety (BM) that interferes with the antibody's ability to bind to its antigen. BM may be a group that sterically inhibits antibody-antigen binding, but otherwise does not specifically interact with either the antibody or the antigen. Alternatively, BM can interact with the antibody, for example by electrostatic or van der Waals forces. The prodrugging moiety further comprises a linker moiety having a cleavable group, whose cleavage by a factor found at the site of intended action of the antibody releases the blocking moiety and restores the ability of the antibody to bind to its antigen and exert its therapeutic effect. The cleavable group preferably is cleaved by a factor that is found at or near the site of intended action—low pH, an enzyme, anoxia, etc.; with an enzyme being preferred.

In some instances, BM can have pharmacological activity of its own after its release by cleavage of the linker moiety. In this way, a prodrugged antibody of this invention can deliver in one shot, as it were, two pharmacologically active agents: BM and the antibody.

The Cys substitution sites are selected such that replacing the original amino acid with a Cys does not detrimentally affect the ability of the antibody to specifically and strongly bind to its antigen. Further, removal of the prodrugging moiety can leave behind a residual chemical group still covalently attached to the Cys. We have discovered that, unexpectedly, this residual group also does not prevent antibody-antigen binding.

In one embodiment, there is provided a prodrugged antibody according to formula (I)

$$(\text{BM-L})_m\text{-Ab} \qquad (\text{I})$$

wherein
Ab is an antibody having at least one amino acid in its heavy or light chain variable region replaced by a Cys, wherein the replaced amino acid (a) is in a framework region; (b) has a side chain exposure of at least 30% and (c) is within 10 Å, preferably 5 Å, of a CDR amino acid;

BM is a blocking moiety that inhibits binding of Ab to its antigen;

each L is, independently, a linker moiety bonded to BM and Ab, L comprising a cleavable moiety and being bonded to Ab at aforesaid Cys; and m is 1, 2, 3, or 4.

In a preferred embodiment, the at least one replaced amino in antibody Ab is at Kabat position 1, 3, 5, 19, 23, 25, 43, 46, 68, 72, 74, 75, 76, 82a, 82b, 83, 84, 85, or 105 of the heavy chain variable region or at Kabat position 1, 3, 5, 7, 8, 18, 20, 45, 57, 60, 63, 65, 66, 67, 69, 77, or 100 of the light chain variable region.

In another preferred embodiment, the at least one replaced amino acid in antibody Ab is at Kabat position 23 of the heavy chain or Kabat position 67 of the light chain.

In another embodiment, there is provided an antibody having a Cys at Kabat position 67 of the light chain. The antibody can be an anti-CTLA4 antibody or an anti-CD137 antibody.

In another embodiment, there is provided an antibody having a Cys at Kabat position 23 of the heavy chain. The antibody can be an anti-CTLA4 antibody or an anti-CD137 antibody.

BRIEF DESCRIPTION OF THE DRAWING(S)

FIG. 1 shows the general architecture of an antibody, including the location of the heavy and light chain variable regions ($V_H$ and $V_L$), where Cys substitutions disclosed herein are made.

FIG. 2 shows the amino acid sequence of the variable region $V_H$ of the heavy chain (SEQ ID NO: 1) of an anti-CLTA4 antibody used to illustrate prodrugging concepts disclosed herein, annotated to correlate amino acid numbering in SEQ ID NO: 1 and in the Kabat system and to mark desirable locations for a Cys substitution.

FIG. 3 shows the amino acid sequence of the variable region $V_L$ of the light chain (SEQ ID NO: 2) of the anti-CLTA4 antibody of FIG. 2, annotated to correlate amino acid numbering in SEQ ID NO:2 and in the Kabat system and to mark desirable locations for a Cys substitution.

FIG. 4 shows the amino acid sequence of the variable region $V_H$ of the heavy chain (SEQ ID NO:3) of an anti-CD137 antibody used to illustrate prodrugging concepts disclosed herein, annotated to correlate amino acid numbering in SEQ ID NO:3 and in the Kabat system and to mark desirable locations for a Cys substitution.

FIG. 5 shows the amino acid sequence of the variable region $V_L$ of the light chain (SEQ ID NO: 4) of the anti-CD137 antibody of FIG. 4, annotated to correlate amino acid numbering in SEQ ID NO:4 and in the Kabat system and to mark desirable locations for a Cys substitution.

FIG. 6, FIG. 7, FIG. 8, and FIG. 9 show the MALDI mass spectra of various compounds of this invention.

FIG. 10A and FIG. 10B show Cys substitution sites in the heavy and light chains of an anti-CTLA4 antibody that have greater than 30% exposure and are within 5 (or 10) A of a CDR amino acid, the sites being identified using Kabat numbering.

FIG. 11A, FIG. 11B, FIG. 11C, FIG. 11D, and FIG. 11E show the effect of prodrugging and subsequent removal of the prodrugging group on the binding to activated $CD4^+$ T-cells by an anti-CTLA4 antibody prodrugged at various positions of the heavy or light chains.

FIG. 12A, FIG. 12B, FIG. 13A, and FIG. 13B show the effect of prodrugging and de-prodrugging of a CTLA4 antibody on IL-2 secretion by PBMC cells.

FIG. 14, FIG. 15A, and FIG. 15B show the effect of prodrugging on the activity of a CD137 antibody.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (C1q) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology,* 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')2, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

Unless indicated otherwise—for example by reference to the numbering in a SEQ ID NO: listing—references to the numbering of amino acid positions in an antibody heavy or light chain variable region ($V_H$ or $V_L$) are according to the Kabat system (Kabat et al., "Sequences of proteins of immunological interest, 5th ed., Pub. No. 91-3242, U.S. Dept. Health & Human Services, NIH, Bethesda, Md., 1991, hereinafter "Kabat") and references to the numbering of amino acid positions in an antibody heavy or light chain constant region ($C_{H1}$, $C_{H2}$, $C_{H3}$, or $C_L$) are according to the EU index as set forth in Kabat. See Lazar et al., US 2008/0248028 A1, the disclosure of which is incorporated herein by reference, for examples of such usage. Further, the ImMunoGeneTics Information System (IMGT) provides at its website a table entitled "IMGT Scientific Chart: Correspondence between C Numberings" showing the correspondence between its numbering system, EU numbering, and Kabat numbering for the heavy chain constant region. See, e.g., Lazar et al., US 2008/0248028 A1 (2008).

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.+

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ⌇⌇⌇ transverse to a bond or an asterisk (*) at the end of the bond denotes a covalent attachment site. For instance, a statement that R is

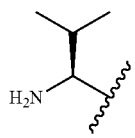

or that R is

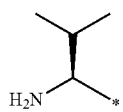

in the formula

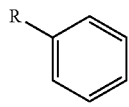

means

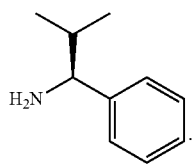

In the formulae of this specification, a bond traversing an aromatic ring between two carbons thereof means that the group attached to the bond may be located at any of the available positions of the aromatic ring. By way of illustration, the formula

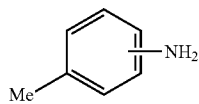

represents

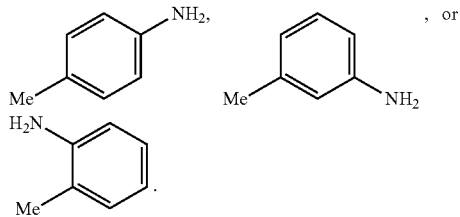

EMBODIMENTS

SEQ ID NO: 1 (where Xaa is Ala) and SEQ ID NO:2 (where Xaa is Ser) provide the full length heavy and light (kappa) chain amino acid sequences, respectively, of a human anti-CTLA4 antibody (hereinafter "CTLA4 Ab") in which Cys substitutions in the V$_H$ or V$_L$ region can be made to illustrate the prodrugging concepts disclosed herein. The variable regions of its heavy and light variable chains are shown in FIG. 2 and FIG. 3, respectively, with annotations correlating the SEQ ID NOs and Kabat numbering of the amino acids and showing desirable positions for Cys substitution. In CTLA4 Ab, the two heavy chains are identical to each other, and the two light chains are identical to each other.

SEQ ID NO:3 and SEQ ID NO:4 provide the full length heavy and light (kappa) chain amino acid sequences, respectively, of an anti-CD137 antibody (hereinafter "CD137 Ab") in which Cys substitutions in the $V_H$ or $V_L$ region can be made to illustrate the prodrugging concepts disclosed herein. The variable regions of its heavy and light variable chains are shown in FIG. 4 and FIG. 5, respectively, with annotations correlating the SEQ ID NOs and Kabat numbering of the amino acids and showing desirable positions for Cys substitution. In CD137 Ab, the two heavy chains are identical to each other, and the two light chains are identical to each other. CD137 Ab is a chimeric antibody, having rat variable heavy and light chain regions and a mouse IgG1 heavy chain constant region.

The prodrugged antibody of this invention can be polyclonal or monoclonal, preferably monoclonal. The prodrugged antibody of this invention can be chimeric, humanized or human, preferably human.

Suitable amino acids in the heavy and light chain variable regions for substitution with a Cys are framework amino acids whose side chains are solvent exposed—preferably at least 30% exposed—so that the substituted-in Cys is accessible for attachment of the blocking moiety BM. It is also important that the substituted-out amino acid is near a CDR amino acid, so that BM can effectively interfere with antibody-antigen binding. A distance of no more than 10 Å is preferred, more preferably no more than 5 Å.

Preferred positions for Cys substitution include positions 23 in the heavy chain variable region and 67 in the light chain variable region, numbering per Kabat. Both positions are in the framework region of the respective variable regions. A Cys can be substituted into these positions by site-specific substitution techniques well known in the art. A substitution at the first site can be referred to, using a shorthand notation, as $V_L$ X67C, where X denotes the substituted-out amino acid. In native antibodies, this site is highly conserved and is often Ser. A substitution at the second site can be similarly referred to as $V_H$ X23C.

A prodrugged antibody of this invention can have either a substitution in the $V_H$ region or in the $V_L$ region, or both. If the antibody has only one of these substitutions, the theoretical maximum number of blocking moiety-linker compounds that can be attached is two, although a prodrugged antibody preparation may assay statistically for a lower number, reflecting chemical inefficiency in the attachment process. If the antibody has both substitutions, the theoretical maximum number is four.

Although the invention has been demonstrated with antibodies of the classic configuration (i.e., two identical heavy chains and two identical light chains), it is also applicable to bispecific antibodies, which have two different pairs of heavy and light chains. Thus, a prodrugged antibody of this invention can be a bispecific antibody in which only one heavy/light chain pair has been prodrugged or one in which both heavy/light chain pairs have been prodrugged.

The substitution of an amino acid in a $V_H$ or $V_L$ region with a Cys, for the purpose of introducing a sulfhydryl side chain amenable to conjugation by maleimide addition chemistry to make an antibody-drug conjugate, is also known. See, for example, Eigenbrot et al. 2007 and Bhakta et al. 2016).

In one embodiment, the antibody capable of being prodrugged and a prodrugged antibody made therefrom and having a Cys at Kabat position 67 of the light chain is an anti-CTLA4 antibody, preferably having (a) a heavy chain CDR1 comprising amino acids 31-35 of SEQ ID NO: 1;

(b) a heavy chain CDR2 comprising amino acids 50-66 of SEQ ID NO: 1;

(c) a heavy chain CDR3 comprising amino acids 99-107 of SEQ ID NO: 1;

(d) a light chain CDR1 comprising amino acids 24-35 of SEQ ID NO:2;

(e) a light chain CDR2 comprising amino acids 51-57 of SEQ ID NO:2; and (f) a light chain CDR3 comprising amino acids 90-98 of SEQ ID NO:2.

More preferably, the anti-CTLA4 antibody has a heavy chain variable region comprising amino acids 1-118 of SEQ ID NO: 1 (where Xaa is Ala) and a light chain variable region comprising amino acids 1-108 of SEQ ID NO:2 (where Xaa is Cys).

In another embodiment, the antibody capable of being prodrugged, and a prodrugged antibody made therefrom and having a Cys at Kabat position 23 of the heavy chain is an anti-CTLA4 antibody, preferably having (a) a heavy chain CDR1 comprising amino acids 31-35 of SEQ ID NO: 1;

(b) a heavy chain CDR2 comprising amino acids 50-66 of SEQ ID NO: 1;

(c) a heavy chain CDR3 comprising amino acids 99-107 of SEQ ID NO: 1;

(d) a light chain CDR1 comprising amino acids 24-35 of SEQ ID NO:2;

(e) a light chain CDR2 comprising amino acids 51-57 of SEQ ID NO:2; and (f) a light chain CDR3 comprising amino acids 90-98 of SEQ ID NO:2.

More preferably, the anti-CTLA4 antibody has a heavy chain variable region comprising amino acids 1-118 of SEQ ID NO: 1 (where Xaa is Cys) and a light chain variable region comprising amino acids 1-108 of SEQ ID NO:2 (where Xaa is Ser).

In one embodiment, the prodruggable anti-CTLA4 antibody and a prodrugged antibody made therefrom, is of the IgG1 isotype. Preferably it has the allotype combination of R214 (EU index numbering; amino acid 215 in SEQ ID NO:1), E356 (EU index numbering; amino acid 357 in SEQ ID NO:1), and M358 (EU index numbering; amino acid 359 in SEQ ID NO: 1), which combination is common in the Caucasian population.

In one embodiment, the linker comprises a polypeptide that is cleavable by—i.e., is a substrate for—an enzyme (a protease) that is uniquely expressed or overexpressed at the diseased tissue or organ, compared to healthy tissue or organ. Preferably, the enzyme is found in the extracellular environment of the diseased tissue or organ. Examples of such proteases include: aspartate proteases (e.g., renin), fibroblast activation protein (FAP), aspartic cathepsins (e.g., cathepsin D, caspase 1, caspase 2, etc.), cysteine cathepsins (e.g., cathepsin B), cysteine proteases (e.g., legumain), disintegrin/metalloproteinases (ADAMs, e.g., ADAM8, ADAM9), disintegrin/metalloproteinases with thrombospondin motifs (ADAMTS, e.g., ADAMTS1), integral membrane serine proteases (e.g., matriptase 2, MT-SP1/matriptase, TMPRSS2, TMPRSS3, TMPRSS4), kallikrein-related peptidases (KLKs, e.g. KLK4, KLK5), matrix metalloproteases (e.g., MMP-1, MMP-2, MMP-9), and serine proteases (e.g., cathepsin A, coagulation factor proteases such as elastase, plasmin, thrombin, PSA, uPA, Factor VIIa, Factor Xa, and HCV NS3/4). Preferably, the protease is fibroblast activation protein (FAP), urokinase-type plasminogen activator (uPA, urokinase), MT-SP1/matriptase, legumain, or a matrix metalloprotease (especially MMP-1, MMP-2, and MMP-9). Those skilled in the art will appreciate that the choice of the enzyme and the corresponding cleavable peptide will depend on the disease to be treated and the protease(s) expressed by the affected tissue or organ.

Examples of polypeptide substrate-enzyme pairs are provided in TABLE I.

TABLE I

POLYPEPTIDE SUBSTRATES AND CLEAVING ENZYMES

| Cleavable Peptide | SEQ ID NO. | Cleaving Enzyme(s) |
|---|---|---|
| LSGRSDNH | 5 | Urokinase, matriptase, legumain |
| VPLSLYS | 6 | Matrix metalloprotease-9 (MMP-9) |
| PLGLAG | 7 | Matrix metalloprotease-2 (MMP-2) |
| VLVPMAMMAS | 8 | Matrix metalloprotease-1 (MMP-1) |
| XXQAR(A/V)X (where X is any amino acid) | 9 | Matriptase (MT-SP1) |
| AGPR | 10 | Matriptase (MT-SP1) |
| AANL | 11 | Legumain |
| PTNL | 12 | Legumain |
| TSGRSANP | 13 | Various |
| DEXXXC(A/S) (where X is any amino acid) | 14 | HCV NS3/4 |
| DLXXXT(A/S) (where X is any amino acid. | 15 | HCV NS3/4 |
| LSGX (where X is R or K) | 16 | Matriptase |

Preferably, the cleavable peptide is LSGRSDNH (SEQ ID NO:5), LSGX (SEQ ID NO: 16) or LSGK (SEQ ID NO: 16).

Disclosures of suitable proteases and/or their substrates include: Desnoyers et al. 2013; Stagliano et al. 2013; Stagliano et al. 2014; Waldmann et al. 2013; Lauermann et al. 2014; Lowman et al. 2014; Daugherty et al. 2015; Lowman et al. 2015a; Lowman et al. 2015b; Moore et al. 2015; West et al. 2016a; Wang et al. 2016; Moore et al. 2016; Moore et al. 2017; and Dennis et al. 2016; the disclosures of which are incorporated herein by reference.

Blocking moieties BM that can be used to interfere with or block activity of a prodrugged antibody with its antigen include: polyethylene glycol (PEG), an albumin binding polypeptide, adnectin, a peptide, and a soluble globular protein such as albumin or fibrinogen.

In one embodiment, BM is PEG having a molecular weight of at least about 2 kDa, with 2 kDa corresponding to PEG with about 45 —(CH$_2$CH$_2$O)— repeating units, and preferably PEG with a molecular weight of at least about 5 kDa, with 5 kDa corresponding to PEG with about 115 —(CH$_2$CH$_2$O)— repeating units.

Amine-terminated PEG with 48 —(CH$_2$CH$_2$O)— repeating units (CAS Reg. No. 32130-27-1) is available from Quanta Biodesign Ltd. Amine-terminated PEG with a nominal molecular weight of 5 kDa is available from NOF America Corp. (CAS Reg. No. 116164-53-5). Using MALDI-TOF-MS analysis, we determined that it has a molecular weight distribution of between about 4.4 kDa and about 6.6 kDa, corresponding to between about 100 and about 155 —(CH$_2$CH$_2$O)— repeating units. Amine-terminated PEG with a nominal molecular weight of 10 kDa is available from NOF America Corp. (CAS Reg. No. also 116164-53-5. Using MALDI-TOF-MS analysis, we determined that it has a molecular weight distribution of between about 9.0 kDa and about 12.0 kDa, corresponding to between about 205 and about 275 —(CH$_2$CH$_2$O)— repeating units. The terminal amine group provides a chemical functionality for attachment to the linker moiety.

Disclosures of these and other blocking moieties BM include: Tomasi et al. 1988; Trouet et al. 2004; Waldmann et al. 2014; Lauermann et al. 2014; Lowman et al. 2014; Daugherty et al. 2015; Lowman et al. 2015a; West et al. 2016a; and Wang et al. 2016; the disclosures of which are incorporated herein by reference.

An antibody having a Cys as described hereinabove can be conjugated to a blocking moiety-linker moiety compound having a maleimide terminal group by Michael addition of the Cys sulfhydryl (SH), as shown below. The procedures for such conjugation are well known in the art; see, for example, Shepard et al., WO 2017/112624 A1 (2017).

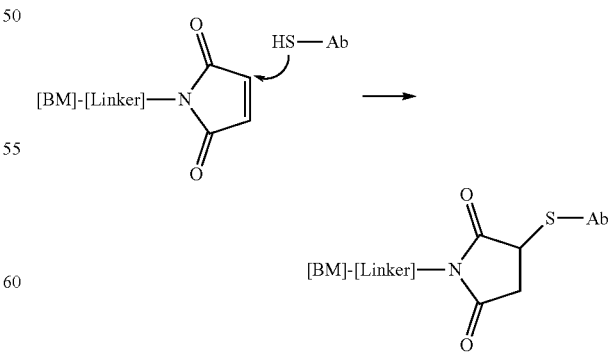

Examples of maleimide terminated blocking moiety-linker compounds that can be so used to prodrug an antibody include ones according to formulae (Ia)-(Ih), each of which comprises a peptide cleavable by the enzyme matriptase.

(Ia)
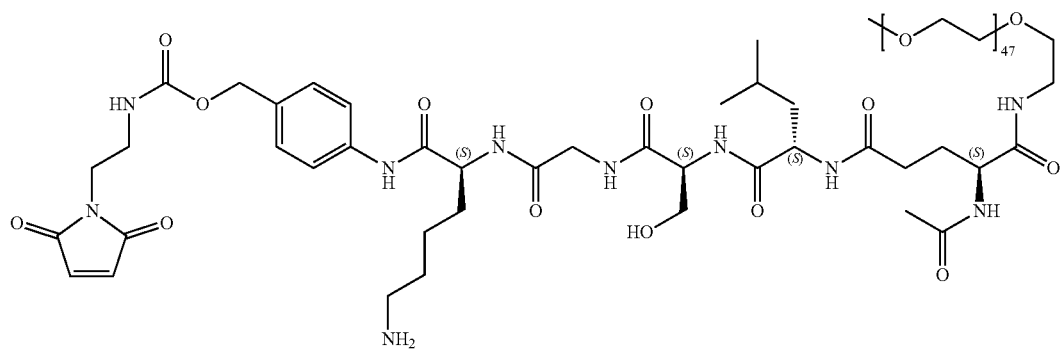
(Ib)
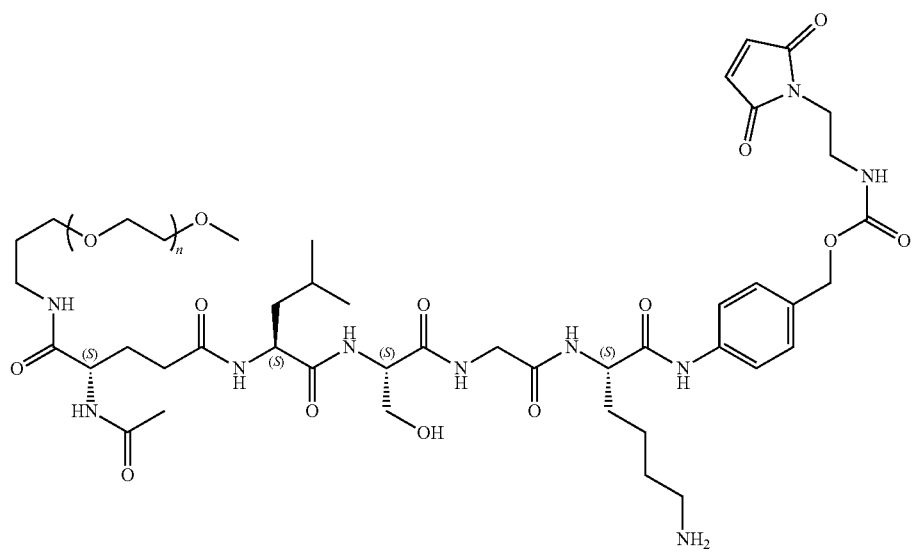
n = 100-155
(Ic)
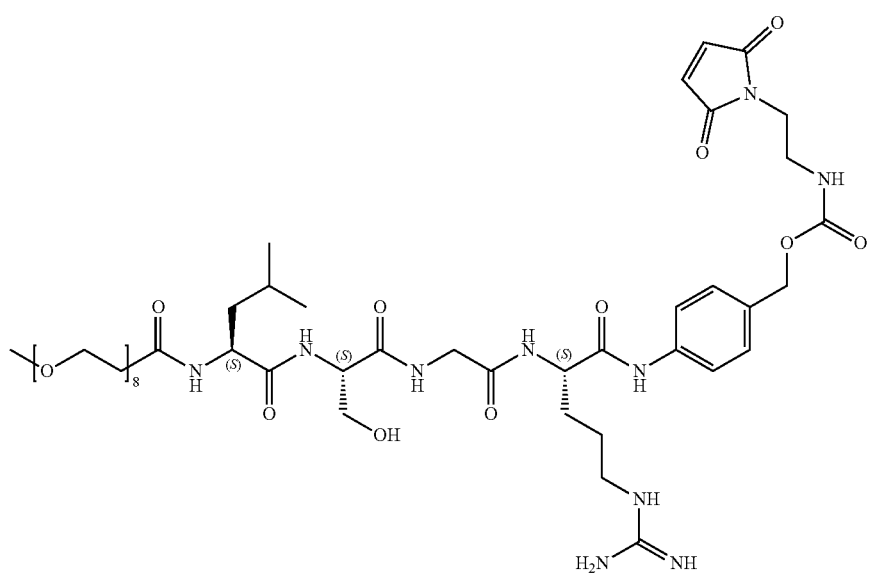

(Id)
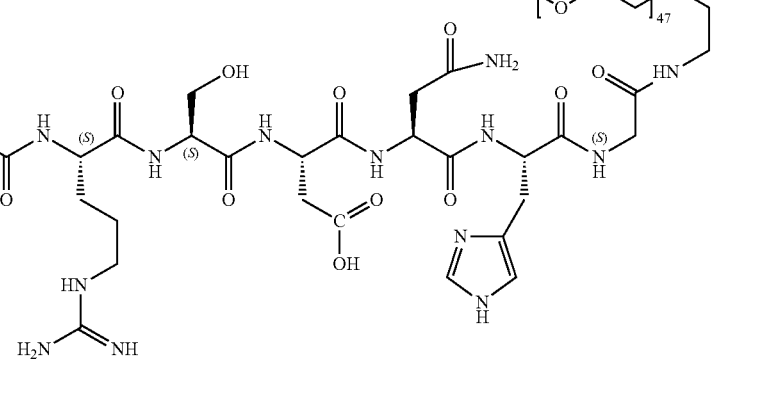
(Ie)
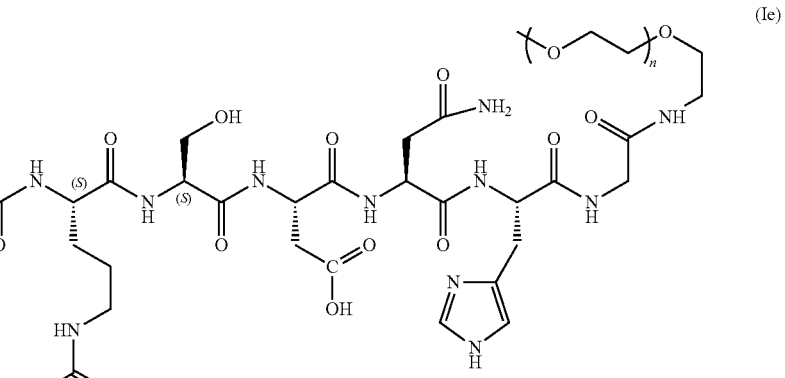
n = 100-155
(If)
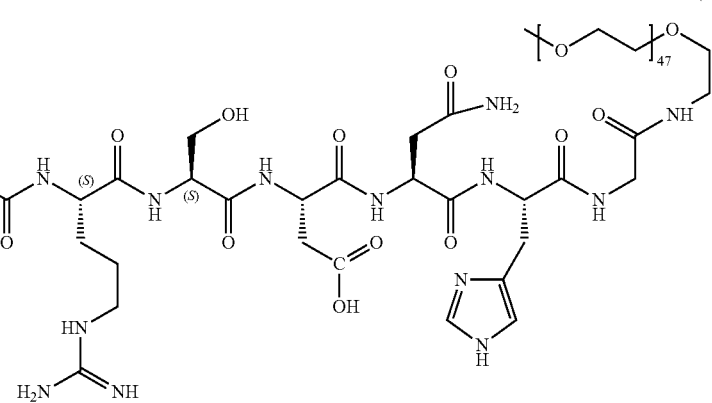

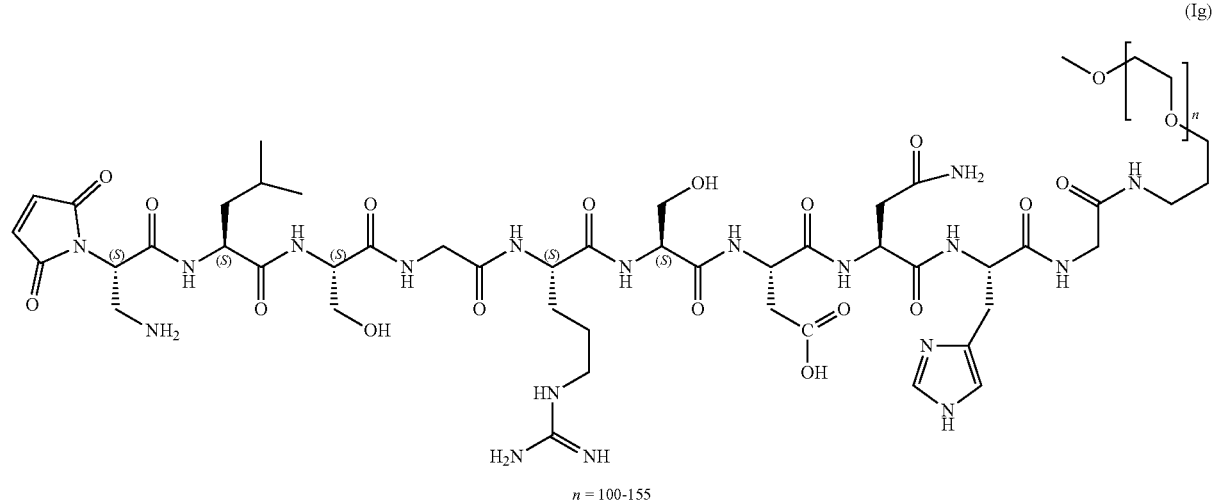
(Ig)
n = 100-155
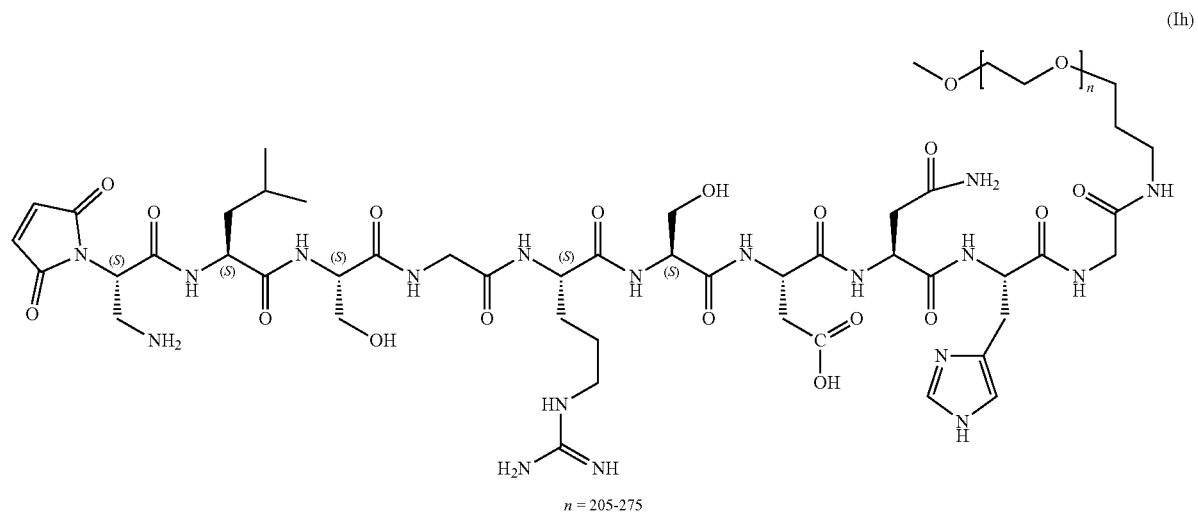
(Ih)
n = 205-275
Conjugation of an antibody with the foregoing blocking moiety-linker compounds (Ia)-(Ih) provides prodrugged antibodies according to the formulae (IIa)-(IIh), respectively, where Ab is an antibody as defined above and m is 1, 2, 3, or 4.
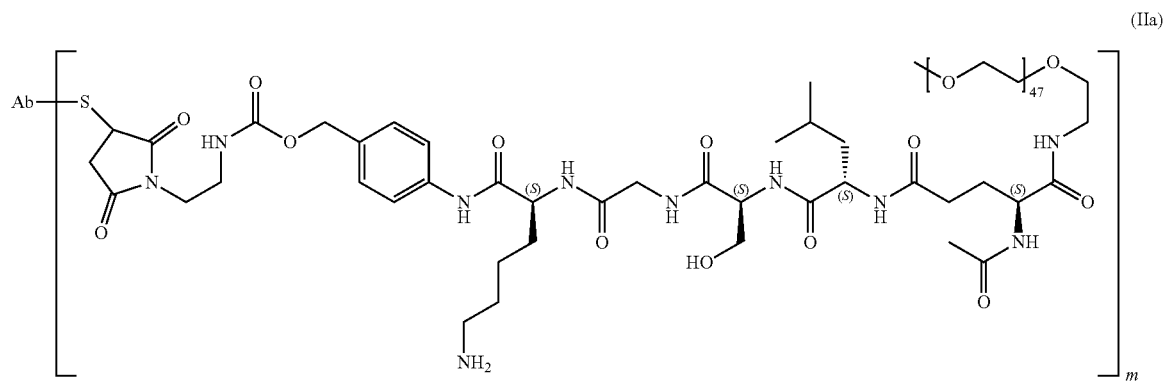
(IIa)

-continued
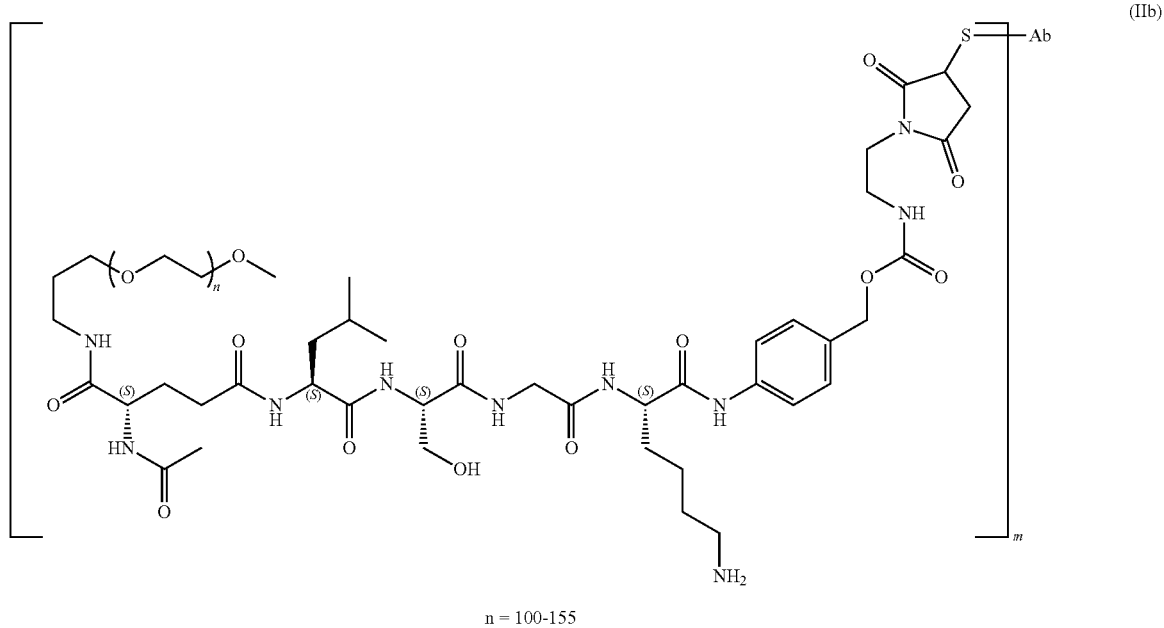
(IIb)
n = 100-155
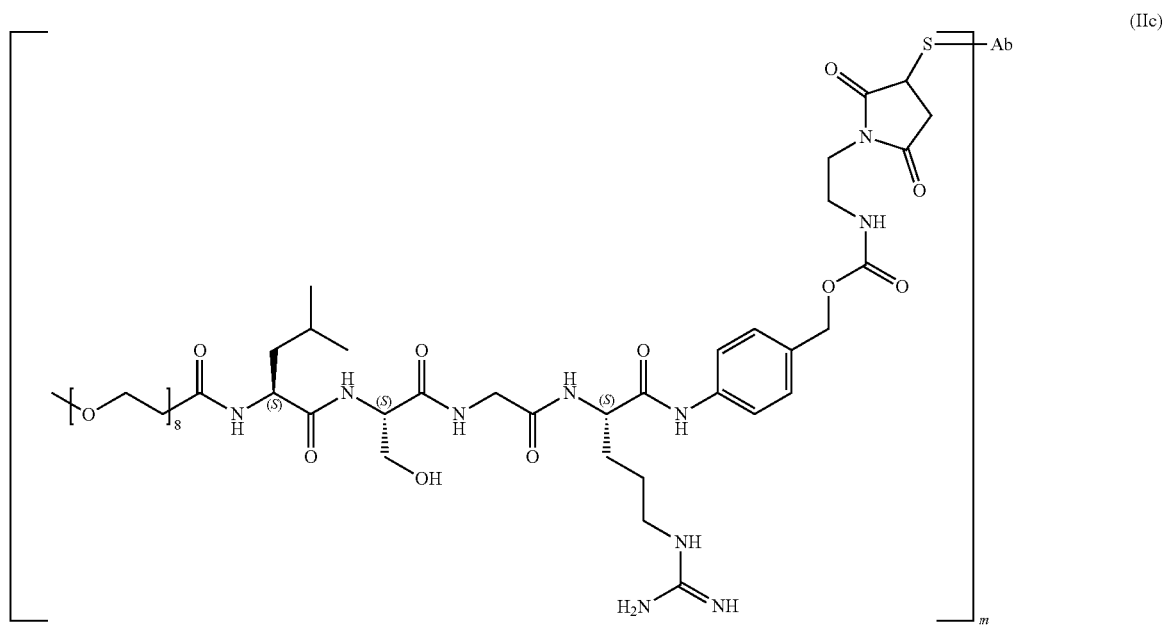
(IIc)
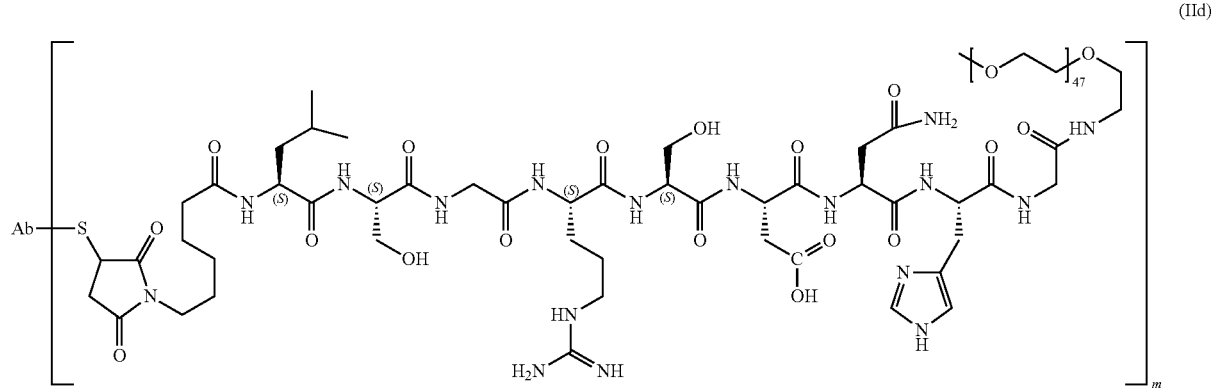
(IId)

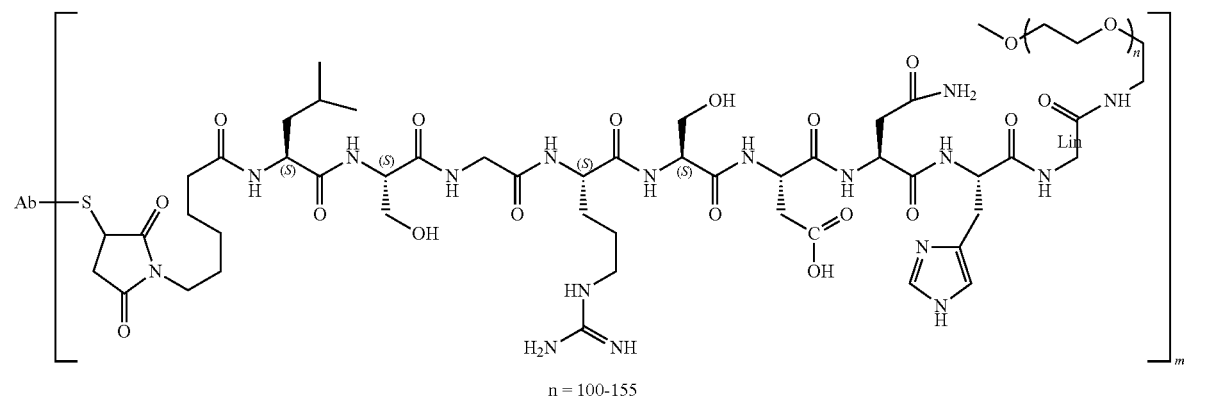
(IIe)
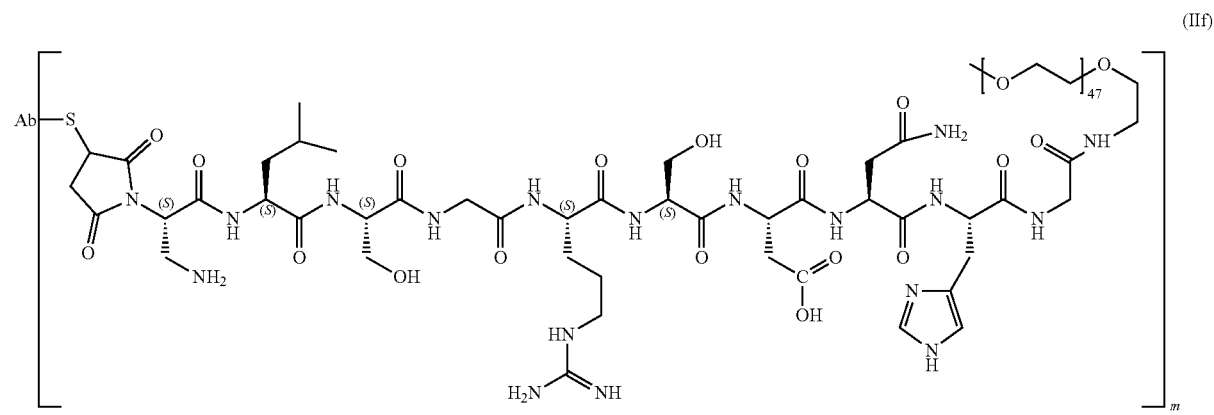
(IIf)
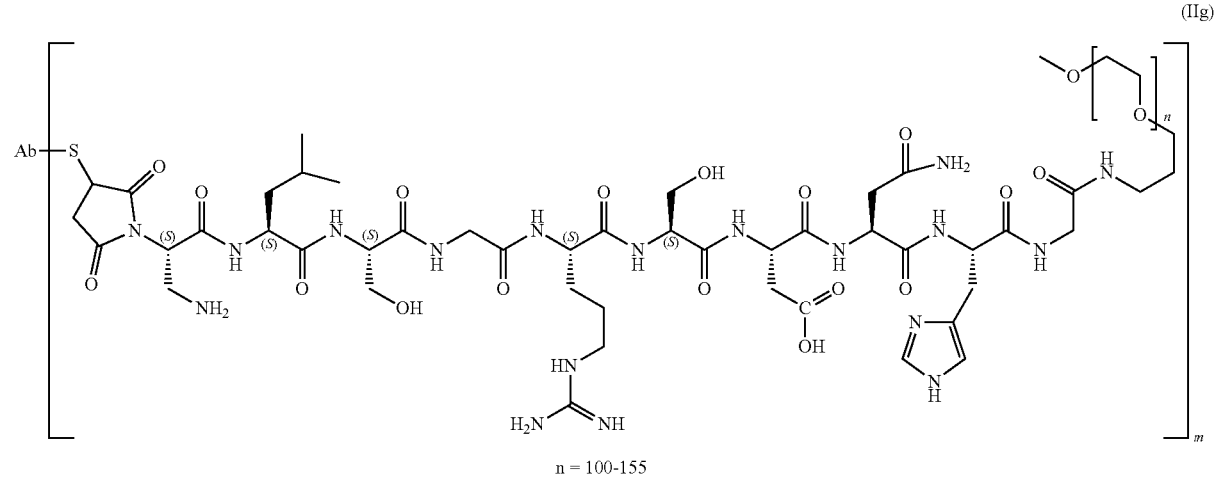
(IIg)

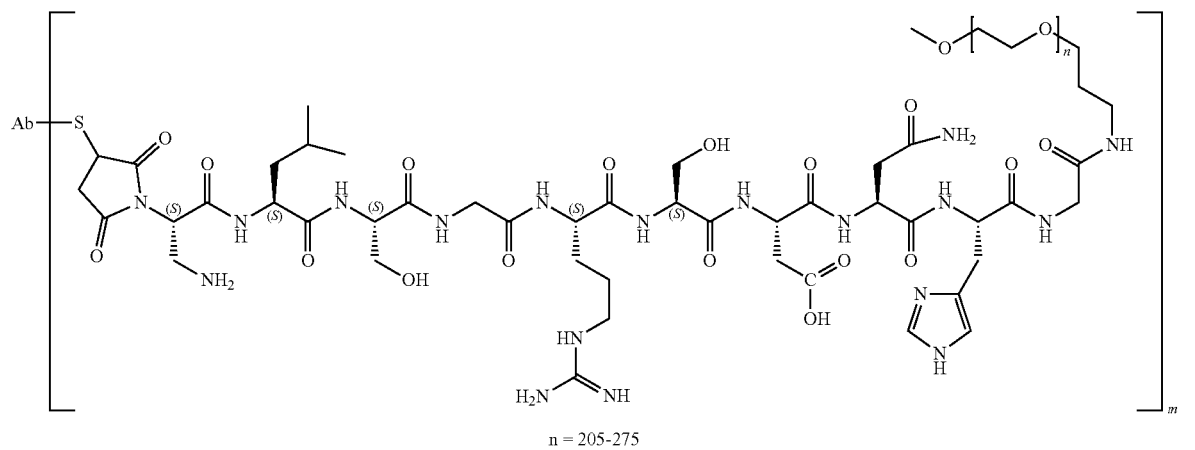

n = 205-275

Those skilled in the art will appreciate that, over time, the initially formed succinimide structure resulting from thiol addition to the maleimide group may hydrolytically ring-open to a seco form, and that the succinimide and seco forms are functionally equivalent.

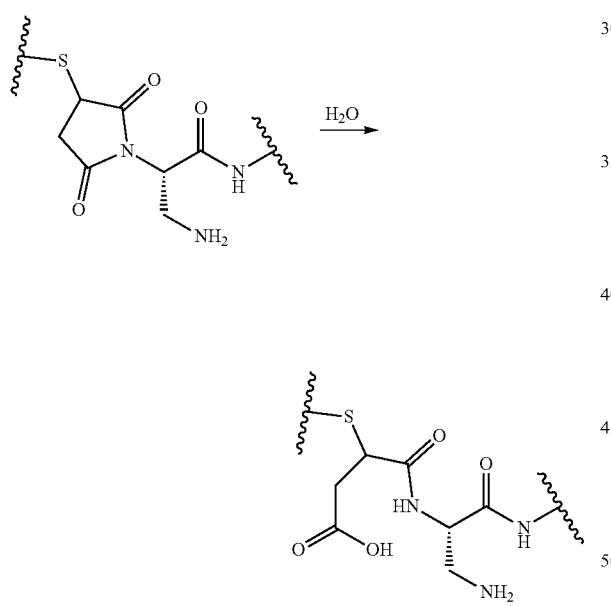

As can be discerned from some of the structures above, the enzymatically cleavable peptide can be used in combination with a self-immolating group. Briefly, the function of a self-immolating group is to provide separation between the peptide and other portions of the antibody, the linker, or the blocking moiety, lest any of them interfere with the action of the cleaving enzyme. After cleavage occurs, the self-immolating group undergoes a self-elimination reaction. Uses and structures of self-immolating groups are described in Zhang et al., U.S. Pat. No. 9,527,871 B2 (2016), the disclosure of which is incorporated herein by reference.

A preferred self-immolating group is a p-aminobenzyl oxycarbonyl (PABC) group, whose structure is shown below.

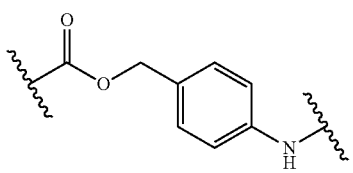 [SMILES: *Nc1ccc(COC(*)=O)cc1]

Its mode of action is illustrated in the reaction sequence below:

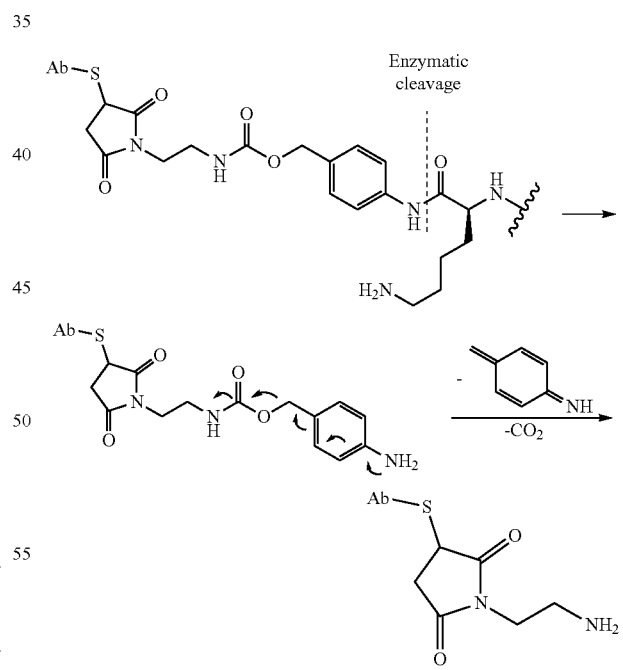

As can be seen from the above reaction sequence, cleavage of the peptide does not restore the antibody Ab to its original structure in the sense that the Cys bonding to the blocking moiety-linker is left with a succinimide residue (or its ring-opened derivative) attached thereto. This applies regardless of whether a self-immolating group was used or not. We have discovered that, unexpectedly, the succinimide residue does not prevent the restoration of the antibody's antigen binding activity.

EXAMPLES

The practice of this invention can be further understood by reference to the following examples, which are provided by way of illustration and not of limitation.

Example 1—Compound (Ia)

A linear precursor was prepared using standard Fmoc chemistry using a Protein Technologies' PRELUDE™ peptide synthesizer.

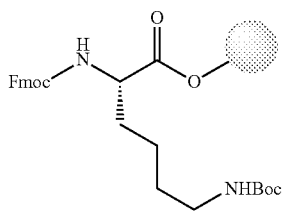

1

Resin Loading:
Fmoc-L-Lys(Boc)-OH (3.34 mmol, 1.567 g) and diisopropylethyl amine (DIPEA, 8.36 mmol, 1.457 mL) in dichloromethane (DCM, 18.58 mL) was added to 2-chlorotrityl resin (1.5 mmol/g, 2.79 mmol, 1.81 g, pre-swelled with DCM) in a Biorad preparative column. The resin was shaken at room temperature (RT) for 18 h. The solvent was removed by filtration, and the solid resin was washed with DCM (5×10 mL) and then dried under vacuum to provide resin 1 (2.713 g, loading 0.81 mmol/g).

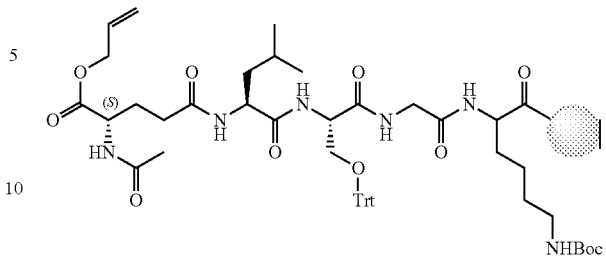

2

Standard Amino Acid Couplings on PRELUDE™ Apparatus:
The resin was swelled with DMF via the Top Wash function (8 mL×10 min) and mixed with a gentle stream of $N_2$ every 30 seconds. The solvent was drained and the resin was washed with a solution of 20% piperidine in N,N-dimethylformamide (DMF, 10 mL×2 over 5 minutes per wash) and mixed with a gentle stream of $N_2$ every 30 seconds. The resin was washed with DMF (15 mL×6 over 60 seconds per wash). The Fmoc protected amino acid was added to the resin (Fmoc-AA, 0.1 M solution in DMF, 3 equiv), followed by HATU (0.2M solution in DMF, 3 equiv.) and N-methyl morpholine (0.8 M in DMF, 5 equiv.). The reaction mixture was then agitated by a gentle stream of nitrogen for 60 min.

This standard procedure was used for P4-P1 couplings. After coupling of final P1 amino acid and following the removal of the Fmoc group, the resin was capped with a solution of acetic anhydride/DIPEA/DMF (1:1:3, 5 mL×2 over 10 min). Resin—Fmoc-L-Lys(Boc)-OH (P5)—Fmoc-L-Gly-OH (P4)—Fmoc-L-Ser (Trityl)-OH (P3)—Fmoc-Leu-OH (P2)—Fmoc-Glu-OAll (P1)

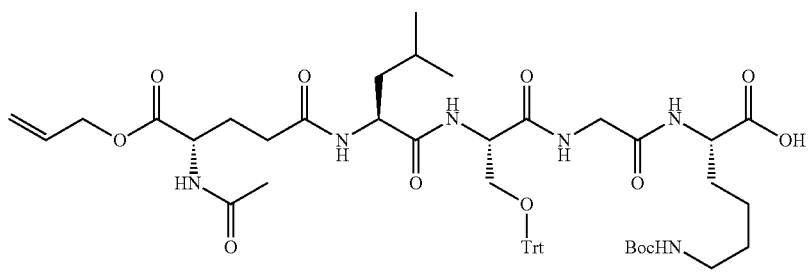

3

Compound 3.
Resin 2 (0.956 g, 1.0 mmol) was treated with a mixture of DCM (16 ml) and 1,1,1,3,3,3-hexafluoro-2-propanol (HFP, 4 ml) and shaken at RT for 10 min. The mixture was filtered, and the filtrate was concentrated in vacuo. The resin was treated with additional DCM (16 ml) and HFP (4 mL) and shaken for 10 min. The mixture was filtered. The combined filtrates were concentrated in vacuo. This material was taken up in DCM and concentrated in vacuo (4×) to provide $N^2$—N—(((S)-4-acetamido-5-(allyloxy)-5-oxopentanoyl)-L-leucyl)-O-trityl-L-serylglycyl-$N^6$-(tert-butoxycarbonyl)-L-lysine. MS(ESI$^+$) (M+H)$^+$ 957.8

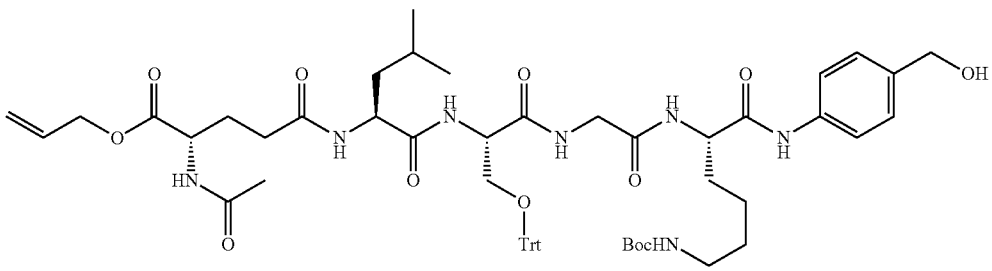

4

Compound 4.

To a solution of peptide 3 in DMF (2.5 ml) was added 2,4,6-collidine (198 µl, 1.5 mmol), followed by (4-aminophenyl)methanol (148 mg, 1.2 mmol) and HATU (456 mg, 1.2 mmol). The clear orange solution was stirred at RT for 20 min. The reaction was then added to a stirred flask of $H_2O$ (50 mL) and the resulting precipitate was collected by vacuum filtration (washed with 3×10 mL $H_2O$). After air drying on a frit, the solids were washed with $Et_2O$ (3×10 mL). The solids then were dissolved in a mixture of DCM and MeOH (total~100 mL), dried over $Na_2SO_4$, filtered, and concentrated in vacuo to provide allyl $N^2$-acetyl-$N^5$—((S)-1-(((S)-1-((2-(((S)-6-((tert-butoxycarbonyl)amino)-1-((4-(hydroxymethyl)phenyl)amino)-1-oxohexan-2-yl)amino)-2-oxoethyl)amino)-1-oxo-3-(trityloxy)propan-2-yl)amino)-4-methyl-1-oxopentan-2-yl)-L-glutaminate (785 mg, 0.739 mmol, 73.9% yield) as a brown solid. MS(ESI$^+$) m/z 1061.8 (M+H)$^+$.

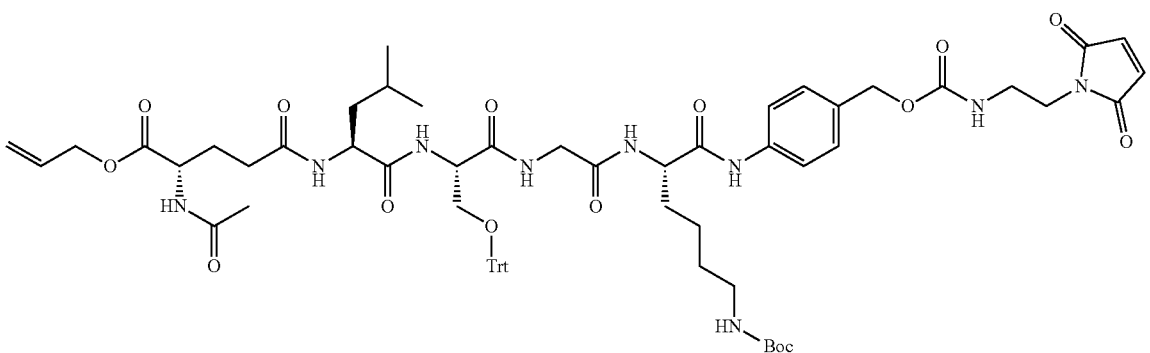

5

Compound 5.

To a solution of intermediate 4 (785 mg, 0.739 mmol) in DMF (3695 µl) was added bis(4-nitrophenyl) carbonate (337 mg, 1.108 mmol) and DIPEA (193 µl, 1.108 mmol). The reaction was stirred at RT for 1.5 h. To the mixture was then added 1-(2-aminoethyl)-1H-pyrrole-2,5-dione hydrochloride (261 mg, 1.478 mmol) and DIPEA (386 µL, 2.217 mmol). The resulting solution was stirred at RT for 30 min before it was added to $Et_2O$ (50 mL). The resulting precipitate was collected by vacuum filtration, washing with $Et_2O$ (2×5 mL), to provide allyl $N^2$-acetyl-$N^5$—((S)-1-(((S)-1-((2-(((S)-6-((tert-butoxycarbonyl)amino)-1-((4-((((2-(2,5-dioxo-2,5-dihydro-1H-pyrrol-1-yl)ethyl)carbamoyl)oxy)methyl)phenyl)amino)-1-oxohexan-2-yl)amino)-2-oxoethyl)amino)-1-oxo-3-(trityloxy)propan-2-yl)amino)-4-methyl-1-oxopentan-2-yl)-L-glutaminate (1.1 g). MS(ESI$^+$) m/z 1228.7 (M+H)$^+$.

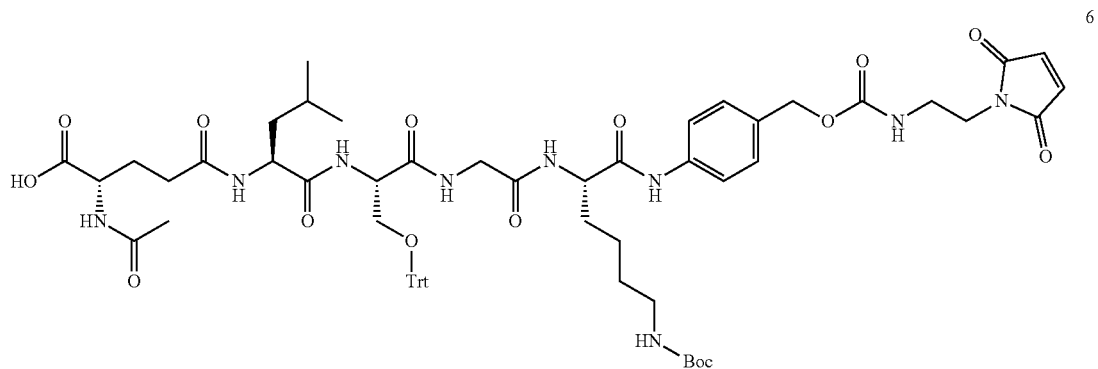

6

Compound 6.

To a degassed solution of intermediate 5 (938 mg, 0.764 mmol) in a mixture of MeCN (6109 µl) and H$_2$O (1527 µl) was added acetic acid (218 µl, 3.82 mmol) and 4-methylmorpholine (337 µl, 3.05 mmol), followed by palladium(II) acetate (86 mg, 0.382 mmol) and triphenylphosphine-3,3′,3″-trisulfonic acid trisodium salt (434 mg, 0.764 mmol). The reaction was stirred at RT for 16 h. The reaction was filtered and purified by reverse phase flash chromatography (50 g RediSep Gold C18 column; linear gradient 20-100% B-A over 24 min; A=5% MeCN—H$_2$O w/0.05% v/v TFA; B=5% H$_2$O-MeCN w/0.05% v/v TFA) to provide N$^2$-acetyl-N$^5$—((S)-1-(((S)-1-((2-(((S)-6-((tert-butoxycarbonyl)amino)-1-((4-(((2-(2,5-dioxo-2,5-dihydro-1H-pyrrol-1-yl)ethyl)carbamoyl)oxy)methyl)phenyl)amino)-1-oxohexan-2-yl)amino)-2-oxoethyl)amino)-1-oxo-3-(trityloxy)propan-2-yl)amino)-4-methyl-1-oxopentan-2-yl)-L-glutamine (286 mg). MS(ESI$^+$) m/z 1187.6 (M+H)$^+$.

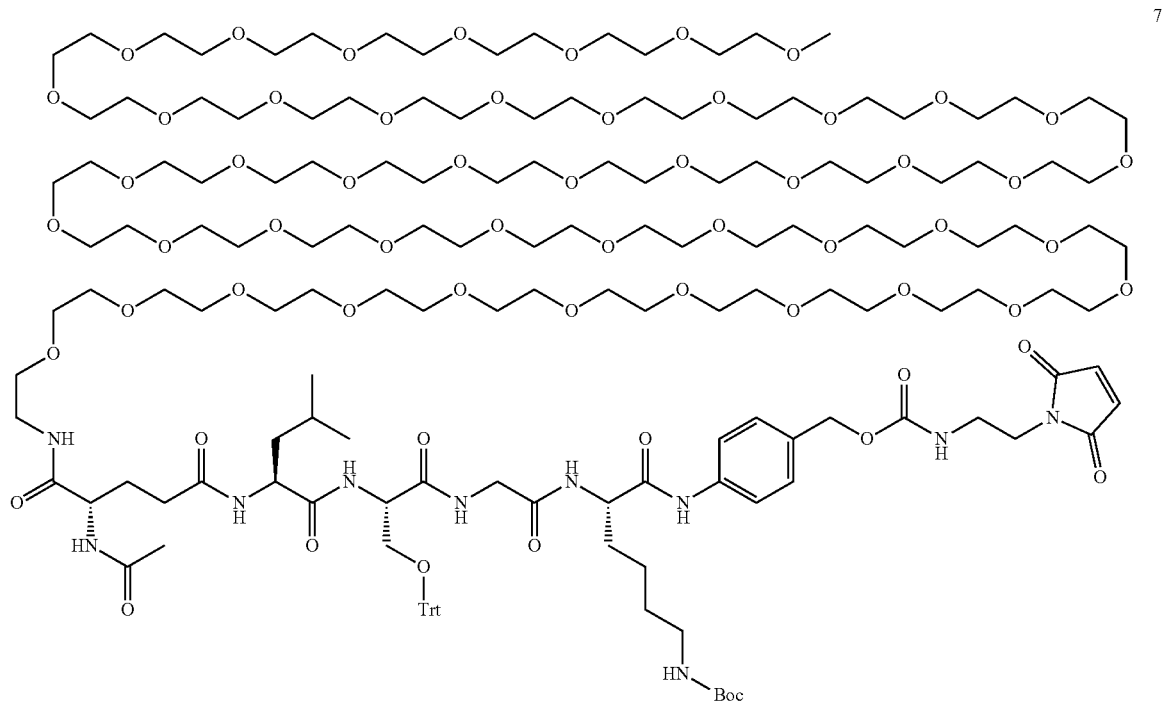

7

Compound 7.

To a solution of intermediate 6 (286 mg, 0.241 mmol) in DMF (3008 µl) was added HATU (101 mg, 0.265 mmol), followed by m-dPEG48-amine (Quanta Biodesign, CAS #32130-271, 568 mg, 0.265 mmol) and DIPEA (84 µl, 0.481 mmol). The reaction was stirred at RT for 30 min. Purification by reverse phase flash chromatography (50 g RediSep Gold C18 column; linear gradient 10-100% B-A; A=5% MeCN—H$_2$O with 0.05% v/v TFA; B=95% MeCN—H$_2$O with 0.05% v/v TFA) provided compound 7 (509 mg).

(Ia)

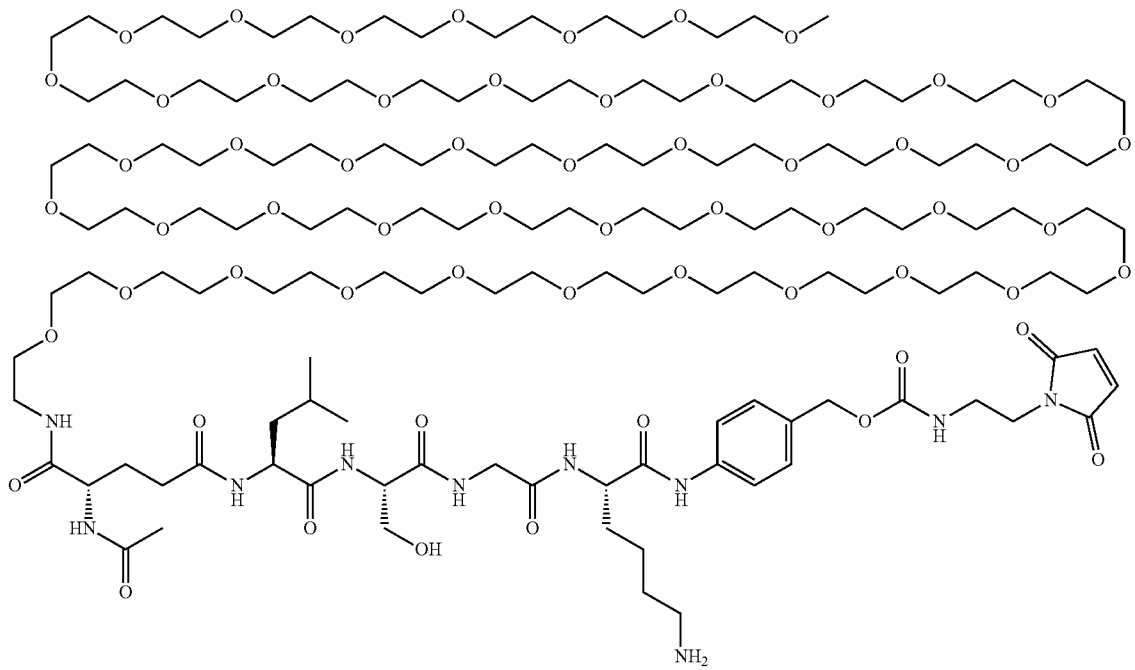

Compound (Ia).

To a solution of compound 7 (150 mg, 0.045 mmol) in DCM (724 μl) was added TFA (181 μl), followed by triisopropylsilane (13.94 μl, 0.068 mmol). The reaction was stirred at RT for 1.5 h. The reaction was then concentrated and purified by preparative HPLC (Phenomenex Luna C18 30×100 mm column; linear gradient 10-90% B-A over 25 min; A=5% MeCN—H$_2$O with 0.1% v/v TFA; B=95% MeCN—H$_2$O with 0.1% v/v TFA; 30 mL/min; 254 nm detection) to provide compound (Ia) (86 mg) as white solid. MS(ESI$^+$) m/z 991.2 (M/3+H)$^+$.

Example 2—Compound (Ib)

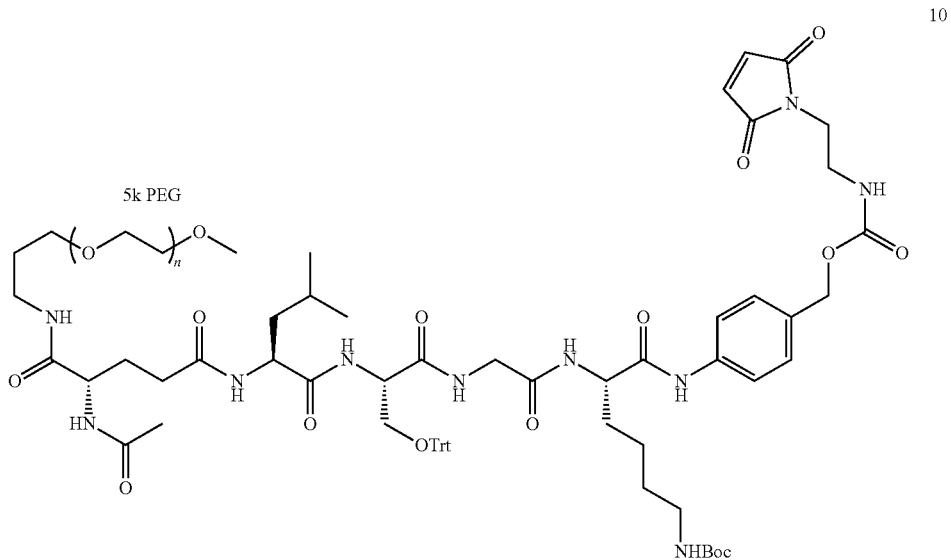

Compound 10.

To a solution of intermediate 6 (20 mg, 0.017 mmol) in DMF (400 μl) was added HATU (8.32 mg, 0.022 mmol). The mixture was stirred at RT for 5 min before a solution of methoxy-PEG-(CH$_2$)$_3$—NH$_2$ (NOF, catalog #SUN-BRIGHT® MEPA-50H, CAS #: 116164-53-5, 168 mg, 0.034 mmol) in DMF (400 μl) was added. The mixture was then stirred at RT for 7 h before it was diluted in MeOH and purified by preparative HPLC (Phenomenex Luna C18 30×100 mm column; linear gradient 5-80% B-A over 25 min; A=5% MeCN—H$_2$O with 0.1% v/v TFA; B=95% MeCN—H$_2$O with 0.1% v/v TFA; 30 mL/min; 220 nm detection) to provide compound 10 (39.1 mg, 6.34 μmol, 37.6% yield).

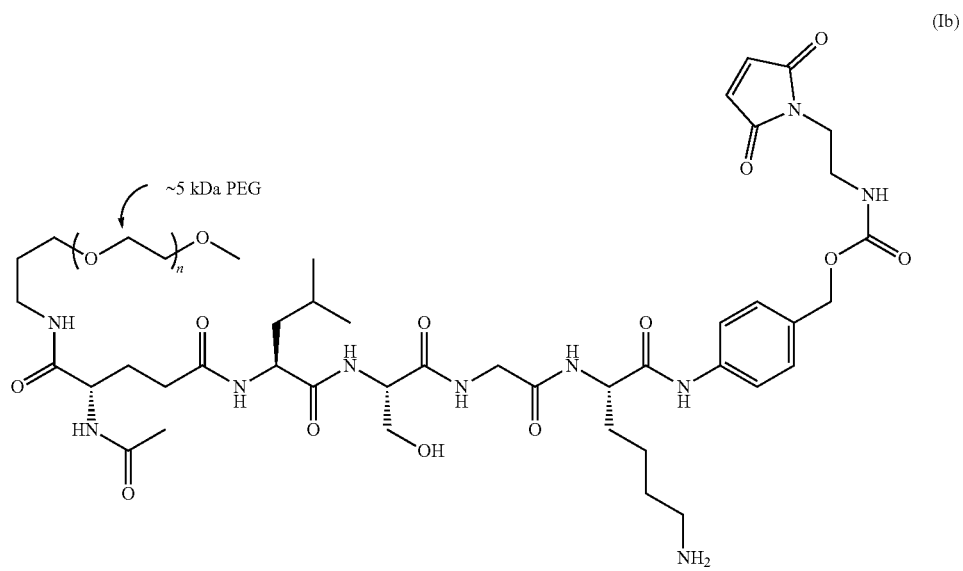

(Ib)

Compound (Ib).

To a solution of compound 10 (39.1 mg, 5.83 μmol) in acetonitrile (0.1 mL) was added 20% TFA in DCM (0.5 mL). The reaction was then stirred at RT for 1 h before it was concentrated in vacuo. Purification by preparative HPLC (Phenomenex Luna C18 30×100 mm column; linear gradient 0-80% B-A over 25 min; A=5% MeCN—H$_2$O with 0.1% v/v TFA; B=95% MeCN—H$_2$O with 0.1% v/v TFA; 30 mL/min; 220 nm detection) to provide compound (Ib) (13.5 mg). MALDI mass spectral showed correct modification of the 5 k PEG compound, with a Δ MS of 828 (FIG. 6).

Example 3—Compound (Ic)

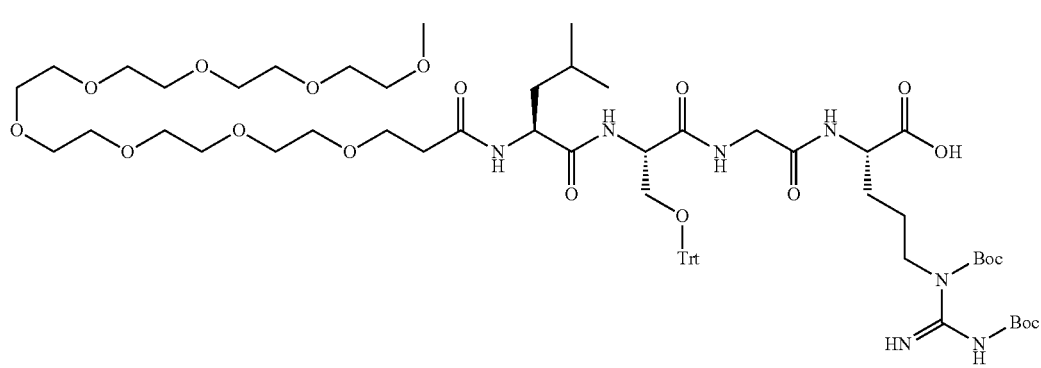

11

Peptide 11 was prepared using standard Fmoc chemistry on the Protein Technologies' Prelude peptide synthesizer following chemistry analogous to that used to prepare intermediate 3. Resin—Fmoc-L-Arg(Boc)$_2$-OH (P5)—Fmoc-L-Gly-OH (P4)—Fmoc-L-Ser (Trityl)-OH (P3) —Fmoc-Leu-OH (P2)—m-dPEG8-acid (Quanta Biodesign, CAS #1093647-41-6) (P1). MS(ESI$^+$) m/z 1269.6 (M+H)$^+$.

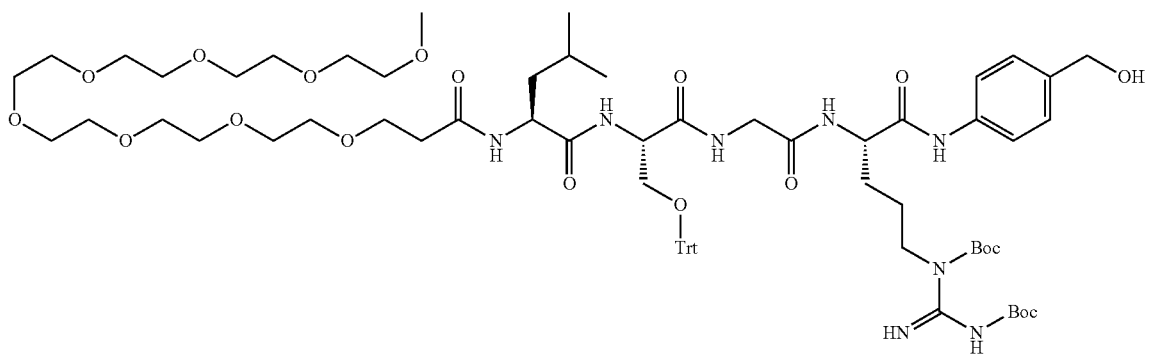

12

Compound 12.

To a solution of intermediate 11 (89 mg, 0.07 mmol) in DMF (175 µl) was added (4-aminophenyl)methanol (10.35 mg, 0.084 mmol), followed by HATU (31.9 mg, 0.084 mmol) and 2,4,6-collidine (13.88 µl, 0.105 mmol). The clear orange solution was stirred at RT for 30 min and was added to a stirred vial of H$_2$O (4 mL). The resulting precipitate was collected by vacuum filtration (washed with 2×1 mL H$_2$O). After air drying on the frit, the solids were washed with Et$_2$O (3×5 mL). The solids were dried under vacuum to provide compound 12 (69 mg, 72%). MS(ESI$^+$) m/z 1372.6 (M+H)$^+$.

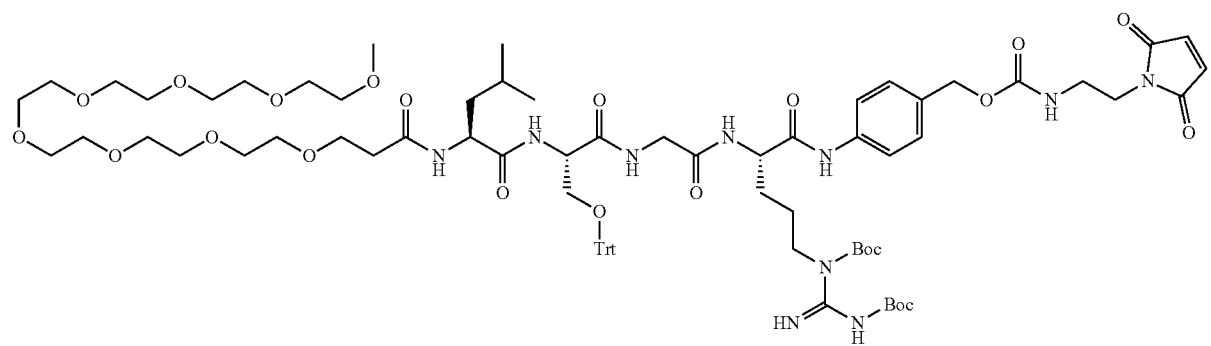

13

Compound 13.

To a solution of intermediate 12 (69 mg, 0.050 mmol) in DMF (251 µl) was added bis(4-nitrophenyl) carbonate (22.92 mg, 0.075 mmol) and DIPEA (13.12 µl, 0.075 mmol). The reaction was stirred at RT for 1 h before 1-(2-aminoethyl)-1H-pyrrole-2,5-dione hydrochloride (17.74 mg, 0.100 mmol) and DIPEA (26.2 µl, 0.151 mmol) was added. The resulting mixture was stirred at RT for an additional 1 h and was then added, dropwise, to a vial of Et$_2$O (15 mL). The resulting precipitate was collected by vacuum filtration, washed with Et$_2$O (3×3 mL), and dried under vacuum to provide compound 13 (60 mg, 78%). MS(ESI$^+$) m/z 1539.8 (M+H)$^+$.

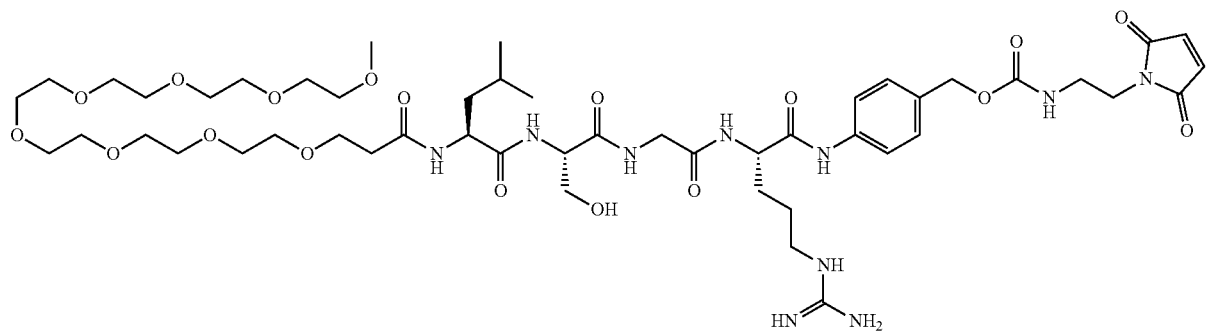

(Ic)

Compound (Ic).

To a solution of intermediate 13 (60 mg, 0.039 mmol) in DCM (273 μl) was added TFA (117 μl), followed by triisopropylsilane (16.01 μl, 0.078 mmol). The reaction was stirred at RT for 2 h before it was concentrated in vacuo. The crude material was purified by preparative HPLC (Phenomenex Luna C18 30×100 mm column; linear gradient 10-90% B-A over 20 min; A=5% MeCN—H$_2$O with 0.1% v/v TFA; B=95% MeCN—H$_2$O with 0.1% v/v TFA; 30 mL/min; 254 nm detection) to provide compound (Ic) (4.2 mg, 8.9% yield) as a white solid. MS(ESI$^+$) m/z 1096.9 (M+H)$^+$.

Example 4—Compound (Id)

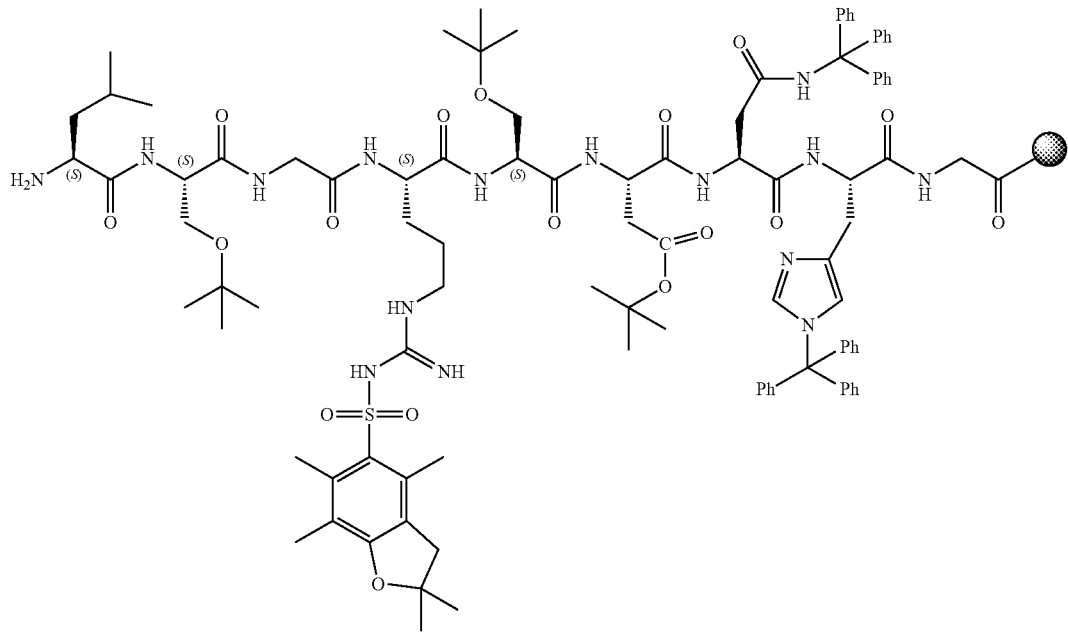

17

Resin 17 was prepared using standard Fmoc chemistry on the Protein Technologies' PRELUDE™ peptide synthesizer following analogous chemistry described for resin 2 from the appropriate starting materials. Resin—Fmoc-L-Gly-OH (P9)—Fmoc-L-His(Trityl)-OH (P8)—Fmoc-L-Asn(trityl)-OH(P7)—Fmoc-L-Asp(tBu)-OH (P6)—Fmoc-L-Ser(tBu)-OH (P5)—Fmoc-L-Arg(Pbf)-OH (P4)—Fmoc-L-Gly-OH (P3)—Fmoc-L-Ser (tBu)-OH (P2)—Fmoc-Leu-OH (P1).

18

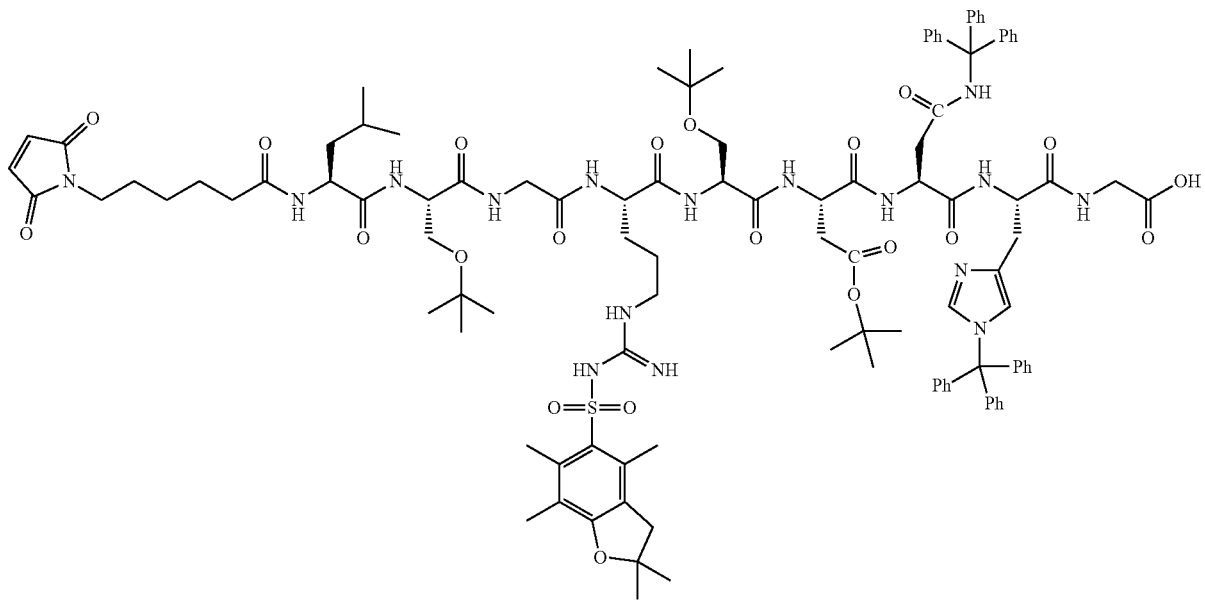

Compound 18.

To resin 17 (158 mg, 0.75 mmol/g) was added a solution of 6-maleimidocaproic acid (47.0 mg, 0.222 mmol) and HATU (52.0 mg, 0.137 mmol) in DMF (0.5 mL), followed by 2,4,6-collidine (0.392 mL, 0.359 mmol). The resulting mixture was shaken for 2 h before the solvent was drained. The resin washed with DMF (6 mL×3) and DCM (6 mL×2) and was then treated with 20% HFP in DCM (8 mL) for 15 min. The mixture was filtered and the filtrate was concentrated in vacuo to provide $N^{\alpha}$—($N^2$—((S)-4-(tert-butoxy)-2-((S)-3-(tert-butoxy)-2-((S)-2-(2-((S)-3-(tert-butoxy)-2-((S)-2-(6-(2,5-dioxo-2,5-dihydro-1H-pyrrol-1-yl)hexanamido)-4-methylpentanamido)propanamido)acetamido)-5-(3-((2,2,4,6,7-pentamethyl-2,3-dihydrobenzofuran-5-yl)sulfonyl)guanidino)pentanamido)propanamido)-4-oxobutanoyl)-$N^4$-trityl-L-asparaginyl)-$N^t$-trityl-L-histidylglycine (33.8 mg, 19.37% yield).

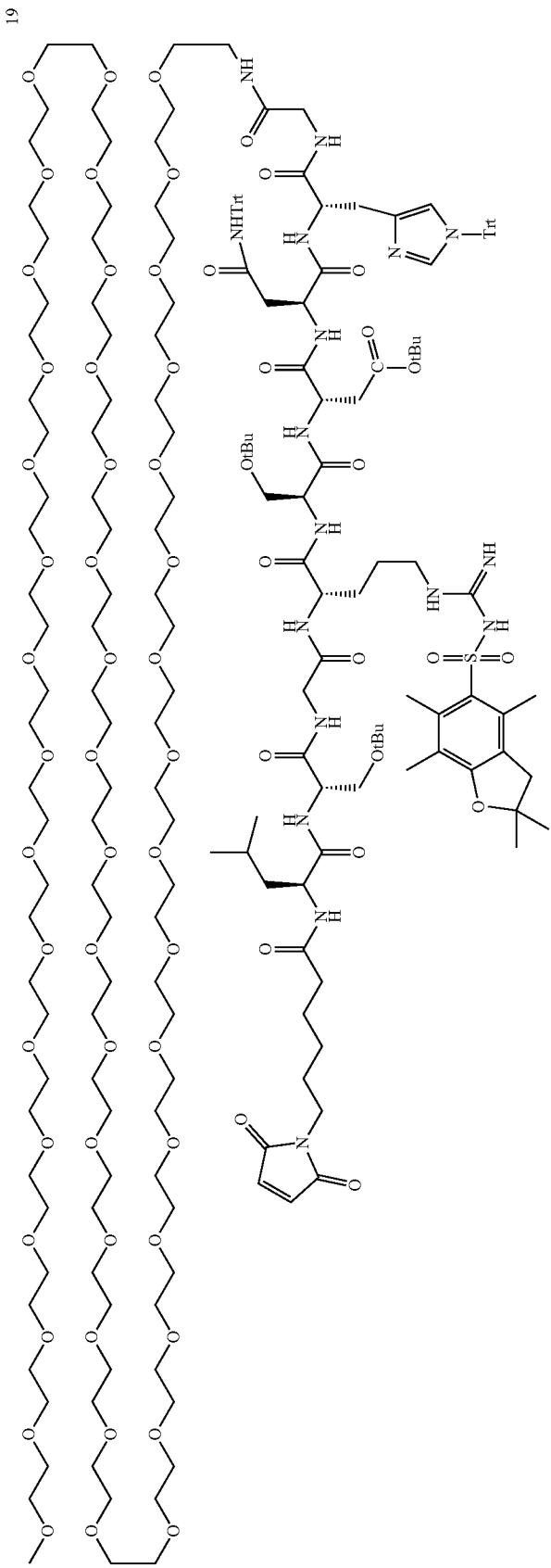

Compound 19.

To a solution of intermediate 18 (38.3 mg, 0.019 mmol) in DMF (200 µl) was added HATU (10.71 mg, 0.028 mmol). The mixture was stirred at RT for 10 min before m-dPEG48-amine (72.5 mg, 0.034 mmol) and DIPEA (3.28 µl, 0.019 mmol) was added. The reaction was stirred at RT for additional 10 min and was then purified by preparative HPLC (Phenomenex Luna C18 30×100 mm column; linear gradient 25-100% B-A over 15 min; A=5% MeCN—H$_2$O with 0.1% v/v TFA; B=95% MeCN—H$_2$O with 0.1% v/v TFA; 30 mL/min; 220 nm detection) to provide compound 19 as a white solid. MS(ESI$^+$) m/z 1389.0 (M/3+H)$^+$. (14 mg, 17.9% yield).

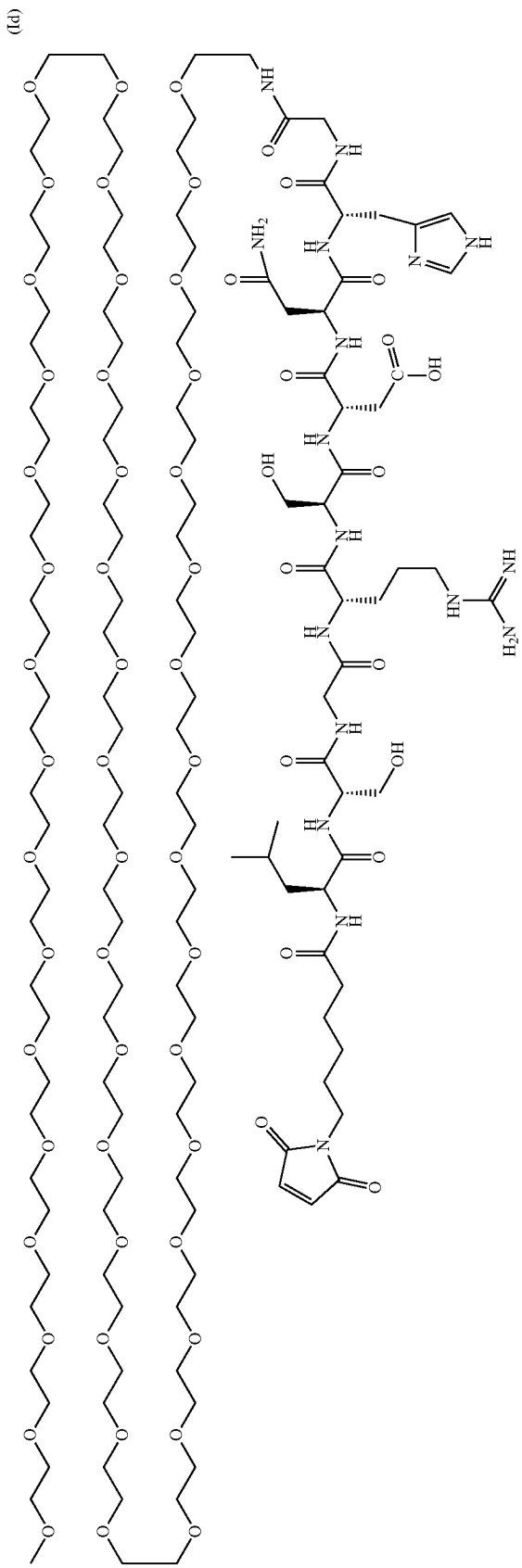

Compound (Id).

To a vial was added intermediate 19 (14 mg, 3.36 µmol) followed by TFA (50 µL, 0.649 mmol). The reaction was stirred at RT for 30 min before it was diluted with acetonitrile and purified by preparative HPLC (Phenomenex Luna C18 30×100 mm column; linear gradient 5-85% B-A over 15 min; A=5% MeCN—H₂O with 0.1% v/v TFA; B=95% MeCN—H₂O with 0.1% v/v TFA; 30 mL/min; 220 nm detection) to provide compound (Id) as a white solid. MS(ESI⁺) m/z 1087.8.0 (M/3+H)⁺. (2.8 mg, 23.5% yield).

Example 5—Compound (Ie)

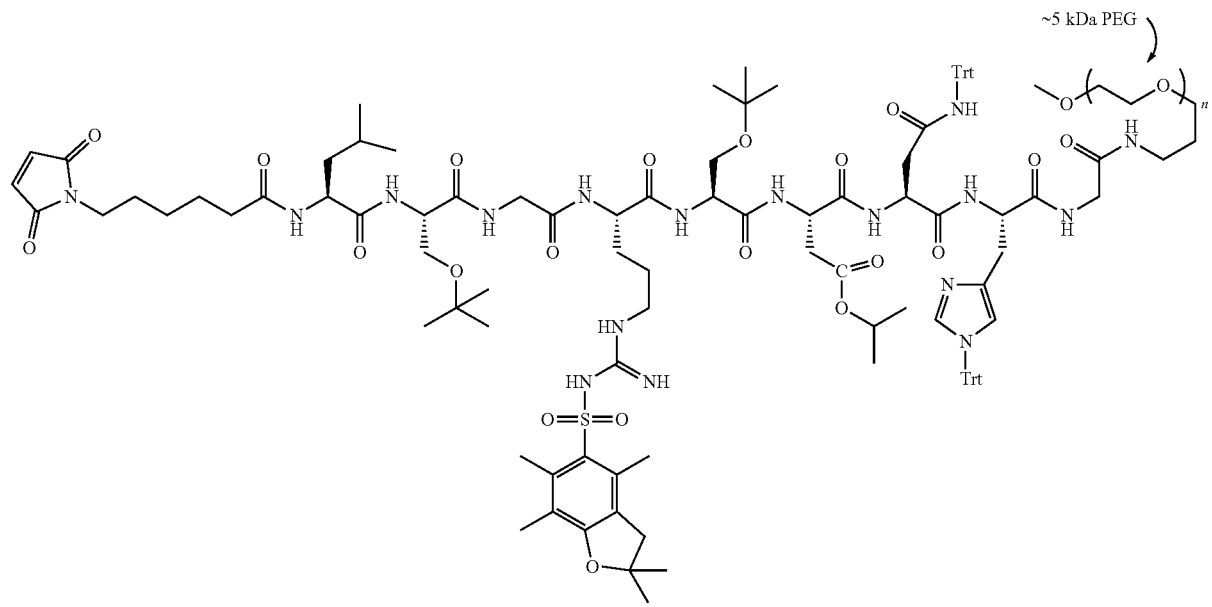

To a solution of intermediate 18 (21 mg, 0.01 mmol) in DMF (200 µl) was added HATU (4.7 mg, 0.012 mmol). The mixture was stirred at RT for 10 min before a solution of methoxy-PEG-(CH₂)₃—NH₂ (NOF, catalog #SUN-BRIGHT® MEPA-50H, CAS #: 116164-53-5, 51.5 mg, 0.034 mmol) in DMF (0.3 mL) and DIPEA (3.6 µl, 0.021 mmol) was added. The reaction was stirred at RT for 4 h and was purified by preparative HPLC (Phenomenex Luna C18 30×100 mm column; linear gradient 25-100% B-A over 15 min; A=5% MeCN—H₂O with 0.1% v/v TFA; B=95% MeCN—H₂O with 0.1% v/v TFA; 30 mL/min; 220 nm detection) to provide compound 20 as a white solid. (28 mg, 38.7% yield).

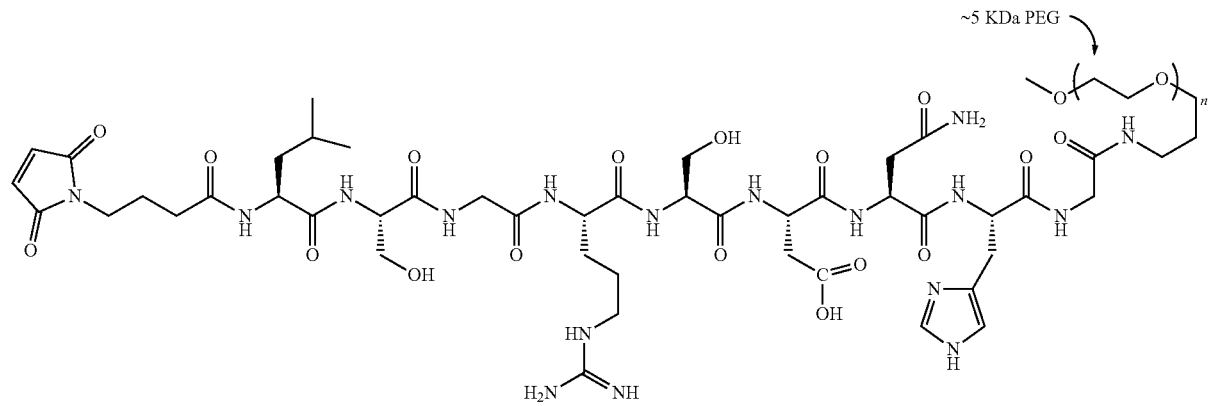

Compound (Ie).

To a vial was added intermediate 20 (28 mg) followed by TFA/H$_2$O (97:3, 1 mL). The reaction was stirred at RT for 60 min before it was concentrated in vacuo. The residue was then taken up in water (2 mL) and filtered through a sterile filter (0.45 uM). The filtrate was lyopholized to provide linker 6 as a white solid (20 mg, 78% yield). MALDI mass spectral showed correct modification of the 5 k PEG compound (FIG. 7).

Example 6—Compound (If)

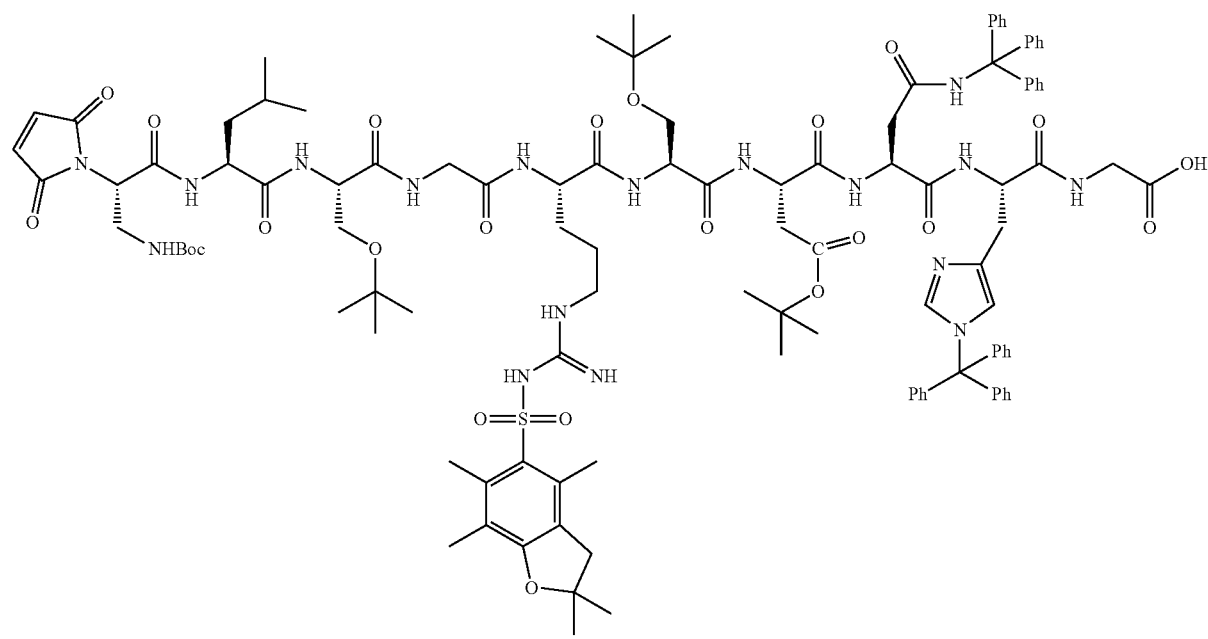

Compound 22.

To resin 17 (600 mg, 0.6 mmol/g) was added a solution of (S)-3-((tert-butoxycarbonyl)amino)-2-(2,5-dioxo-2,5-dihydro-1H-pyrrol-1-yl)propanoic acid (185 mg, 0.650 mmol) (Nat. Biotech. 2014, 1059-1062) and HATU (185 mg, 0.487 mmol) in DMF (0.5 mL) followed by 2,4,6-collidine (1.240 mL, 1.137 mmol). The reaction was shaken for 3 h before it was drained. The resin was washed it by DMF (8 mL×3), DCM (8 mL×2). The resin was then treated with 20% 1,1,1,3,3,3-hexafluoro-2-propanol in DCM (8 mL) for 15 min. The mixture was filtered and the filtrate was concentrated in vacuo to provide compound 22 (136 mg), MS(ESI$^+$) m/z 1057.0 [M/2+H]$^+$.

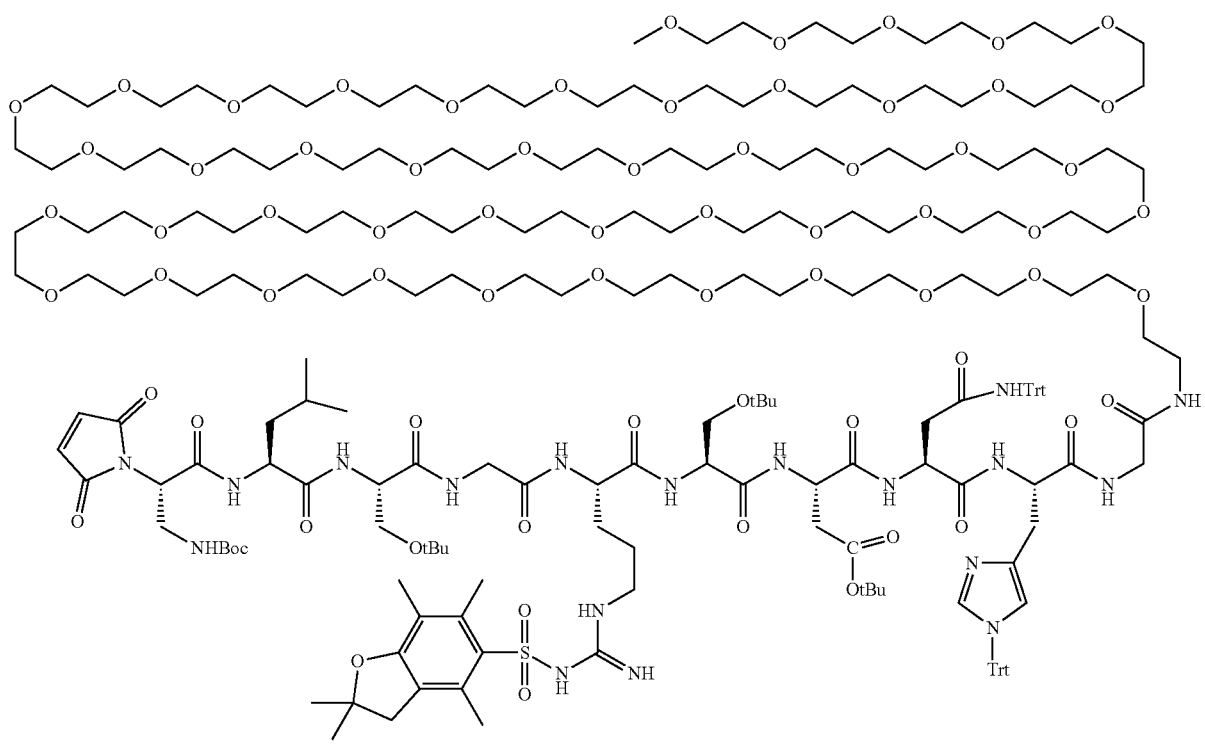

23

Compound 23.

To a stirred solution of intermediate 22 (134.2 mg, 0.063 mmol) in DMF (0.3 mL) was added HATU (29.0 mg, 0.076 mmol). The mixture was stirred at RT for 30 min before a solution of m-dPEG48-amine (136 mg, 0.063 mmol) in DMF (0.4 mL) was added, followed by DIPEA (0.033 mL, 0.190 mmol). The resulting reaction was stirred at RT for 2 h and then purified by preparative HPLC (Phenomenex Luna C18 30×100 mm column; linear gradient 30-100% B-A over 15 min; A=5% MeCN—H$_2$O with 0.1% v/v TFA; B=95% MeCN—H$_2$O with 0.1% v/v TFA; 30 mL/min; 220 nm detection) to provide compound 23 (45.1 mg, 16.75% yield), MS(ESI$^+$) m/z 1413.8 [M/3+H]$^+$.

(If)

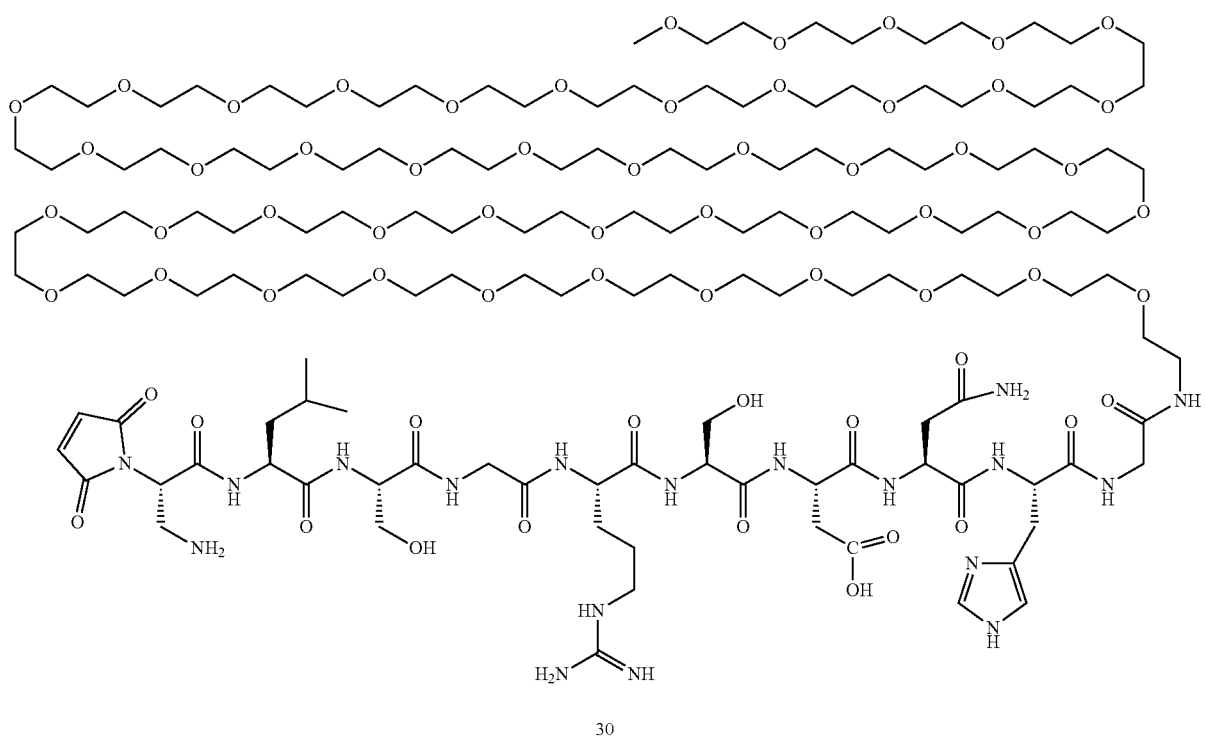

Compound (If).

To a vial was added intermediate 23 (46.5 mg, 10.96 µmol) followed by TFA (500 µL, 6.49 mmol). The mixture was stirred at RT for 1 h before it was concentrated in vacuo and then purified by preparative HPLC (Phenomenex Luna C18 30×100 mm column; linear gradient 0-80% B-A over 15 min; A=5% MeCN—H$_2$O with 0.1% v/v TFA; B=95% MeCN—H$_2$O with 0.1% v/v TFA; 30 mL/min; 220 nm detection) to provide (15.3 mg, 38.3% yield), MS(ESI$^+$) m/z 1078.6 [M/3+H]$^+$.

Example 7—Compound (Ig)

(Ig)

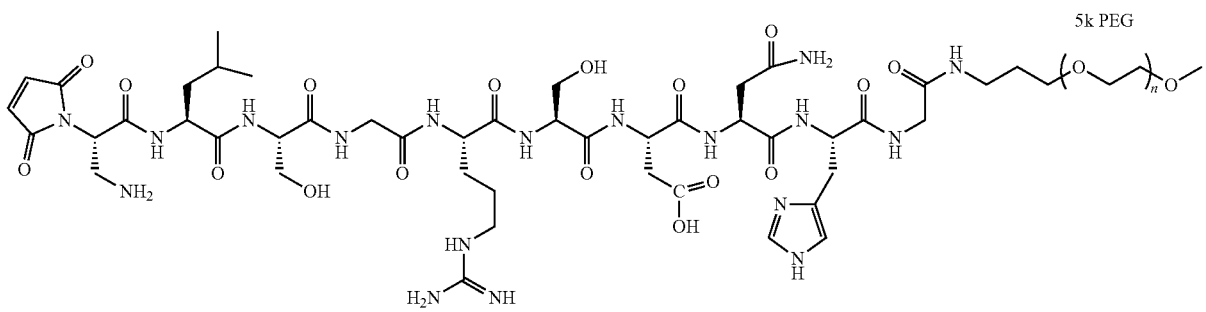

Compound (Ig) was prepared from intermediate 22 and methoxy-PEG-(CH$_2$)$_3$—NH$_2$ (NOF, catalog #SUNBRIGHT® MEPA-50H, CAS #: 116164-53-5) following analogous chemistry that was used to prepare compound (If). MALDI mass spectral showed correct modification of the 5 k PEG compound (FIG. 8).

Example 8—Compound (h)

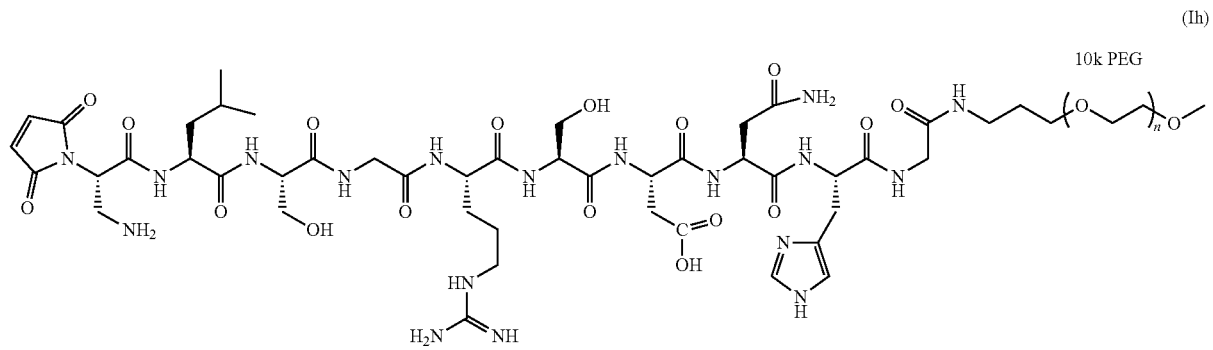

(Ih)

Compound (Ih) was prepared from intermediate 22 and methoxy-PEG-(CH$_2$)$_3$—NH$_2$ (NOF, catalog #SUN-BRIGHT® MEPA-10T, CAS #: 116164-53-5) following analogous chemistry that was used to prepare compound (Ig). MALDI mass spectral showed correct modification of the 10 k PEG compound (FIG. 9).

Example 9—Calculations of Exposure and Distance from a CDR Amino Acid

Using a structure or model of the antibody variable domains (V$_H$ and V$_L$), the accessible surface area (ASA) was calculated for all amino acid side chains. The ASA is defined as the surface traced by the center of a sphere with the radius of a water molecule (1.4 Å) as it is rolled over the surface of a structure or molecular model using the solution first developed by Lee and Richards (Lee and Richards 1971). The side chain exposure of a residue X was compared to the ideal surface area as determined from the Gly-X-Gly tripeptide with the main chain in an extended conformation (Miller et al. 1987). The exposure was then normalized by dividing the ASA by the maximum ASA for a given amino acid type as reported by Miller et al. 1987. The side chain exposure is reported as a percentage where the side chain exposure=residue ASA/maximum ASA.

In order to identify the list of CER residues for a given antibody we used a structure (e.g. X-ray structure of the antibody or antibody fragment such as a FAB) or a homology model of the Fv region of the antibody. The side chain exposure for all amino acids was determined as described above. The side chain exposure is combined with distance to the nearest CDR residue to generate a list of preferred CER residues for a given antibody. All calculations including the accessible surface area, CDR assignment and distance calculations from a residue to nearest CDR were performed using per MOE. 2015, using the CCG CDR definition, which is the union of Kabat, Chothia and IMGT CDR definitions.

The Kabat scheme (Kabat et al., 1991) was developed based on the location of regions of high sequence variation between sequences of the same domain type. It numbers antibody heavy (V$_H$) and light (V$_L$ V$_k$ and V$_\lambda$) variable domains. Chothia's scheme (Al-Lazikani, 1997) is similar to Kabat's but corrects where an insertion is annotated around the first V$_H$ complementarity determining region (CDR) so that it corresponds to a structural loop. We define the V$_H$ and V$_L$ CDRs by combining the Kabat and Chothia CDR definitions.

FIGS. 10A and 10B show tables listing CTLA4 Ab residues having the desired side chain exposure and proximity to a CDR amino acid. Thus, in one embodiment, the Cys substitution site is at Kabat number 1, 3, 25, 46, 68, 72, 76, 82a, or 83 of the heavy chain or Kabat number 1, 3, 5, 7, 8, 45, 57, 60, 63, 65, 66, 67, and 69 of the light chain, as shown in FIG. 10A. In another embodiment, the Cys substitution site is at Kabat number 5, 19, 23, 43, 74, 75, 82b, 84, 85, or 105 of the heavy chain or at Kabat number or Kabat number 18, 20, 77, or 100 of the light chain, as shown in FIG. 10B.

Example 10—Conjugation

Antibodies having selected Cys substitutions were transiently expressed in Expi-CHO cells and purified using standard protocols with protein A chromatography. Purified antibodies were treated with an excess (10 molar equivalents) of a reducing agent TCEP (tris(2-carboxyethyl)phosphine) at 37° C. for 1-3 hours in a buffered aqueous solution at pH 7.2 containing 2 mM EDTA. The TCEP was removed by passing the reduced variant antibody through a Sephadex G-25 or an ion-exchange column. The reduction of the antibody was confirmed on an analytical reverse phase HPLC system. The purified, reduced antibody was treated with an excess of a disulfide re-oxidising reagent (10 molar equivalents) such as, dhAA (dehydroascorbic acid), CuSO$_4$ (copper(II) sulfate), air, H$_2$O$_2$ (hydrogen peroxide), N—CS (N-chlorosuccinimide), or O$_2$ (molecular oxygen) at 4° C. or room temperature for 0.5-24 h in a buffered aqueous solution (pH 7.0). The ratio of free thiols per antibody was estimated by determining the protein concentration from absorption of the protein solution at 280 nm, and the thiol concentration from reaction of the protein with DTDP (dithiodipyridine). The re-oxidation of the antibody was monitored on an analytical reverse phase HPLC and aggregation levels on an analytical size-exclusion column.

After reduction and re-oxidation as described above, the antibody in buffered aqueous solution (pH 7) was treated with 3 molar equivalents of a BM-linker per thiol of antibody containing a cysteine-reactive functional group (maleimide, iodoacetamide, or similar reactive). BM-linkers, typically dissolved in deionized water, was added to the reaction mixture. The reaction was allowed to proceed for 2 hours at room temperature or 4° C. overnight. Afterwards, the conjugate was purified by protein A, ion exchange, size exclusion, or a combination of multiple types of chromatography. Analytical tests such as SDS-PAGE, Western blots, HIC, Reverse phase HPLC and Mass Spectrometry were carried out to confirm the attachment of the BM linker at the engineered position.

Example 11—Matriptase Cleavage of Linker Moiety

The following procedure was used for assay for matriptase cleavage of a prodrugged antibody who linker moiety had a matriptase cleavable peptide sequence.

Prodrugged antibody (40 μg) was incubated with 1.3 μg of hMatriptase (30:1, R&D system, 3946-SE-010) in 100 mM Tris buffer, pH7.6 at 37° C. At each time point, 10 μL of sample was mixed with 10 μL quenching buffer (100 mM phosphate buffer with 4M GdnCl and 0.4M TCEP, pH 2.5) to simultaneously deactivate the enzyme and reduce the prodrugged antibody. The quenched sample was subjected to LC/MS analysis.

Example 12—Binding to Activated CD4$^+$ T-Cells

Serial dilutions of prodrugged and de-prodrugged (i.e., with linker moiety cleaved) antibody were tested and binding was detected by an APC labelled anti-human IgG secondary antibody. Flow cytometric analyses were performed using a Canto flow cytometer, and the geometric mean fluorescence intensity (GMFI) was determined using FlowJo analysis software. The binding of both test articles was compared with the binding of unprodrugged CTLA4 Ab of SEQ ID NO:1 and NO:2.

Figure 11A:
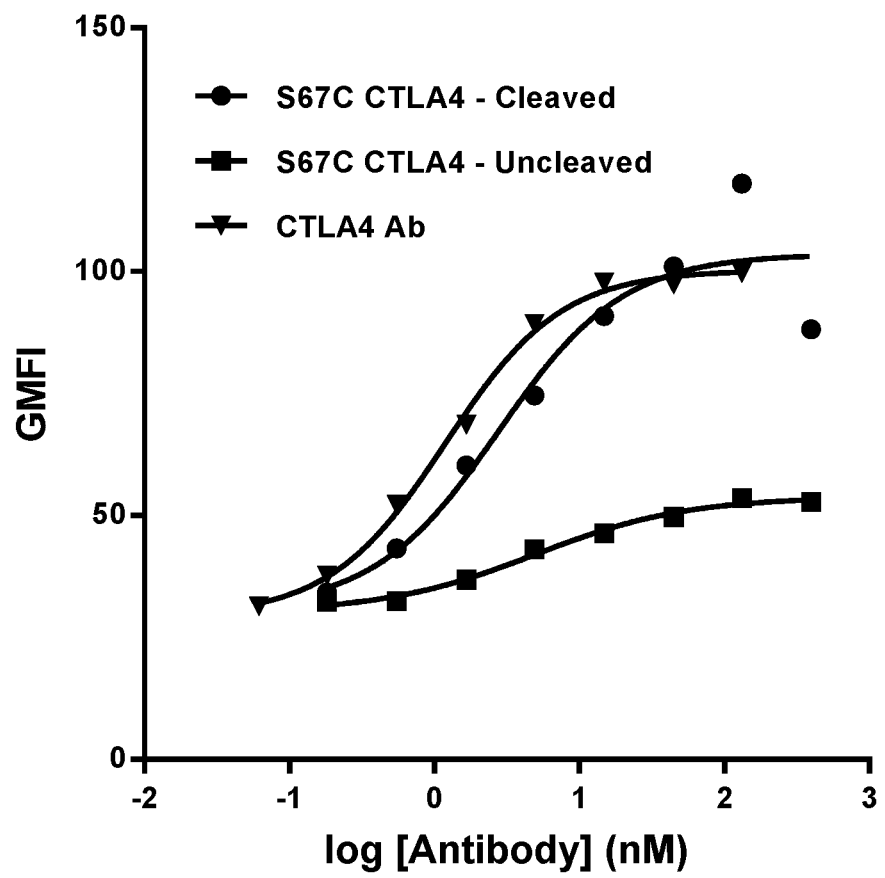
Figure 11B:
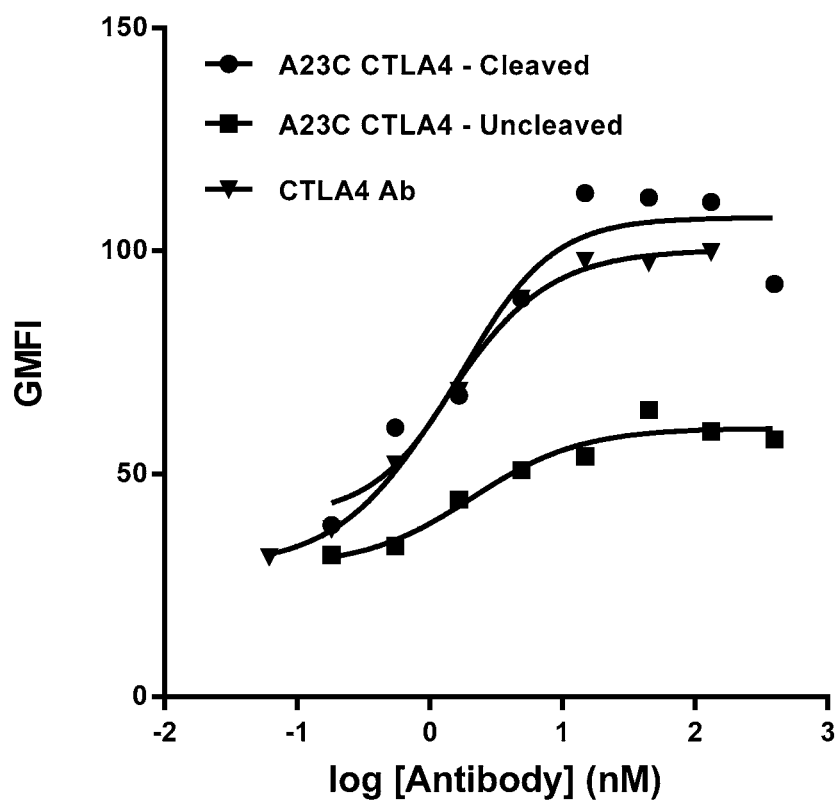

Illustrative results are provided in FIGS. 11A and 11B. In FIG. 11A the binding curve labeled "CTLA4 Ab" is for the native CTLA4 Ab of SEQ ID NO:1, without any Cys substitution. The binding curve labeled "S67C CTLA4—Uncleaved" is the binding curve for CTLA4 Ab having a $V_L$ S67C substitution and then prodrugged with blocking/linker moiety (Ie), which comprises a 5 kDa PEG. As can be seen from the curve, binding to the CD4$^+$ T-cells is substantially inhibited. Lastly, the "S67C CTLA4—Cleaved" curve shows that binding is essentially fully restored upon cleavage of blocking/linker moiety with matriptase, releasing the 5 kDa PEG.

FIG. 11B shows the results for the analogous experiment, in which CTLA4 Ab is prodrugged at $V_H$ A23C. Again, loss of binding upon prodrugging and restoration of binding upon cleavage of the linker is evident.

Figure 11C:
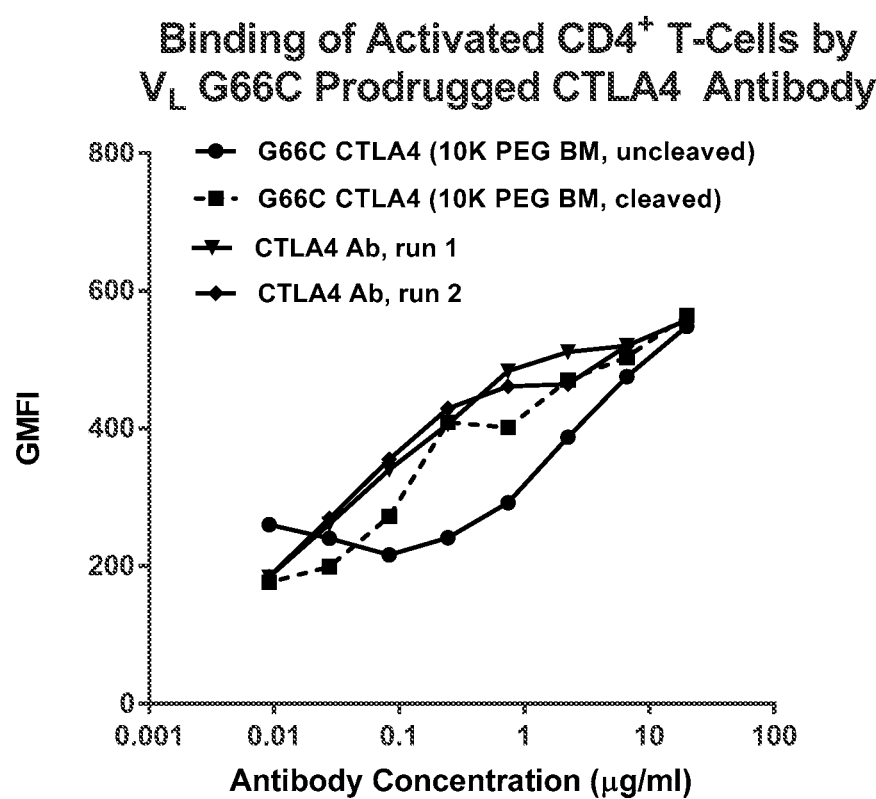
Figure 11D:
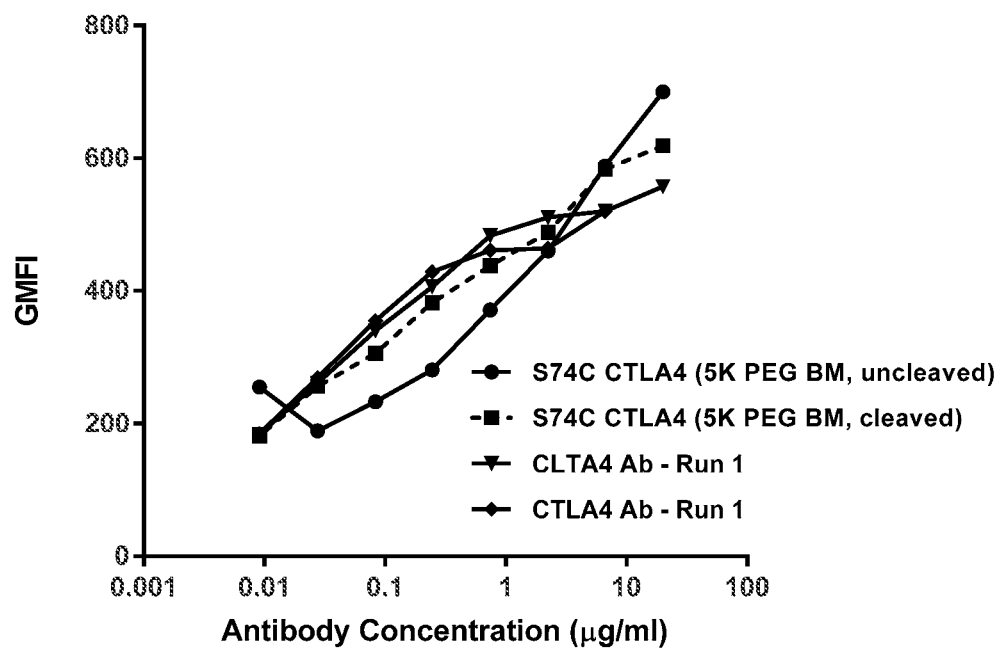
Figure 11E:
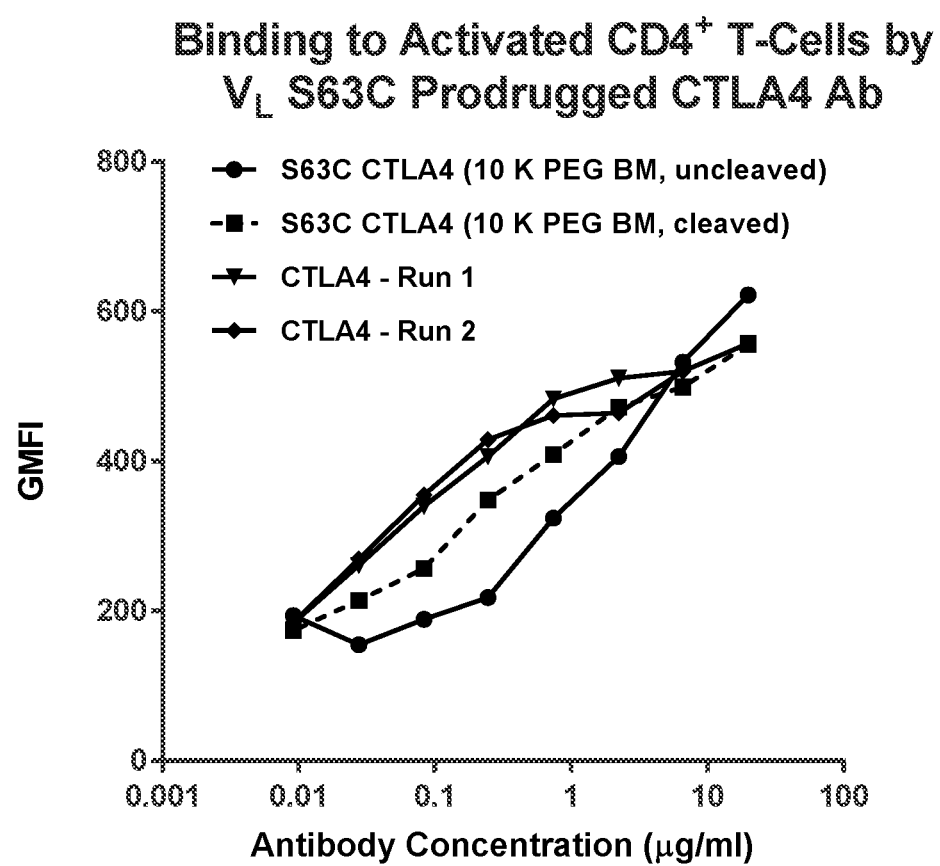

Additional binding graphs as shown in FIGS. 11C through 11E.

Example 13—IL-2 Secretion Assay

The activity of prodrugged and de-prodrugged antibodies was characterized by an in vitro functional assay using Staphylococcal enterotoxin B (SEB). SEB is a superantigen that strongly activates T cells and stimulates cytokine secretion. Fresh peripheral blood mononuclear cells (PBMC) were isolated from 2 healthy human donors and treated with several concentrations of prodrugged and de-prodrugged antibodies. Simultaneously, a suboptimal concentration (85 ng/mL) of SEB was added to stimulate the cells. T-cell activation was monitoring secretion of the cytokine IL-2 was measured after Day 3 of incubation/treatment.

The following procedure was used: Two buffy coats were collected from 2 healthy donors (Donor 1 and Donor 2 in FIGS. 12A/B and 13A/B, respectively) at Stanford Blood Center. Whole PBMC were isolated from the buffy coats using a standard Ficoll-Paque separation method of underlaying 15 mL Ficoll for 20 mL buffy coat and spinning for 20 minutes at 2000 rpm with no brake. White interface was separated carefully and washed with PBS several times to remove extra Ficoll and platelets. The cells were then resuspended with T-cell assay media. Serial dilutions of positive control antibody (CTLA4 Ab) from (40 μg/mL to 0.01 μg/mL) and 8 μg/mL to 0.01 μg/ml for the prodrugged and de-prodrugged antibodies were performed and plated in triplicate in a 96-well flat-bottom tissue culture plate. Isolated PBMC were added to the plate at $1 \times 10^5$ cells/well and stimulated by superantigen SEB at 85 ng/mL (a sub-optimal concentration of SEB determined by titrating SEB and by observing the stimulation on T-cell proliferation). The cells were incubated in a 37° C. incubator for 3 days. IL-2 concentration in the supernatants was measured by homogeneous time-resolved fluorescence (HTRF). HTRF data were analyzed using Softmax Pro and graphed using Graph-Pad Prism software.

Figure 12A:
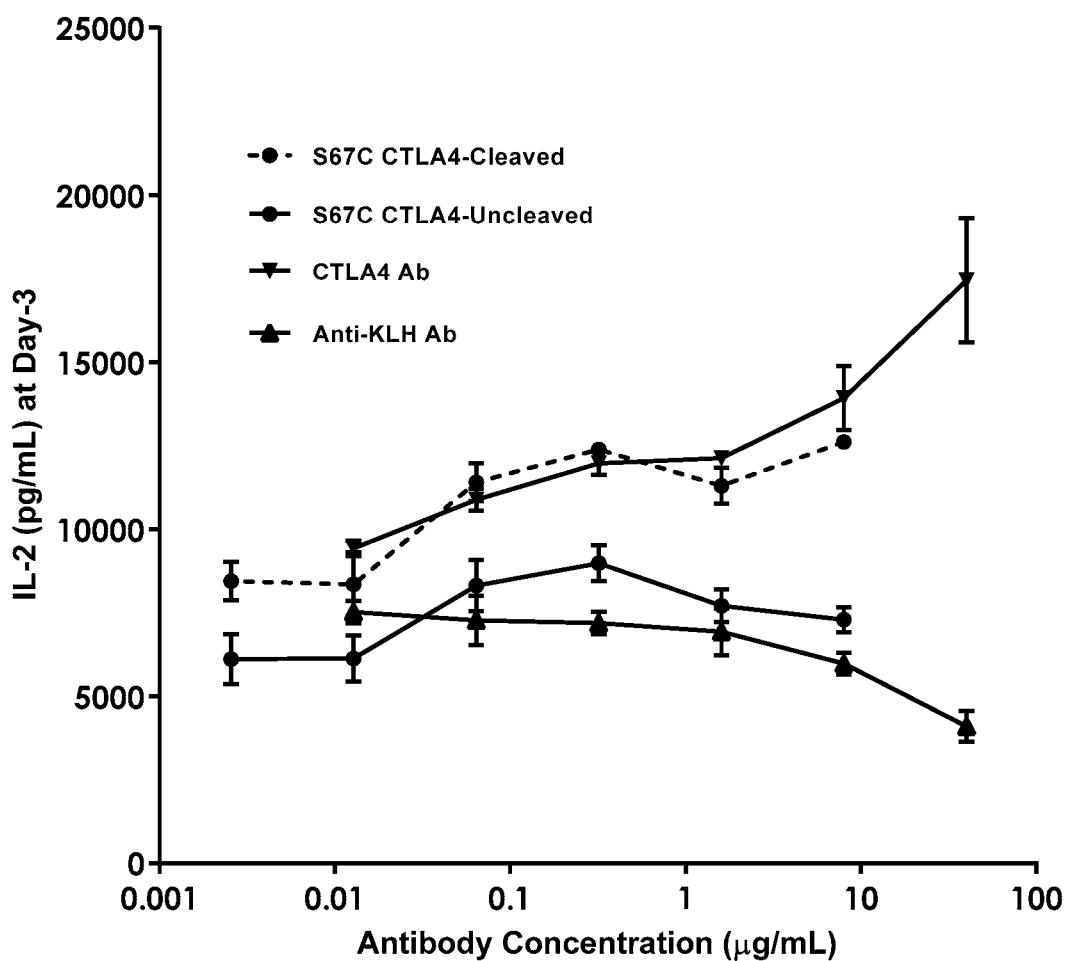
Figure 12B:
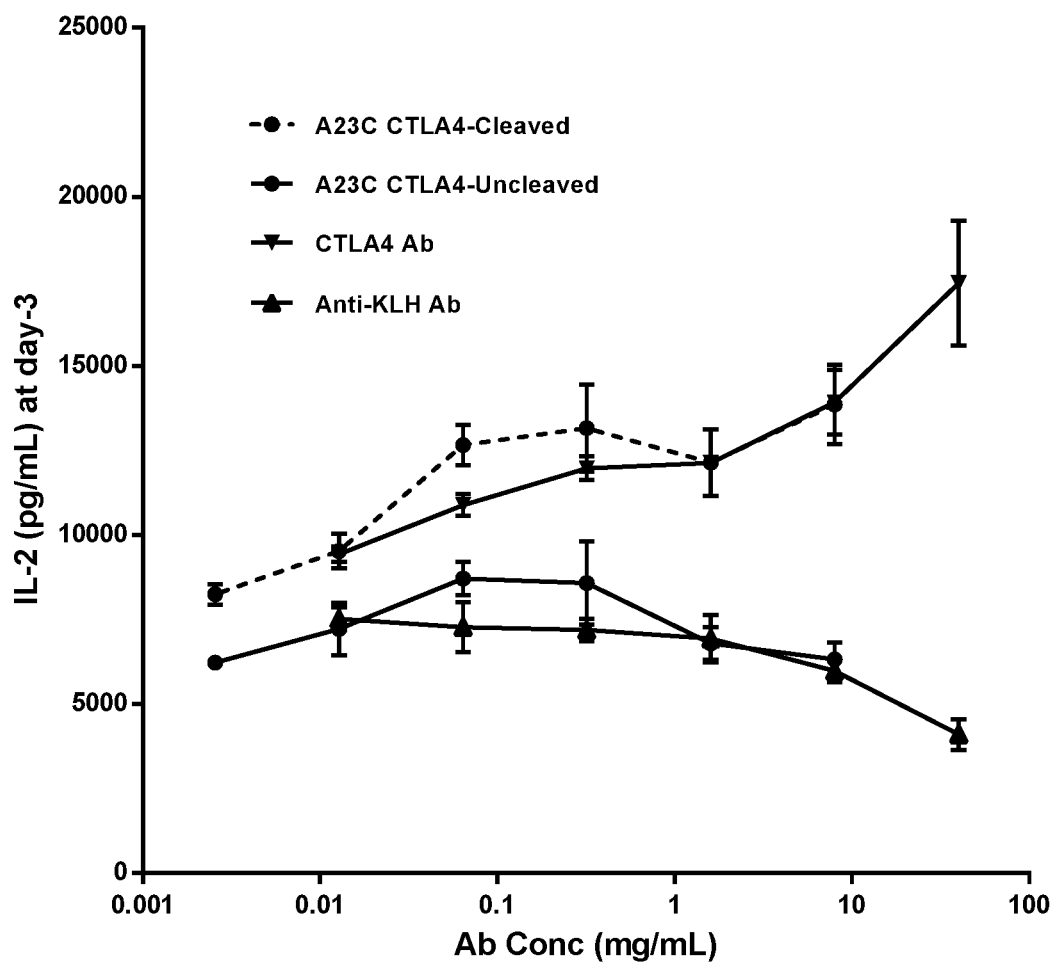
Figure 13A:
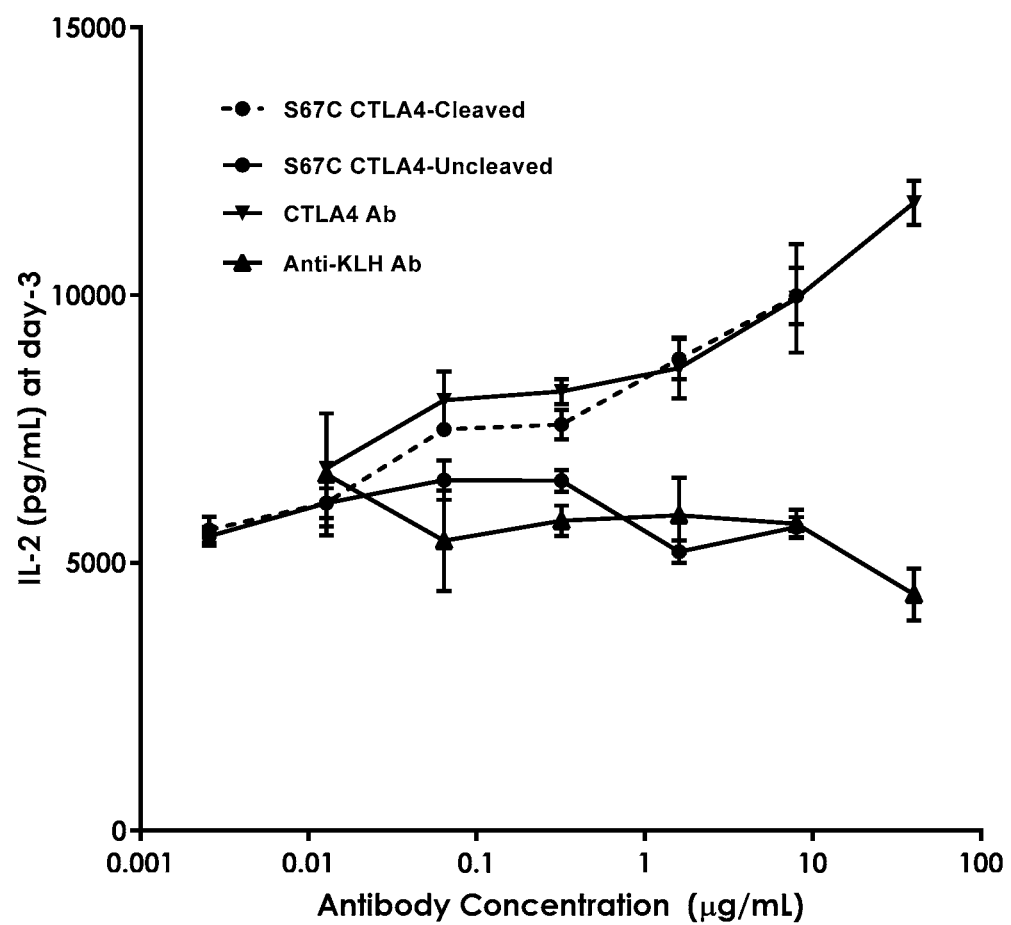
Figure 13B:
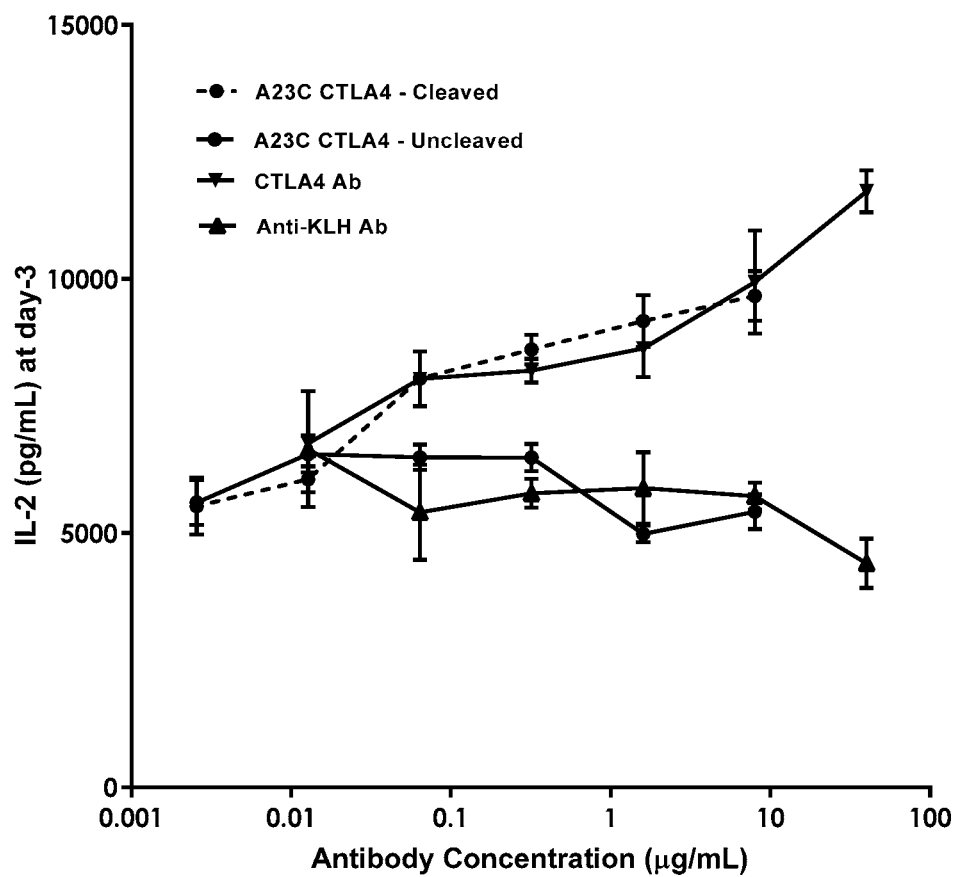

The results are shown in FIG. 12A and FIG. 12B for Donor 1 and in FIGS. 13A and 13B for Donor 2. In each instance, it is seen that prodrugging CTLA4 Ab at either $V_L$ S67C or $V_H$ A23C results in reduced IL-2 induction and de-prodrugging restores IL-2 induction. The control, prodrugged and de-prodrugged anti-CTLA4 antibodies in FIGS. 12A/B and 13A/B were the same as those described in the preceding CD4$^+$ T cell example and FIGS. 11A/B.

We observed that the antibodies exhibited dose dependent activity in different donors when compared to the IL-2 secretion elicited by an isotype anti-KLH (keyhole limpet hemocyanin) control antibody. When compared to CTLA4 Ab, the prodrugged antibody showed reduced functional activity. Upon de-prodrugging, there was an approximately 3 fold increase in IL-2 secretion at the highest concentration of the de-prodrugged antibody similar to the positive control of CTLA4 Ab. This result confirms that reducing binding of an antibody by attachment of a blocking moiety reduces activity in a functional T cell assay and that such activity is restored upon removal of the blocking moiety.

Example 14—Prodrugging of CD137 Antibody

Four different CD137 antibodies were used in this example: (a) CD137 Ab proper (SEQ ID NO:3 and NO:4); (b) CD137 Ab conjugated via a $V_L$ S67C substituted-in Cys to blocking moiety-linker (If), which has a 2 kDa PEG; (c) CD137 Ab conjugated via a $V_L$ S67C substituted-in Cys to blocking moiety-linker (Ih), which has 10 kDa PEG; and (d) CD137 Ab conjugated via a $V_L$ S67C substituted-in Cys to linker (III) (structure below), which has no blocking moiety and serves as a "peptide control."

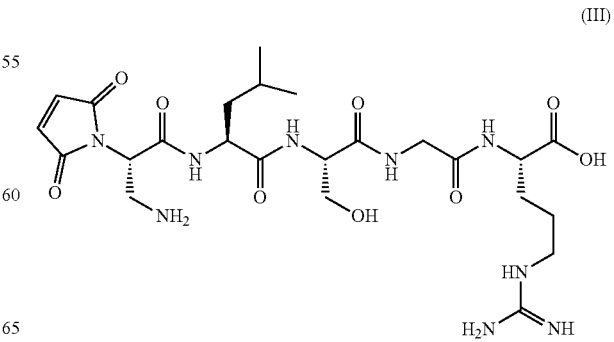

(III)

Figure 14:
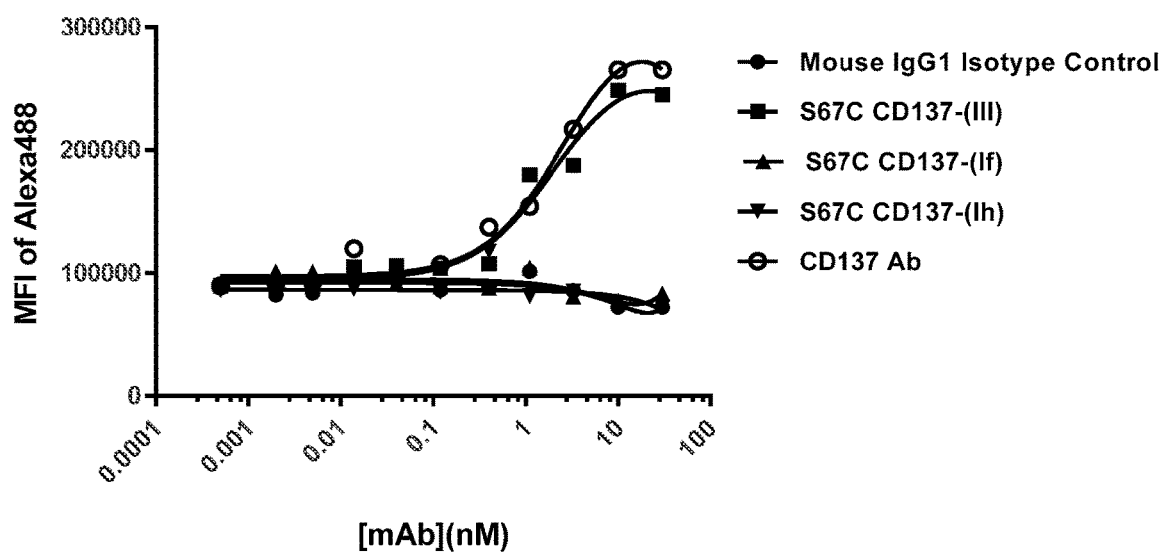

Two different assays were performed. In the first assay, the binding of CD137 Ab and its variants (u)-(d) to CD8+ ConA activated splenotypes was compared, using mean fluorescence units by flow cytometry with secondary Alexa 488 conjugated goat anti-human antibody. The results are presented in FIG. 14. They show that CD137 Ab and variant (d) bind effectively, but that variants (b) and (c) do not. (Invitrogen mouse isotype control antibody, Catalog #: MA1-10406 served as an isotype control.) Thus, the attachment of a small peptide such as with (III) is insufficient to effectively inhibit binding notwithstanding proximity of the $V_L$ S67C site to a CDR amino acid. However, the presence of a blocking moiety of substantial size, such as 2 kDa or 10 kDa PEG, does result in inhibition.

Figure 15A:
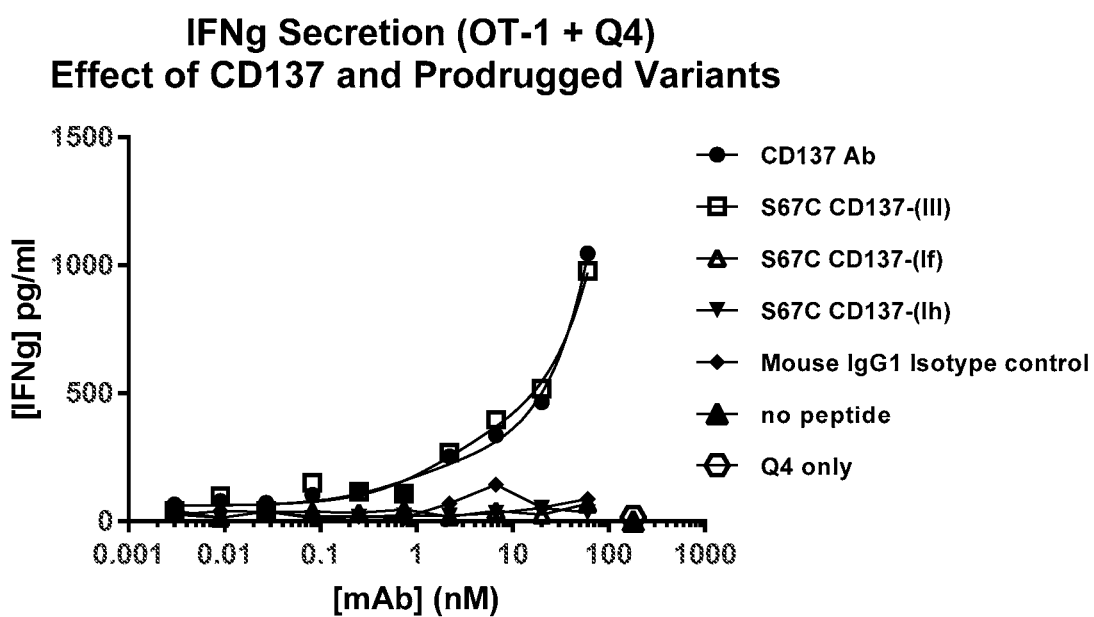
Figure 15B:
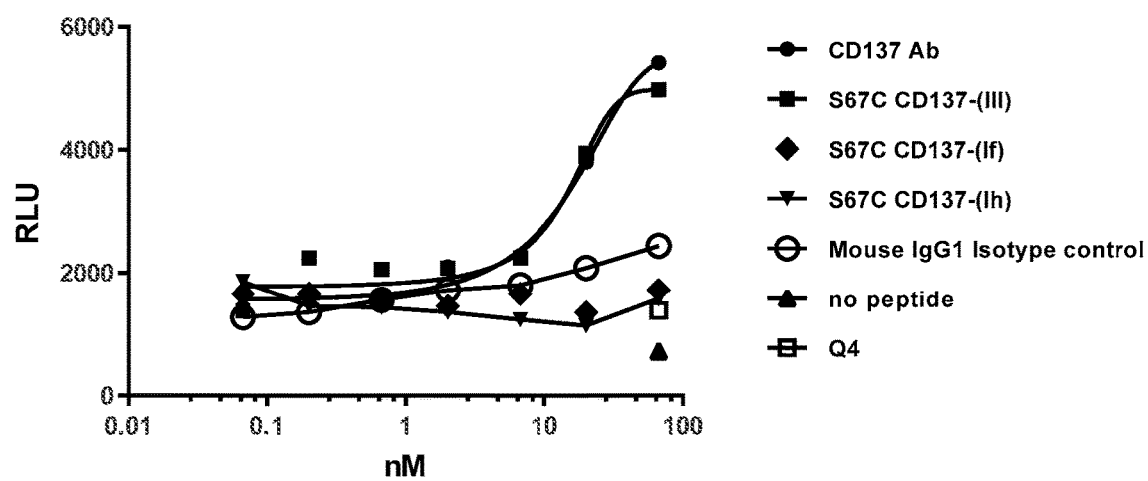

The second assay was a functional assay. In a first aspect, as shown in FIG. 15A, secretion of IFNg (interferon-gamma) from activated CD8 T cells was measured. As with the results on OT-1 CD8+ T cell SIIQFEKL peptide activated splenocytes binding, CD137 Ab and variant (d) were effective but variants (b) and (c) were not, demonstrating inhibition of their activity. A second aspect is shown in FIG. 15B: Q4 peptide was added to OT-1 cells to induce expression of CD137 receptor on the cells' surfaces. Binding of CD137 to its receptor then induces CD8 T cell proliferation. CD137 Ab and variant (d) induced additional to the antigen specific CD8 T cell proliferation, but variants (c) and (d) did not. The anti-KLH antibody, Catalog #: MA1-10406b, "no peptide" and Q4 single points were negative controls.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Al-Lazikani, B. et al. (1997) "Standard conformations for the canonical structures of immunoglobulins," *J. Mol. Biol.*, 273, 927-948.
Bhakta et al., US 2016/0130358 A1 (2016).
Chothia C1, Lesk A M. *J Mol Biol.* 1987 196(4):901-17, "Canonical structures for the hypervariable regions of immunoglobulins."
Chothia C1 et al. *Nature* 1989 342(6252), 877-83, "Conformations of immunoglobulin hypervariable regions."
Daugherty et al., U.S. Pat. No. 9,169,321 B2 (2015).
Dennis, WO 2016/179003 A1 (2016).
Desnoyers et al., "Tumor-Specific Activation of an EGFR-Targeting Probody Enhances Therapeutic Index," *Sci. Transl. Med.* 2013, 5(207), 1.
Eigenbrot et al., US 2007/0092940 A1 (2007).
Foote and Winter, "Antibody Framework Residues Affecting the Conformation of the Hypervariable Loops," *J. Mol. Biol.* 1992, 224, 487.
Kabat, E. A. et al. (1991) *Sequences of Proteins of Immunological Interest*, Fifth Edition, NIH Publication No. 91-3242.
U.S. Pat. No. 8,809,504 B2 (2014).
Lee, B; Richards, F M. (1971). "The interpretation of protein structures: estimation of static accessibility". *J Mol Biol.* 55 (3): 379-400.
Lowman et al., US 2014/0023664 (2014).
Lowman et al., U.S. Pat. No. 9,120,853 B2 (2015). [2015a].
Lowman et al., US 2015/0079088 A1 (2015). [2015b].
Lowman et al., U.S. Pat. No. 9,540,440 B2 (2017).
Makabe et al., "Thermodynamic Consequences of Mutations in Vernier Zone Residues of a Humanized Anti-human Epidermal Growth Factor Receptor Murine Antibody, 528," *J. Biol chem.* 2008, 283(2), 1156.
Miller, S.; Janin, J.; Lesk, A. M.; Chothia, C. (1987). "Interior and surface of monomeric proteins". *J. Mol. Biol.* 196: 641-656.
Molecular Operating Environment (MOE), 2016.0801; Chemical Computing Group ULC, 1010 Sherbooke St. West, Suite #910, Montreal, QC, Canada, H3A 2R7, 2017.US 2015/0087810 A1 (2015).
Moore et al., US 2016/0289324 A1 (2016).
Moore et al., U.S. Pat. No. 9,562,073 B2 (2017).
Polu and Lowman, "Probody therapeutics for targeting antibodies to diseased tissue," *Expert Opin. Biol. Ther.* 2014, 14(8), 1049.
Rodeck et al., US 2010/0189727 A1 (2010).
Sagert et al., US 2016/0355592 A1 (2016). [2016a].
Sagert et al., US 2016/0355599 A1 (2016). [2016b].
Stagliano et al., U.S. Pat. No. 8,399,219 B2 (2013).
Stagliano et al., U.S. Pat. No. 9,453,078 B2 (2016).
Tipton et al., US 2017/0044259 A1 (2017).
Tomasi et al., U.S. Pat. No. 4,732,863 (1988).
Trouet et al., US 2004/0014652 A1 (2004).
Waldmann et al., US 2013/0028893 A1 (2013).
Waldmann et al., U.S. Pat. No. 8,623,357 B2 (2014).
Wang et al., US 2016/0009817 A1 (2016).
West et al., U.S. Pat. No. 9,127,053 B2 (2015).
West et al., U.S. Pat. No. 9,487,590 B2 (2016). [2016a].
West et al., US 2016/0311903 A1 (2016). [2016b].
West et al., US 2016/0355587 A1 (2016). [2016c].
Williams et al., U.S. Pat. No. 9,193,791 B2 (2015).

Table of Sequences

The following table summarizes the sequences disclosed in this specification.

| LIST OF SEQUENCES | |
|---|---|
| SEQ ID NO: | SEQUENCE DESCRIPTION |
| 1 | Anti-CTLA4 antibody heavy chain a.a. |
| 2 | Anti-CTLA4 antibody light (kappa) chain a.a. |
| 3 | Anti-CD137 antibody heavy chain a.a. |
| 4 | Anti-CD137 antibody light (kappa) chain a.a. |
| 5 | Protease cleavable peptide a.a. |
| 6 | Protease cleavable peptide a.a. |
| 7 | Protease cleavable peptide a.a. |
| 8 | Protease cleavable peptide a.a. |
| 9 | Protease cleavable peptide a.a. |

| LIST OF SEQUENCES | |
|---|---|
| SEQ ID NO: | SEQUENCE DESCRIPTION |
| 10 | Protease cleavable peptide a.a. |
| 11 | Protease cleavable peptide a.a. |
| 12 | Protease cleavable peptide a.a. |
| 13 | Protease cleavable peptide a.a. |
| 14 | Protease cleavable peptide a.a. |
| 15 | Protease cleavable peptide a.a. |
| 16 | Protease cleavable peptide a.a. |

What is claimed is:

1. A prodrugged antibody according to formula (I)

$$(BM-L)_m\text{-}Ab \qquad (I)$$

wherein
- Ab is an antibody having at least one amino acid in its heavy or light chain variable region replaced by a Cys, wherein the replaced amino acid (a) is in a framework region; (b) has a side chain exposure of at least 30% and (c) is within 10 Å, of a CDR amino acid;
- BM is a blocking moiety that inhibits binding of Ab to its antigen;
- each L is, independently, a linker moiety bonded to BM and Ab, L comprising a cleavable moiety and being bonded to Ab at aforesaid Cys; and
- m is 1, 2, 3, or 4; and
- wherein blocking moiety BM is a poly(ethylene glycol).

2. The prodrugged antibody of claim 1, wherein the at least one replaced amino acid in antibody Ab is at Kabat position 1, 3, 5, 19, 23, 25, 43, 46, 68, 72, 74, 75, 76, 82a, 82b, 83, 84, 85, or 105 of the heavy chain variable region or at Kabat position 1, 3, 5, 7, 8, 18, 20, 45, 57, 60, 63, 65, 66, 67, 69, 77, or 100 of the light chain variable region.

3. The prodrugged antibody of claim 1, wherein the at least one replaced amino acid in antibody Ab is at Kabat position 23 of the heavy chain or Kabat position 67 of the light chain.

4. The prodrugged antibody of claim 1, wherein the at least one replaced amino acid in antibody Ab is at Kabat position 23 of the heavy chain.

5. The prodrugged antibody of claim 1, wherein the at least one replaced amino acid in antibody Ab is Kabat position 67 of the light chain.

6. The prodrugged antibody of claim 1, wherein the poly(ethylene glycol) has a molecular weight of at least about 2 kDa.

7. The prodrugged antibody of claim 1, wherein cleavable moiety in L is an enzymatically cleavable peptide.

8. The prodrugged antibody of claim 7, wherein the enzymatically cleavable peptide is cleavable by at least one enzyme selected from the group consisting of fibroblast activation protein (FAP), urokinase-type plasminogen activator (uPA, urokinase), MT-SP1/matriptase, legumain, and a matrix metalloprotease.

9. The prodrugged antibody of claim 8, wherein the enzyme is matriptase.

10. The prodrugged antibody of claim 7, wherein the enzymatically cleavable peptide is LSGRSDNH (SEQ ID NO:5), LSGX (SEQ ID NO:16) or LSGK (SEQ ID NO:16).

11. The prodrugged antibody of claim 1, having a structure according to formula (IIa) to (IIh):

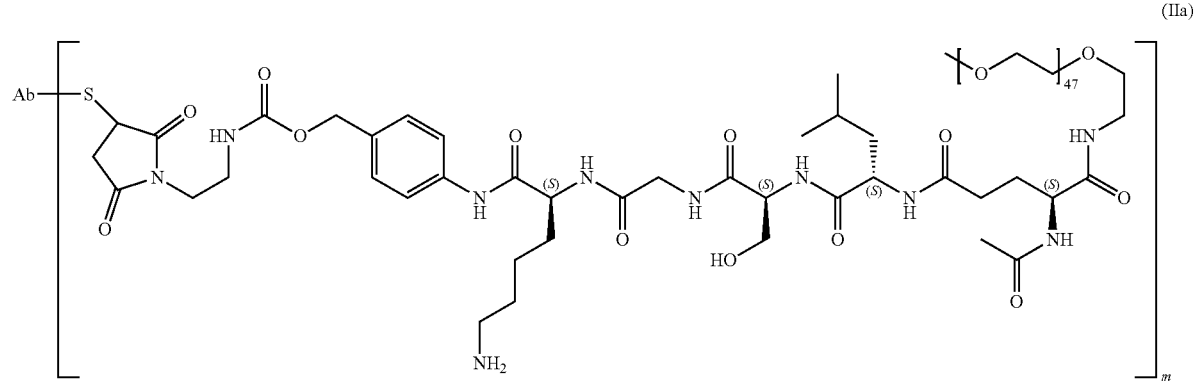

(IIa)

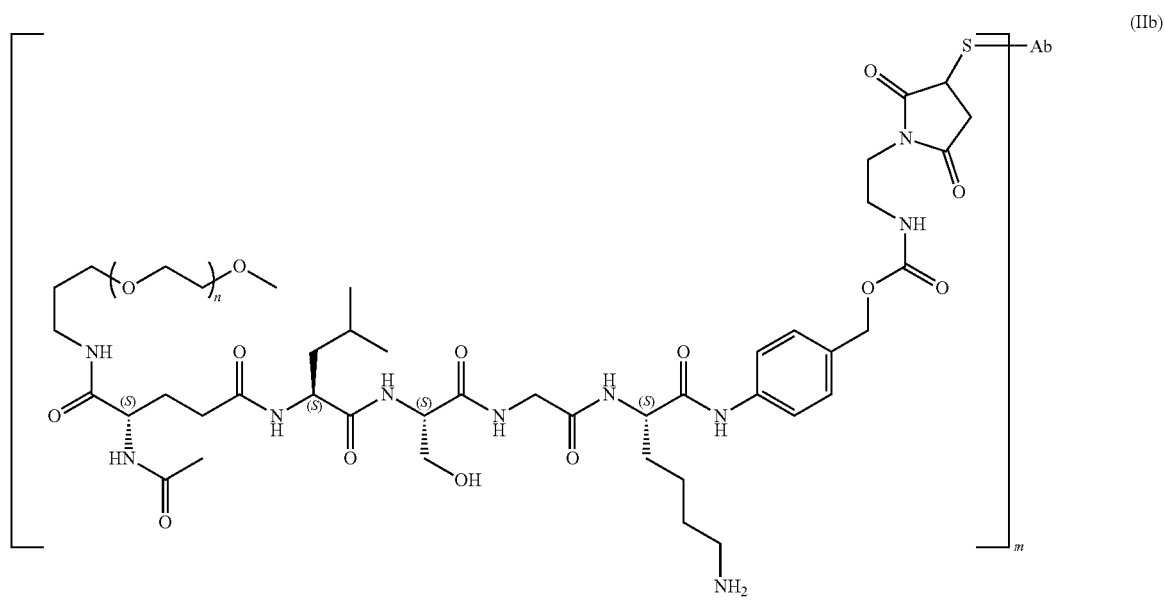

(IIb)

n = 100-155

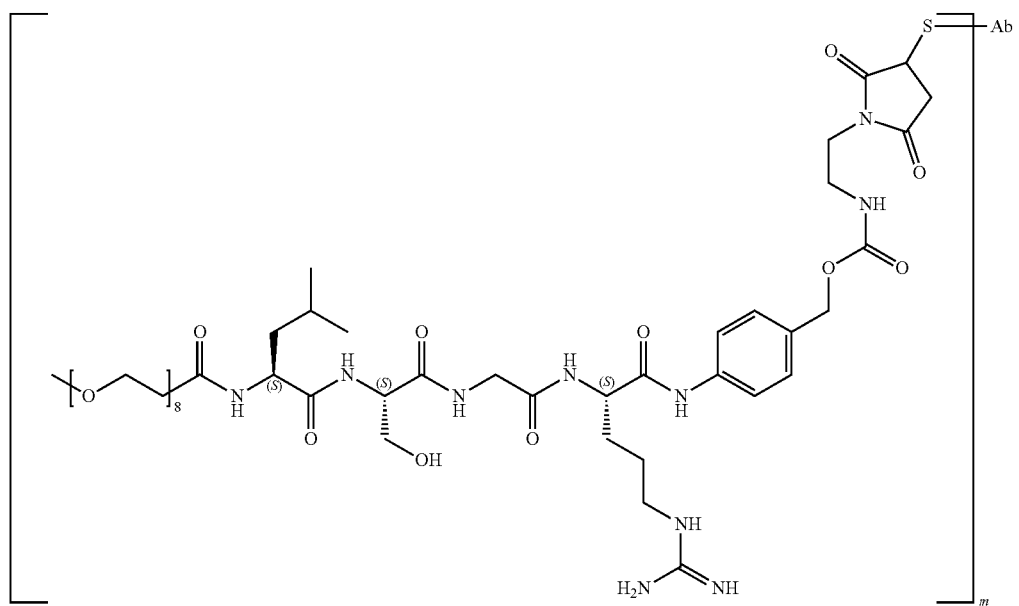
(IIc)
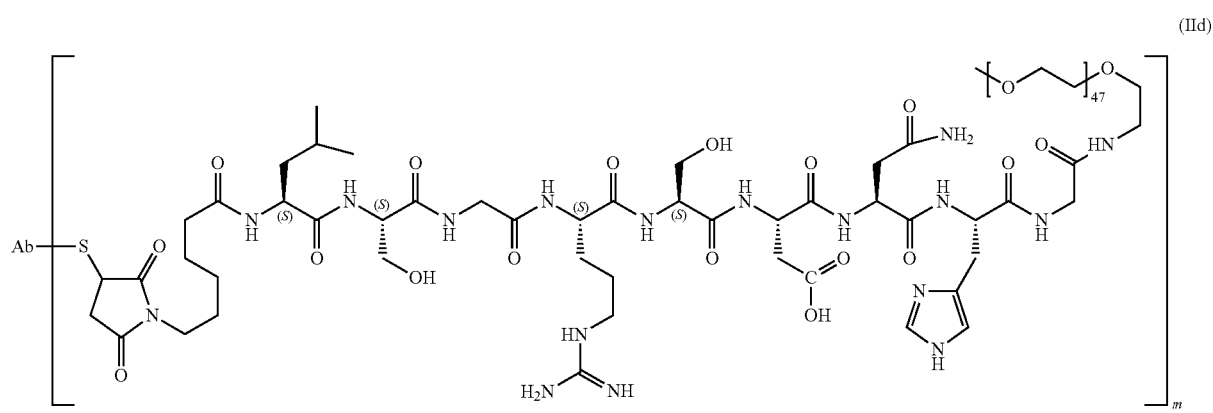
(IId)
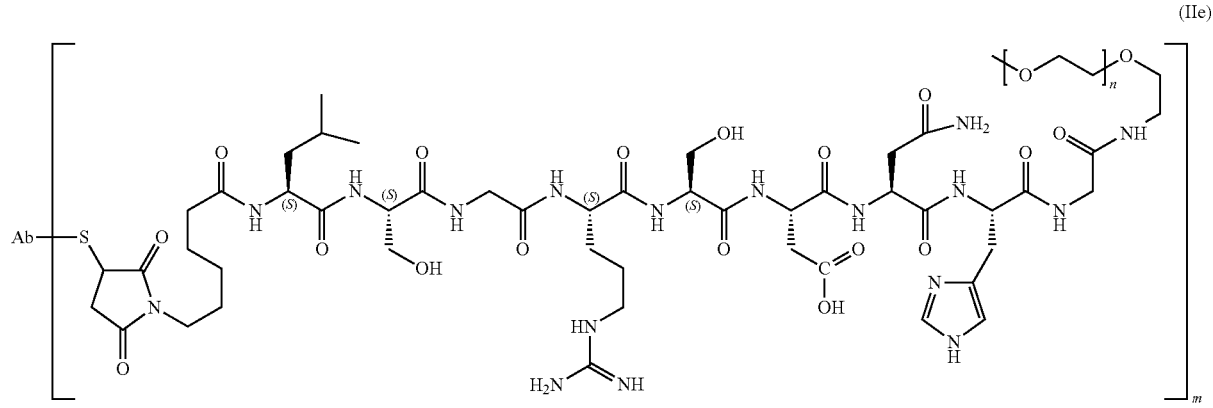
(IIe)
n = 100-155

-continued
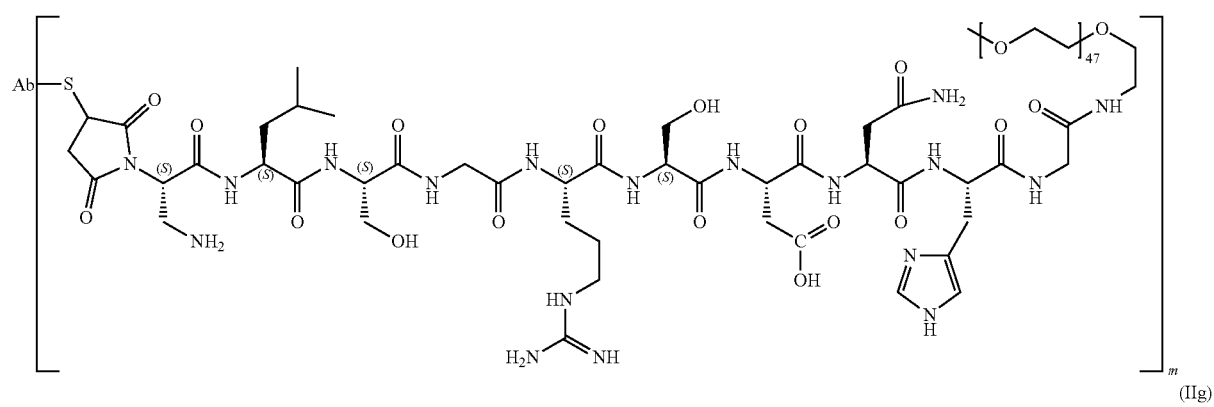
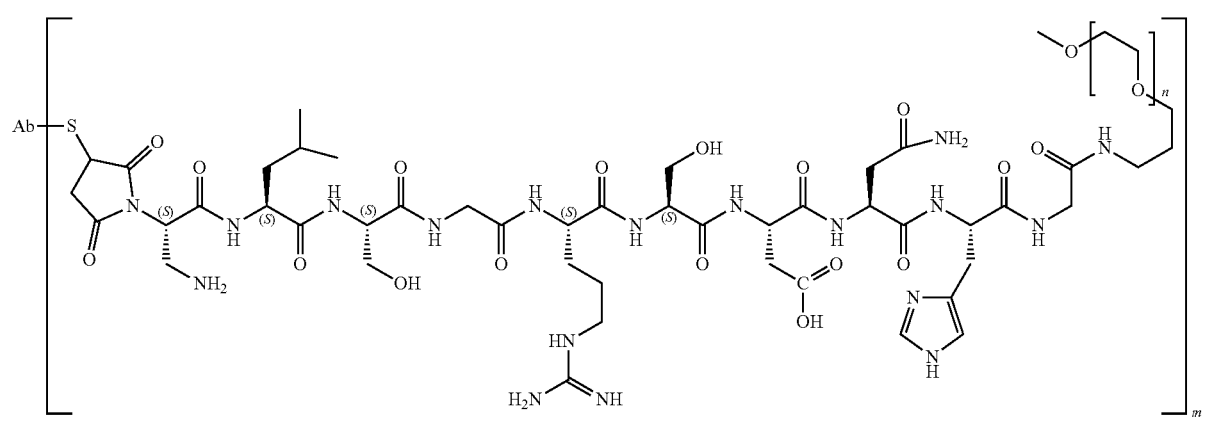
n = 100-155
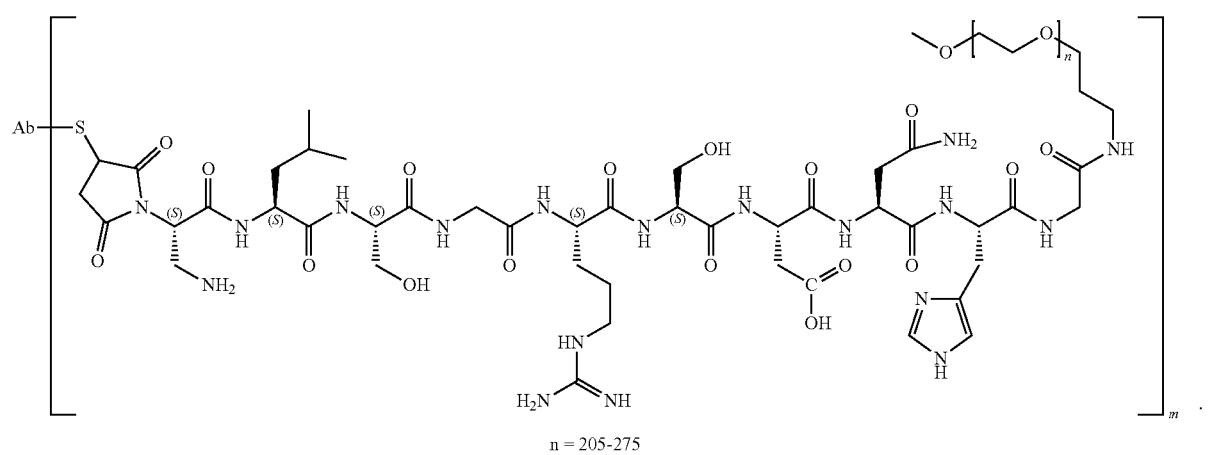
n = 205-275
\* \* \* \* \*

SEQUENCE LISTING

```
<160> NUMBER OF SEQ ID NOS: 16

<210> SEQ ID NO 1
<211> LENGTH: 448
<212> TYPE: PRT
<213> ORGANISM: Homo sapiens
<220> FEATURE:
<221> NAME/KEY: MISC_FEATURE
<223> OTHER INFORMATION: Anti-CTLA4 antibody heavy chain
<220> FEATURE:
<221> NAME/KEY: MISC_FEATURE
<222> LOCATION: (1)..(118)
<223> OTHER INFORMATION: Variable region
<220> FEATURE:
<221> NAME/KEY: MISC_FEATURE
<222> LOCATION: (23)..(23)
<223> OTHER INFORMATION: Xaa is Ala or Cys
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(107)
<223> OTHER INFORMATION: CDR3
<220> FEATURE:
<221> NAME/KEY: MISC_FEATURE
<222> LOCATION: (119)..(448)
<223> OTHER INFORMATION: Constant region
<220> FEATURE:
<221> NAME/KEY: MISC_FEATURE
<222> LOCATION: (215)..(215)
<223> OTHER INFORMATION: R214 (EU) allotype
<220> FEATURE:
<221> NAME/KEY: MISC_FEATURE
<222> LOCATION: (357)..(357)
<223> OTHER INFORMATION: E356 (EU) allotype
<220> FEATURE:
<221> NAME/KEY: MISC_FEATURE
<222> LOCATION: (359)..(359)
<223> OTHER INFORMATION: M358 (EU) allotype

<400> SEQUENCE: 1

Gln Val Gln Leu Val Glu Ser Gly Gly Gly Val Val Gln Pro Gly Arg
 1               5                  10                  15

Ser Leu Arg Leu Ser Cys Xaa Ala Ser Gly Phe Thr Phe Ser Ser Tyr
             20                  25                  30

Thr Met His Trp Val Arg Gln Ala Pro Gly Lys Gly Leu Glu Trp Val
         35                  40                  45

Thr Phe Ile Ser Tyr Asp Gly Asn Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
             85                  90                  95
```

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

```
<210> SEQ ID NO 2
<211> LENGTH: 215
<212> TYPE: PRT
<213> ORGANISM: Homo sapiens
<220> FEATURE:
<221> NAME/KEY: MISC_FEATURE
<223> OTHER INFORMATION: Anti-CTLA4 antibody light (kappa) chain
<220> FEATURE:
<221> NAME/KEY: MISC_FEATURE
<222> LOCATION: (1)..(108)
<223> OTHER INFORMATION: Variable region
```

```
<220> FEATURE:
<221> NAME/KEY: MISC_FEATURE
<222> LOCATION: (24)..(35)
<223> OTHER INFORMATION: CDR1
<220> FEATURE:
<221> NAME/KEY: MISC_FEATURE
<222> LOCATION: (51)..(57)
<223> OTHER INFORMATION: CDR2
<220> FEATURE:
<221> NAME/KEY: MISC_FEATURE
<222> LOCATION: (68)..(68)
<223> OTHER INFORMATION: Xaa is Ser or Cys
<220> FEATURE:
<221> NAME/KEY: MISC_FEATURE
<222> LOCATION: (90)..(98)
<223> OTHER INFORMATION: CDR3
<220> FEATURE:
<221> NAME/KEY: MISC_FEATURE
<222> LOCATION: (109)..(215)
<223> OTHER INFORMATION: Constant region

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
50                  55                  60

Gly Ser Gly Xaa Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 3
<211> LENGTH: 437
<212> TYPE: PRT
<213> ORGANISM: Artificial Sequence
<220> FEATURE:
<223> OTHER INFORMATION: Rat-mouse chimeric
<220> FEATURE:
<221> NAME/KEY: MISC_FEATURE
<223> OTHER INFORMATION: Anti-CD137 antibody heavy chain
<220> FEATURE:
<221> NAME/KEY: MISC_FEATURE
<222> LOCATION: (1)..(113)
<223> OTHER INFORMATION: Variable region
```

```
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(65)
<223> OTHER INFORMATION: CDR2
<220> FEATURE:
<221> NAME/KEY: MISC_FEATURE
<222> LOCATION: (98)..(102)
<223> OTHER INFORMATION: CDR3
<220> FEATURE:
<221> NAME/KEY: MISC_FEATURE
<222> LOCATION: (114)..(437)
<223> OTHER INFORMATION: Constant region

<400> SEQUENCE: 3

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30

Gly Val His Trp Ile Arg Gln Pro Pro Gly Lys Gly Leu Glu Trp Met
        35                  40                  45

Gly Ile Ile Tyr Tyr Asp Gly Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Ile Asn Ser Leu Gln Thr Asp Asp Thr Ala Met Tyr Tyr Cys Ala
                85                  90                  95

Arg Ile His Phe Asp Tyr Trp Gly Gln Gly Val Met Val Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Gln Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
    210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Asp Ile
                245                 250                 255

Ser Lys Asp Asp Pro Glu Val Gln Phe Ser Trp Phe Val Asp Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
    290                 295                 300

Asn Gly Lys Glu Phe Lys Cys Arg Val Asn Ser Ala Ala Phe Pro Ala
305                 310                 315                 320
```

```
                                         -continued

Pro Ile Glu Lys Thr Ile Ser Lys Thr Lys Gly Arg Pro Lys Ala Pro
                325                 330                 335

Gln Val Tyr Thr Ile Pro Pro Pro Lys Glu Gln Met Ala Lys Asp Lys
            340                 345                 350

Val Ser Leu Thr Cys Met Ile Thr Asp Phe Phe Pro Glu Asp Ile Thr
        355                 360                 365

Val Glu Trp Gln Trp Asn Gly Gln Pro Ala Glu Asn Tyr Lys Asn Thr
    370                 375                 380

Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser
                405                 410                 415

Val Leu His Glu Gly Leu His Asn His His Thr Glu Lys Ser Leu Ser
            420                 425                 430

His Ser Pro Gly Lys
        435

<210> SEQ ID NO 4
<211> LENGTH: 213
<212> TYPE: PRT
<213> ORGANISM: Artificial Sequence
<220> FEATURE:
<223> OTHER INFORMATION: Rat-mouse chimeric
<220> FEATURE:
<221> NAME/KEY: MISC_FEATURE
<223> OTHER INFORMATION: Anti-CD137 antibody light (kappa) chain
<220> FEATURE:
<221> NAME/KEY: MISC_FEATURE
<222> LOCATION: (1)..(106)
<223> OTHER INFORMATION: Variable region
<220> FEATURE:
<221> NAME/KEY: MISC_FEATURE
<222> LOCATION: (24)..(33)
<223> OTHER INFORMATION: CDR1
<220> FEATURE:
<221> NAME/KEY: MISC_FEATURE
<222> LOCATION: (49)..(55)
<223> OTHER INFORMATION: CDR2
<220> FEATURE:
<221> NAME/KEY: MISC_FEATURE
<222> LOCATION: (88)..(96)
<223> OTHER INFORMATION: CDR3
<220> FEATURE:
<221> NAME/KEY: MISC_FEATURE
<222> LOCATION: (107)..(213)
<223> OTHER INFORMATION: Constant region

<400> SEQUENCE: 4

Glu Ile Val Leu Thr Gln Ser Pro Thr Thr Ile Ala Ala Ser Pro Gly
1               5                   10                  15

Glu Lys Val Thr Ile Thr Cys Arg Ala Ser Ser Ser Val Ser Tyr Met
            20                  25                  30

Tyr Trp Tyr Gln Gln Lys Ser Gly Ala Ser Pro Lys Leu Trp Ile Tyr
        35                  40                  45

Asp Thr Ser Lys Leu Ala Ser Gly Val Pro Asn Arg Phe Ser Gly Ser
    50                  55                  60

Gly Ser Gly Thr Ser Tyr Ser Leu Ala Ile Asn Thr Met Glu Thr Glu
65                  70                  75                  80

Asp Ala Ala Thr Tyr Tyr Cys Gln Gln Trp Ser Thr Pro Leu Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
```

```
            115                 120                 125
Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
                195                 200                 205

Asn Arg Asn Glu Cys
    210

<210> SEQ ID NO 5
<211> LENGTH: 8
<212> TYPE: PRT
<213> ORGANISM: Artificial Sequence
<220> FEATURE:
<223> OTHER INFORMATION: Protease cleavable peptide

<400> SEQUENCE: 5

Leu Ser Gly Arg Ser Asp Asn His
1               5

<210> SEQ ID NO 6
<211> LENGTH: 7
<212> TYPE: PRT
<213> ORGANISM: Artificial Sequence
<220> FEATURE:
<223> OTHER INFORMATION: Protease cleavable peptide

<400> SEQUENCE: 6

Val Pro Leu Ser Leu Tyr Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Protease cleavable peptide

<400> SEQUENCE: 7

Pro Leu Gly Leu Ala Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Protease cleavable peptide

<400> SEQUENCE: 8

Val Leu Val Pro Met Ala Met Met Ala Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Protease cleavable peptide
```

```
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Ala or Val
<220> FEATURE:
<221> NAME/KEY: MISC_FEATURE
<222> LOCATION: (7)..(7)
<223> OTHER INFORMATION: Xaa is any amino acid

<400> SEQUENCE: 9

Xaa Xaa Gln Ala Arg Xaa Xaa
1               5

<210> SEQ ID NO 10
<211> LENGTH: 4
<212> TYPE: PRT
<213> ORGANISM: Artificial Sequence
<220> FEATURE:
<223> OTHER INFORMATION: Protease cleavable peptide

<400> SEQUENCE: 10

Ala Gly Pro Arg
1

<210> SEQ ID NO 11
<211> LENGTH: 4
<212> TYPE: PRT
<213> ORGANISM: Artificial Sequence
<220> FEATURE:
<223> OTHER INFORMATION: Protease cleavable peptide

<400> SEQUENCE: 11

Ala Ala Asn Leu
1

<210> SEQ ID NO 12
<211> LENGTH: 4
<212> TYPE: PRT
<213> ORGANISM: Artificial Sequence
<220> FEATURE:
<223> OTHER INFORMATION: Protease cleavable peptide

<400> SEQUENCE: 12

Pro Thr Asn Leu
1

<210> SEQ ID NO 13
<211> LENGTH: 8
<212> TYPE: PRT
<213> ORGANISM: Artificial Sequence
<220> FEATURE:
<223> OTHER INFORMATION: Protease cleavable peptide

<400> SEQUENCE: 13

Thr Ser Gly Arg Ser Ala Asn Pro
1               5

<210> SEQ ID NO 14
<211> LENGTH: 7
<212> TYPE: PRT
```

```
<213> ORGANISM: Artificial Sequence
<220> FEATURE:
<223> OTHER INFORMATION: Protease cleavable peptide
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Ala or Ser

<400> SEQUENCE: 14

Asp Glu Xaa Xaa Xaa Cys Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Protease cleavable peptide
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Ala or Ser

<400> SEQUENCE: 15

Asp Leu Xaa Xaa Xaa Thr Xaa
1               5

<210> SEQ ID NO 16
<211> LENGTH: 4
<212> TYPE: PRT
<213> ORGANISM: Artificial Sequence
<220> FEATURE:
<223> OTHER INFORMATION: Protease cleavable peptide
<220> FEATURE:
<221> NAME/KEY: MISC_FEATURE
<222> LOCATION: (4)..(4)
<223> OTHER INFORMATION: Xaa is Arg or Lys

<400> SEQUENCE: 16

Leu Ser Gly Xaa
1
```